United States Patent [19]
Van Boeckel et al.

[11] Patent Number: 5,705,489
[45] Date of Patent: Jan. 6, 1998

[54] BISCONJUGATES COMPRISING TWO SACCHARIDES AND A SPACER

[75] Inventors: Constant A. A. Van Boeckel; Peter D. J. Grootenhuis, both of Oss, Netherlands; Maurice Petitou, Paris, France; Pieter Westerduin, Oss, Netherlands

[73] Assignees: Akzo Nobel N.V., Arnhem, Netherlands; Elf Sanofi, Paris, France

[21] Appl. No.: 690,449

[22] Filed: Aug. 5, 1996

Related U.S. Application Data

[63] Continuation of Ser. No. 299,183, Aug. 31, 1994, abandoned.

[30] Foreign Application Priority Data

Sep. 1, 1993 [EP] European Pat. Off. ............. 93202562

[51] Int. Cl.⁶ ......................... A61K 31/70; C07H 15/00
[52] U.S. Cl. ........................... 514/25; 514/54; 514/61; 536/4.1; 536/17.2; 536/17.9
[58] Field of Search ..................... 514/25, 54, 61; 536/17.2, 17.9, 4.1

[56] References Cited

U.S. PATENT DOCUMENTS

| | | | |
|---|---|---|---|
| 4,818,816 | 4/1989 | Petitou et al. | 536/55.2 |
| 5,008,247 | 4/1991 | Meinetsberger | 514/23 |
| 5,037,973 | 8/1991 | Meinetsberger | 536/53 |

FOREIGN PATENT DOCUMENTS

| | | |
|---|---|---|
| 312086 | 4/1989 | European Pat. Off. |
| 0337327 | 10/1989 | European Pat. Off. |
| 0347964 | 12/1989 | European Pat. Off. |
| 0454220 | 10/1991 | European Pat. Off. |

OTHER PUBLICATIONS

L. Rosenfeld et al., *The Journal of Biological Chemistry*, 263:1:262–266, 1988.

S. Radoff et al., *The Journal of Biological Chemistry*, 259:1:166–172, 1984.

*CRC Handbook of Chemistry and Physics*, 58th Edition, p. C-4, 1977–78.

Primary Examiner—Kathleen K. Fonda
Attorney, Agent, or Firm—Mary E. Gormley

[57] ABSTRACT

The invention relates to a tuneable bisconjugate comprising two saccharides and a spacer, each saccharide being the same or different and comprising two to six monosaccharide units, at least one unit being uronic acid, characterized in that at least one of the saccharides per se has anti-thrombotic activity, and that the spacer connects at least one saccharide to the other through its non-reducing end, the chain length of the spacer being 20–120 atoms.

12 Claims, No Drawings

BISCONJUGATES COMPRISING TWO SACCHARIDES AND A SPACER

This application is a continuation of Ser. No. 08/299,183 filed Aug. 31, 1994, now abandoned.

The invention relates to tuneable bisconjugates comprising two saccharides and a spacer, to a process for the preparation thereof, a pharmaceutical composition containing the same, and a use of said bisconjugates for the manufacture of a medicament.

Antithrombotic bisconjugates comprising two saccharides and a spacer are known from European patent application 312,086. The saccharide moieties of these compounds contain sulfated galactopyranosyl, mannopyranosyl, or glucopyranosyl units. These saccharides do not belong to the class of glycosaminoglycans or glycosaminoglycanoids such as disclosed in European patent application 529,715, which contain uronic acids. It is not disclosed whether these saccharides per se show anti-thrombotic activity. Moreover, only a spacer is disclosed which has a very specific structure, and which can have a chain length as small as 8 atoms, whereas it is found that the bisconjugates of the present invention are not active when they have a spacer chain length smaller than 20 atoms. In addition, in the bisconjugates disclosed in EP 312,086 the saccharides are connected to the spacer through both their reducing ends.

The present invention relates to a tuneable bisconjugate comprising two saccharides and a spacer, each saccharide being the same or different and comprising two to six monosaccharide units, at least one unit being uronic acid, characterized in that at least one of the saccharides per se has anti-thrombotic activity, and that the spacer connects at least one saccharide to the other through its non-reducing end, the chain length of the spacer being 20–120 atoms.

Practically it is not interesting to synthesize glycosaminoglycans having 16 or more saccharide units, whereas fragmentation of heparin or other naturally occurring glycosaminoglycans leads to mixtures of compounds, mostly contaminated with other types of compounds, such as proteins, DNA, viruses and the like. From a medical point of view such mixtures are less attractive than pure and well-defined synthetic compounds, for instance because of the commonly occurring bleeding risks.

It has now been found that the properties of these larger glycosaminoglycans can be mimicked by two small saccharide molecules (comprising two to six monosaccharide units), at least one saccharide being able to interact with protease inhibitors such as AT-III or HC-II, connected to each other by a spacer. To obtain the minimal required distance between the two saccharides, a spacer length or minimal 20 atoms is required. Spacers longer than 120 atoms are less suitable because of synthetic reasons. It has further been found that the chemical structure of the spacer is of minor or no importance. The anti-thrombotic activity and the αXa/αIIa activity ratio of the bisconjugates of this invention depend on the nature of the saccharides, the site of their connection to the spacer, and the length of the spacers. Saccharides connected to a spacer through both their reducing ends, for instance, are not active.

At least one of the saccharides per se, preferably both saccharides per se, has (have) affinity for AT-III and/or HC-II, and/or has (have) anti-factor IIa and/or anti-factor Xa activity.

Suitable biconjugates are bisconjugates wherein at least one of the saccharides has the formula:

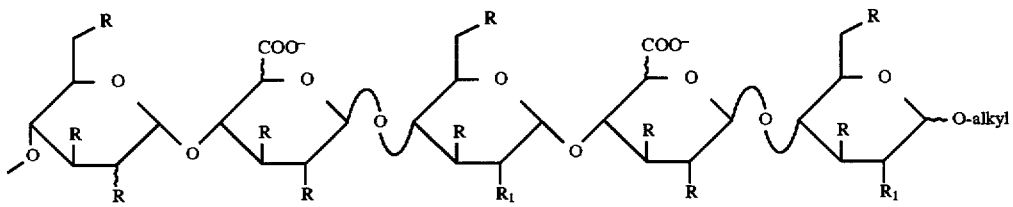

It is known that small carbohydrate molecules of the glycosaminoglycan type, are potent anti-Xa inhibitors. See for instance European patent 84999. Later filed patent applications showed that many variants of these basic molecules have similar activities. It is nowadays clear that these relatively small molecules (pentasaccharides are typical examples) interact with only one of the serine protease inhibitors, usually with anti-thrombin III (AT-III). The activated saccharide AT-III complex then inhibits selectively factor Xa. From investigations with natural occurring heparin and its fragments, it is known that longer glycosaminoglycans are required for the AT-III mediated inactivation of factor IIa (thrombin). Longer glycosaminoglycans having at least 16 saccharide units show anti-Xa as well as anti-IIa activity.

wherein each

R is independently selected from H, OH, $OSO_3^-$, and alkoxy; $R_1$ is independently selected from $OSO_3^-$ and $NHSO_3^-$; and the wrinkled lines denote either an upward or a downward bond, and the negative charges are compensated by hydrogen or an alkali metal cation.

The term alkyl, as used in this formula, is an alkyl group having 1–8, and preferably 1–4 carbon atoms. The most preferred alkyl group is the methyl group.

The term alkoxy means an alkoxy group having 1–8, and preferably 1–4 carbon atoms. Most preferred is the methoxy group.

Sodium is the preferred alkali metal.

In the most preferred bisconjugates at least one of the saccharides has the formula:

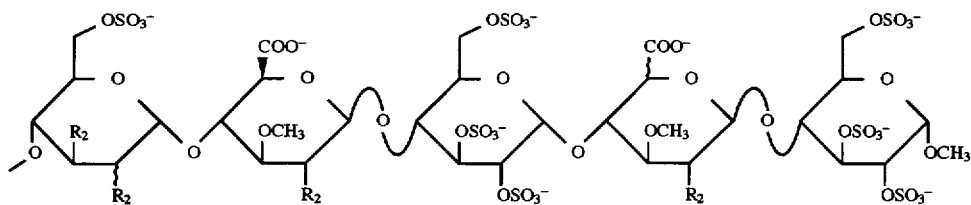

wherein $R_2$ is independently $OSO_3^-$ or $OCH_3$.

As previously emphasized, the chemical structure of the spacer is of secondary importance. For synthetic convenience, however, some spacers are more appropriate than others. Simple spacers that can easily be introduced are for example spacers having the formula:

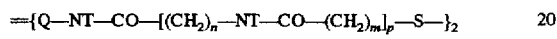

or

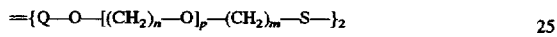

wherein
one of the two groups Q is attached to the non-reducing end of one of the saccharides and the other group Q is attached to the reducing or non-reducing end of the other saccharide, and each of the groups Q is a phenylene ($C_6H_4$) group or $-[(CH_2O)_q-(CH_2)_r-O]_s-[(CH_2)_t-NT-CO]_u-(CH_2)_v$, and T is independently hydrogen or alkyl as previously defined; q being 0 or 1; r and t being independently 2–4; and s being independently 1–12; preferably 1–6; u and v being independently 1–6; n is 1–8; m is 1–8, p is 1–12, and the total number of atoms is 20–120.

Another suitable spacer has the formula:

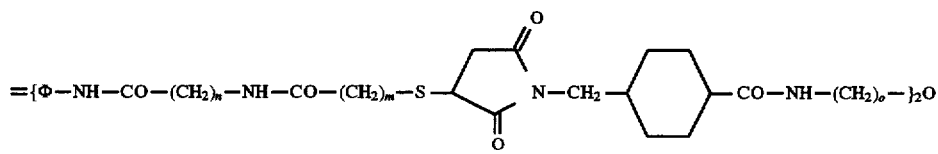

wherein
one of the two groups φ is attached to the non-reducing end of one of the saccharides and the other group φ is attached to the reducing or non-reducing end of the other saccharide and φ denotes a phenylene ($C_6H_4$) group; n, m, and o are independently 1–8, and the total number of atoms is 20–120.

Other equally suitable spacers have the formula:

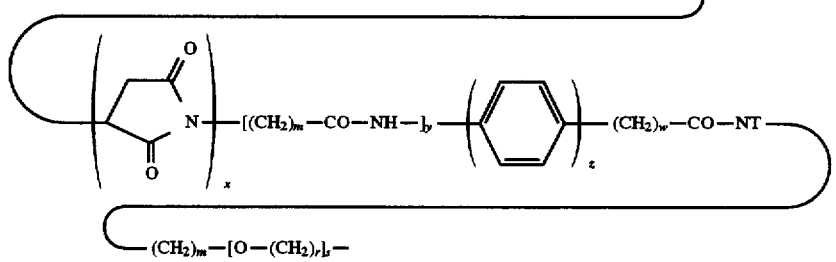

wherein
one of the two free valencies of the spacer is attached to the non-reducing end of one of the saccharides and the other free valency of the spacer is attached to the reducing or non-reducing end of the other saccharide, and T is independently H or alkyl as previously defined; m is independently 1–8; r is independently 2–4; s is independently 1–12, preferably 1–6; w is 0–10, preferably 0–7; x is 0 or 1; y is 0 or 1; z is 0 or 1, and the total number of atoms is 20–120.

These embodiments are preferred because of their easy accessibility, however, the spacers are by no means limited to the above-mentioned.

The bisconjugates of the invention are called symmetric when both saccharides are the same. The bisconjugates are called asymmetric when both saccharides are different from each other. Preferably asymmetric bisconjugates comprise one saccharide not having uronic acid units, thus being different from glycosaminoglycans and glycosaminoglycanoids, for example a saccharide consisting of glucose-units, e.g. cellobiose, maltotriose or maltopentaose or derivatives thereof.

The bisconjugates of the invention can be prepared by methods known for the preparation of analogous compounds. Usually the carbohydrate moieties are prepared by using methods known in the literature (for example using the methods of EP 84999, EP 301618, EP 454220, EP 529715 and EP application 9304769). By application of temporary protective groups the desired hydroxy group can be freed for coupling to the spacer. More preferred, however, is the attachment of a suitable linker group to the desired hydroxy group, for instance a nitrophenyl group, which during the usual reduction step (the cleavage of the benzyl protective groups) converts into the corresponding aniline group, the amino group of which can be used to couple with the remainder of the spacer (having for instance a halogen or an active ester of a carboxylic group at its end), or can optionally be temporarily protected and coupled to the remainder of the spacer in a later stage. The aniline group thereby becomes part of the spacer.

Another method, especially useful when the carbohydrate moieties are the same, is the coupling of the carbohydrate moiety to a moiety which corresponds to a half of the spacer and whose end not to be bonded to the saccharide is protected with a protective group, which moiety is prone to dimerization without said protective group. After deprotection the molecule dimerizes under the suitable reaction conditions to the biconjugate of the invention.

A variant of the above-mentioned method is the coupling of a part of the spacer to the carbohydrate moiety, after which the spacer part is further built-up by chemical condensation. This method is particularly useful for the preparation of bisconjugates with various spacer lengths, starting from the same carbohydrate moieties.

Yet another method is coupling of the spacer, or a half of the spacer, to a part of the carbohydrate moiety, which is coupled by standard carbohydrate coupling techniques with the remaining carbohydrate part to the required bisconjugate of half of the bisconjugate, after which, when necessary, deprotection and dimerization of the spacer can be performed as previously described.

The bisconjugates of the invention can be used for the treatment or prevention of thrombotic disorders or smooth muscle cell proliferation. The bisconjugates of the invention may be administered enterally or parenterally, and for humans preferably in a daily dosage of 0.001–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the bisconjugates, when orally, buccally or sublingually active, may be compressed into solid dosage units, such as pills and tablets, or they may be processed into capsules or suppositories. When parenterally active, the bisconjugates can also be applied as an injection or infusion preparation by means of pharmaceutically suitable liquids in the form of a solution, suspension, emulsion, or as a spray, e.g. a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The tuneability of the compounds of the invention is demonstrated in Tables I, II and III. It appears that the saccharides, the length of the spacer, and combinations thereof can tune the αXa/αIIa activity ratio.

The spacer length is the number of atoms of the spacer, counted along the shortest chain between the two saccharides, not counting the oxygen atoms of the saccharides which are connected to the spacer.

TABLE I

Bisconjugates having different saccharide moieties and the same spacer length.

| bisconj. | spacerl. (atoms) | αXa act.[a] | αIIa act.[b] | αXa/αIIa |
|---|---|---|---|---|
| VII | 54 | 767 | 14 | 54.8 |
| V | 54 | 638 | 36 | 17.7 |
| VI | 54 | 278 | 156 | 1.78 |
| VIII | 54 | 49 | 91 | 0.54 |
| X | 52 | 181 | 71 | 2.56 |
| XI | 52 | 163 | 161 | 1.01 |
| IX | 52 | 79 | 108 | 0.73 |
| IV | 52 | 17 | 31 | 0.54 | bisconj. = bisconjugate
spacerl. = spacer length
[a]anti-Xa activity (units/mg) was determined according to the method of A. N. Teien and M. Lee, Thrombosis Research, 10, 399–410 (1977).
[b]anti-IIa activity (units/mg) was determined according to the method of M. L. Larson et al., Thrombosis Research, 13, 285–288 (1978).

Conclusion: In Table I it is shown that the αXa/αIIa activity ratio of the bisconjugates can be tuned by variation of the saccharides.

TABLE II

Bisconjugates with the same saccharide moieties and different spacer lengths.

| bisconj. | spacerl. (atoms) | αXa act. | αIIa act. | αXa/αIIa |
|---|---|---|---|---|
| I | 32 | 704 | 15 | 46.9 |
| III | 46 | 419 | 21 | 20.0 |
| II | 57* | 628 | 120 | 5.23 |

*spacer length determined via the methylene group of the cyclopentyl groups (shortest chain).

Conclusion: Table II illustrates that the αXa/αIIa activity ratio of the bisconjugates can be tuned by variation of the spacer length.

TABLE III

Bisconjugates having miscellaneous saccharides and/or spacer lengths.

| bisconj. | spacerl. (atoms) | αXa act. | αIIa act. | αXa/αIIa |
|---|---|---|---|---|
| XIV | 53 | 493 | 64 | 7.7 |
| XIII | 56* | 281 | 327 | 0.86 |
| XII | 56* | 41 | 279 | 0.15 |

*spacer length determined via the methylene group of the cyclopentyl groups (shortest chain).

Conclusion: Table III shows tuning of the αXa/αIIa activity ratio of the bisconjugates by changing saccharides and spacer lengths.

The invention is further illustrated by the following examples.

nitrobenzene (1.63 ml) was added during 2 min. After 30 min of stirring the mixture was concentrated, diluted with dichloromethane and water and extracted. After conventional work-up the residue was purified by column chromatography to give 4 g of compound 2.

Compound 2 was converted into compound 3 by acetolysis, followed by saponifiation which gave compound 4, which after reaction with trichloroactonitrile afforded compound 5. For the synthesis of compounds 3, 4, and 5 procedures were used as described for the preparation of compounds 9 (vide infra), 41, and 42 (see example 4), respectively.

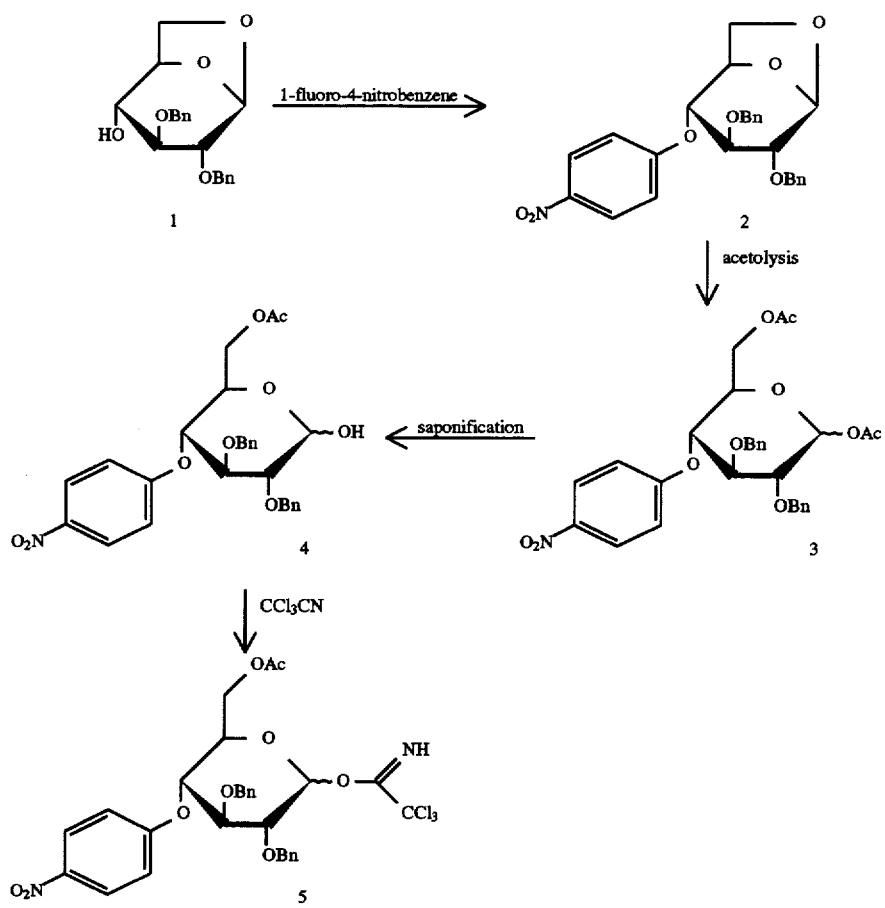

EXAMPLE 1

Monosaccharide 5

Compound 1 (3.5 g) (see Carb. Res. 1989, 186(2), 189–205) was dissolved in dimethylformamide (30 ml) and sodium hydride 560 mg) was added under nitrogen atmosphere. The mixture was cooled to 0° C. and 1-fluoro-4-

Tetrasaccharide 14

Compound 7 was prepared from compound 6 (see Bioorganic and Medicinal Letters 1992, 2(9), 905) according to the procedure as described for compound 39 (see example 4).

Compound 7 (14.6 g) was dissolved in acetone (260 ml) and cooled to 0° C. At this temperature a solution of chromium(VI)oxide (10.8 g) in a mixture of water (53 ml)

and concentrated sulfuric acid (10.5 ml) was added dropwise. The mixture was stirred for 16 hours at 2° C. Excess of chromium(VI)oxide was destroyed with methanol and after neutralisation of the mixture with sodium hydrogencarbonate, water was added. After extraction with dichloromethane the organic layer was dried and concentrated. The residual oil was dissolved in dry dimethylformamide (174 ml). Potassium hydrogencarbonate (7 g) and iodomethane (7 ml) were added and the mixture was stirred for 3 hours at room temperature. After concentration the residue was purified by silica gel chromatography to give 9.1 g of compound 8.

Compound 8 (2.8 g) was dissolved in a mixture of acetic anhydride (50 ml), acetic acid (0.3 ml) and trifluoroacetic acid (3.0 ml). After 3 hours of stirring the mixture was concentrated and coevaporated with toluene to give 3.1 g of compound 9.

Compound 10 was prepared by saponification of compound 9 which subsequently was converted to imidate 11. Procedures as described for the preparation of compounds 41 and 42 were utilized (see example 4).

tetrasaccharide 14 was obtained. Procedures as described for the preparation of compounds 43 and 44 were followed (see example 4).

Mol sieves 4 Å (70 mg) were added to a solution of 79 mg of tetrasaccharide 14 and 70 mg of monosaccharide 5 in 2.5 ml of dichloromethane. The mixture was cooled to −20° C. and 6.8 µmol of trimethysilyl trifluorormethanesulfonate were added. The mixture was stirred for 30 min and sodium hydrogencarbonate was added. The mixture was filtered, the solvent evaporated, and the residue purified by silica chromatography to give 88 mg of pentasaccharide 15 which were dissolved in 7.3 ml of tetrahydrofuran and cooled to −5° C. At this temperature 2.6 ml of 30% aq. hydrogen peroxide were added and after 10 min 1.2 ml of 1.25M lithium hydroxide solution were added. The mixture was stirred overnight at 0° C. 4.8 ml of methanol and 1.3 ml of 4M sodium hydroxide solution were added, and after stirring for 1 h the temperature was raised to 20° C. and the mixture was stirred for another 20 h. The reaction mixture was acidified to pH 3 with 6N hydrochloric acid at 0° C., and the saponified product was extracted with ethyl acetate. The

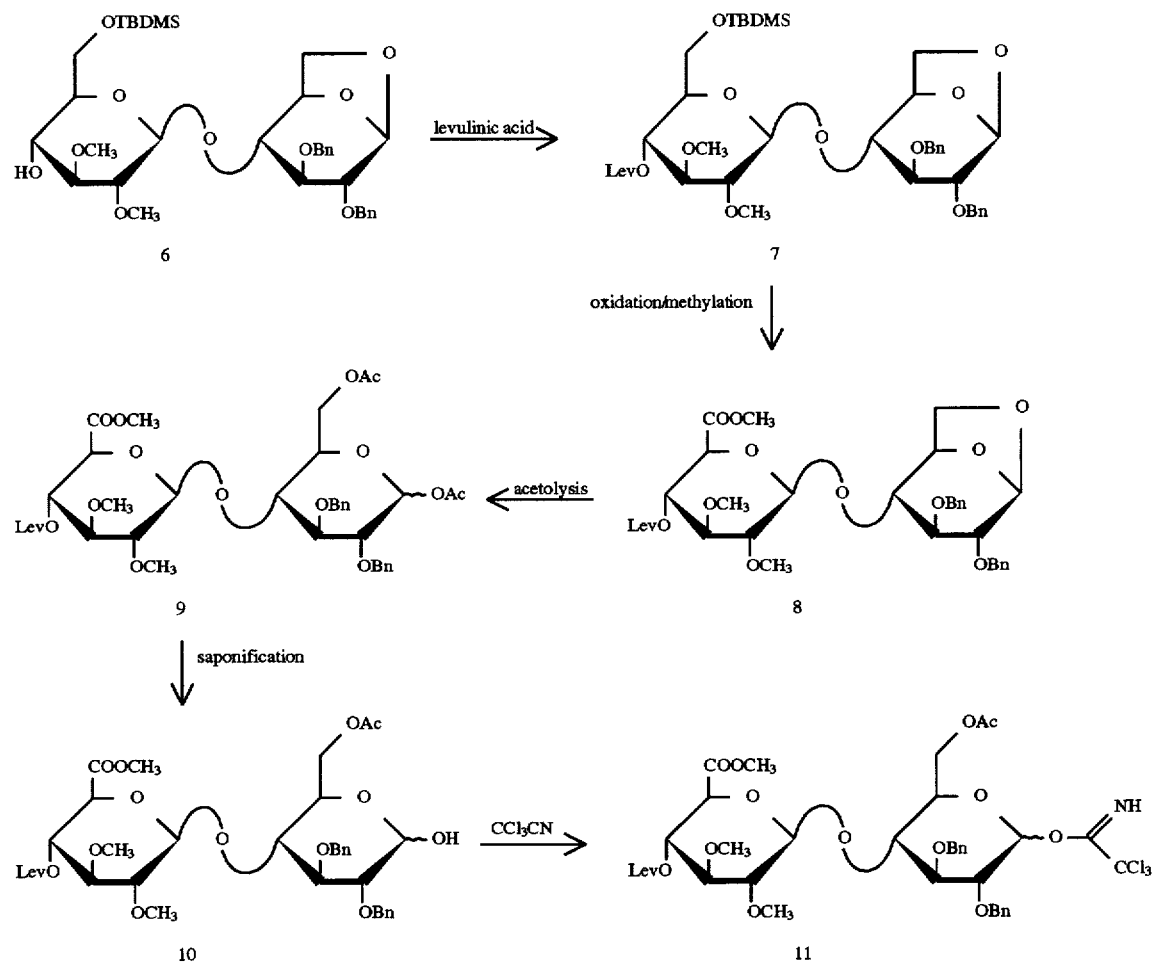

Compound 11 was coupled with compound 12 (see Jaurand G., et al., Bioorganic and Medicinal Chem. Lett., 2 (9), 897–900 (1992), compound 12) to form compound 13 from which the Lev-group was removed as a result of which excess of hydrogen peroxide was decomposed by extraction with a 5% sodium sulfite solution, and the organic mixture was dried over magnesium sulfate and evaporated to give 89 mg of crude pentasaccharide 16.

Pentasaccharide 16 was dissolved in 10.2 ml of dimethylformamide and 55 mg of 10% Pd on charcoal were added.

After hydrogenolysis overnight 64 mg of crude pentasaccharide 17 were obtained.
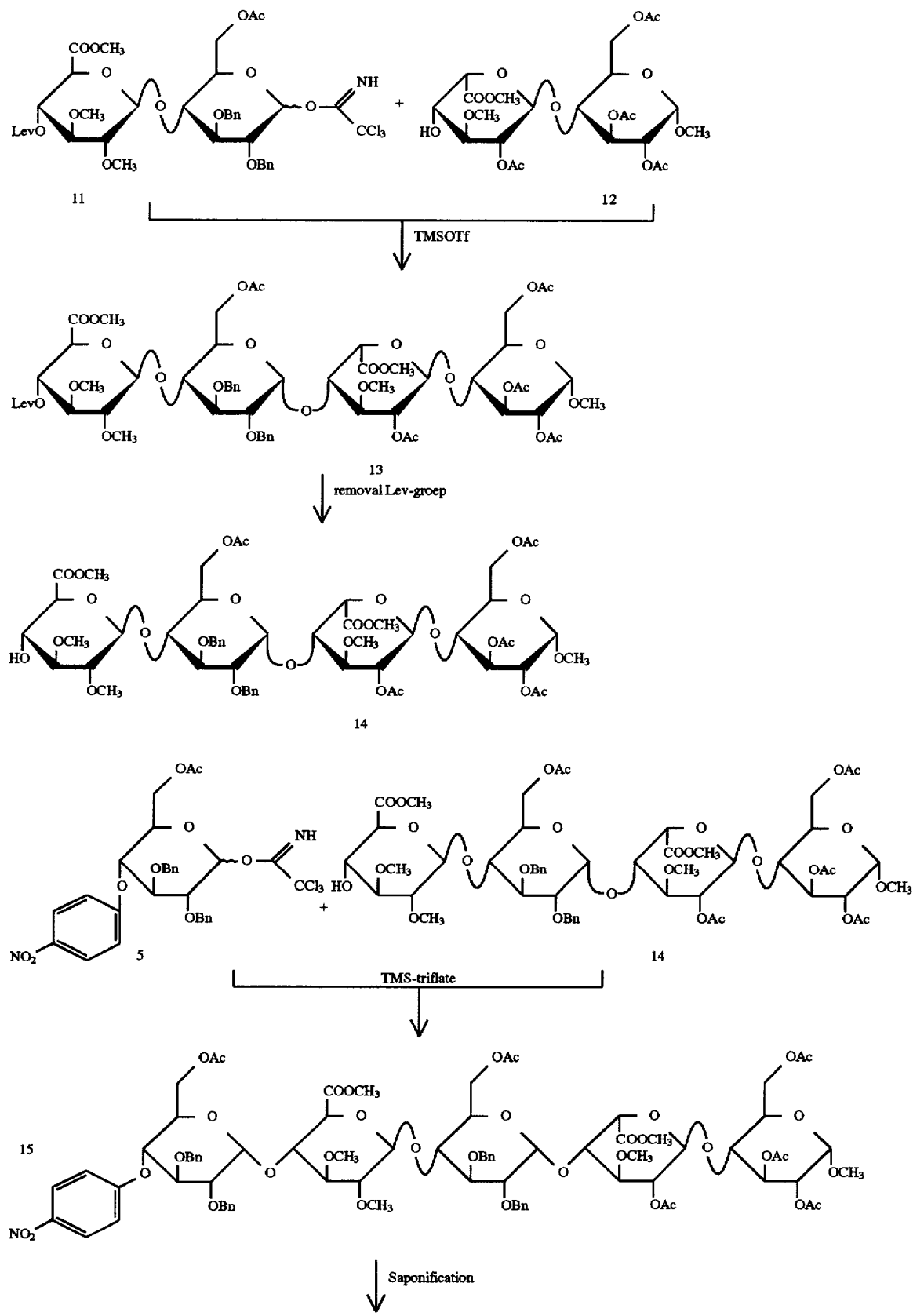

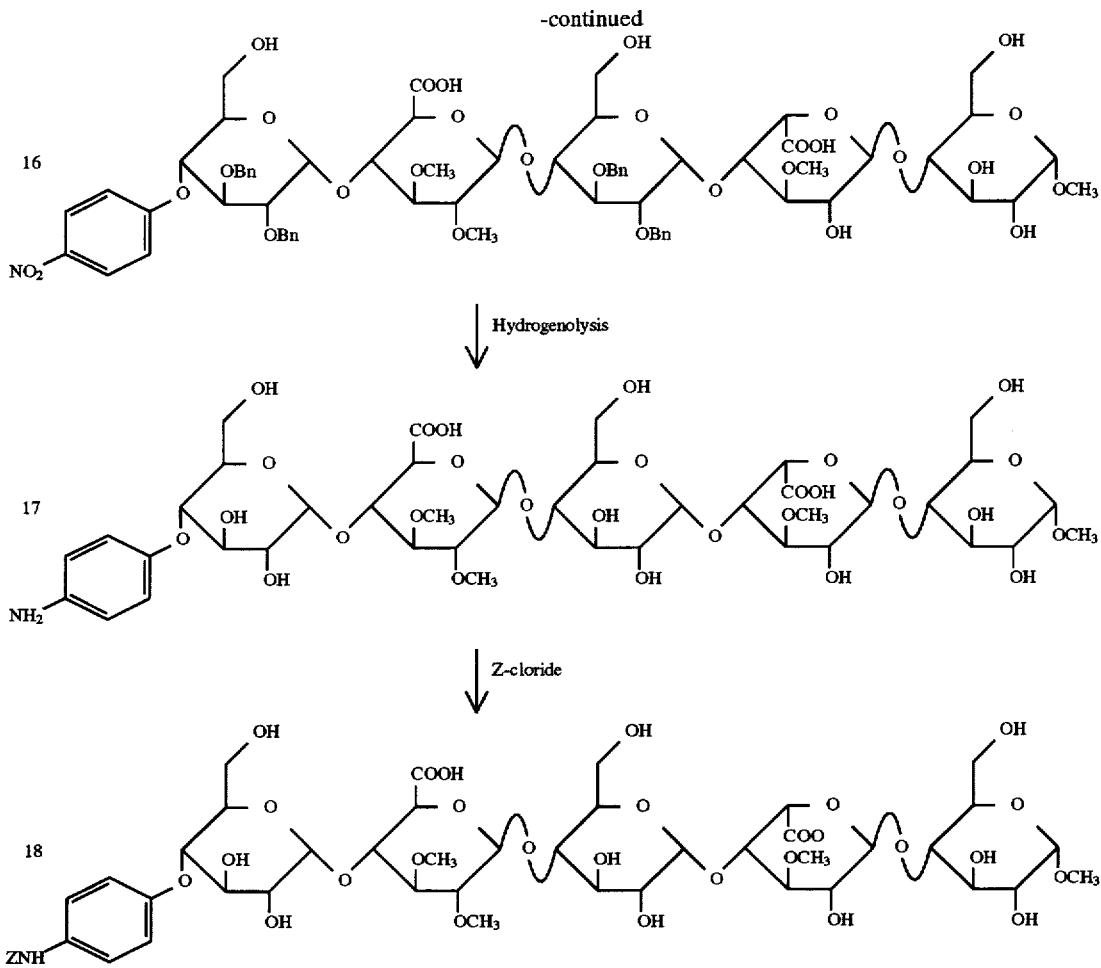

Pentasaccharide 17 (49 mg) was dissolved in 2 ml of a mixture of ethanol-water (1:1), and to this mixture were added 16 mg of sodium hydrogencarbonate and 10.4 µl of benzyloxycarbonylchloride (Z—Cl). After stirring for 4 h at room temperature the solvent was evaporated and methanol was added to the residue. The salts were filtered off and the filtrate was evaporated to give 67 mg of crude pentasaccharide 18, which were dissolved in 2.5 ml of dry dimethylformamide. Under nitrogen 442 mg of triethylamine sulfurtrioxide were added and the mixture was stirred overnight at 50° C., after which an aqueous solution of sodium hydrogencarbonate was added under ice cooling. The mixture was stirred for 1 h at room temperature, concentrated to a small volume and desalted on a Sephadex G-25 column. The isolated product was eluted with water on a Dowex 50WX8 Na⁺ column to give 104 mg of pentasaccharide 19. 100 mg of pentasaccharide 19 were dissolved in 8 ml of water, 10% Pd on charcoal was added, and the mixture was hydrogenolysed overnight to give 83 mg of pentasaccharide 20. $[\alpha]_D^{20}=+58.1°$ (c=1; water).

9.6 mg of pentasaccharide 20 and 4.8 mg of sulfo-LC-SPDP were dissolved in a mixture of 0.1 ml of ethanol and 0.35 ml of an aqueous 0.05M disodium hydrogenphosphate solution having a pH 7.8. The mixture was stirred for 3 h and desalted on a Sephadex G-25 column to give 9.0 mg of monoconjugate 21.

Monoconjugate 21 (8.9 mg) was dissolved in 1.5 mg of an aqueous 0.05M sodium dihydrogenphosphate solution having a pH 8.0. 157 µl of a 0.05M solution of tributylphosphine in isopropanol were added at room temperature, the mixture was stirred for 1 h and air was passed through the reaction mixture. After desalting of the mixture on a Sephadex G-25 column, the crude bisconjugate was purified by HPLC using a mono Q anion exchange column to give 4.0 mg of bisconjugate I. $[\alpha]_D^{20}=+45.7°$ (c=0.35; water).

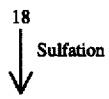

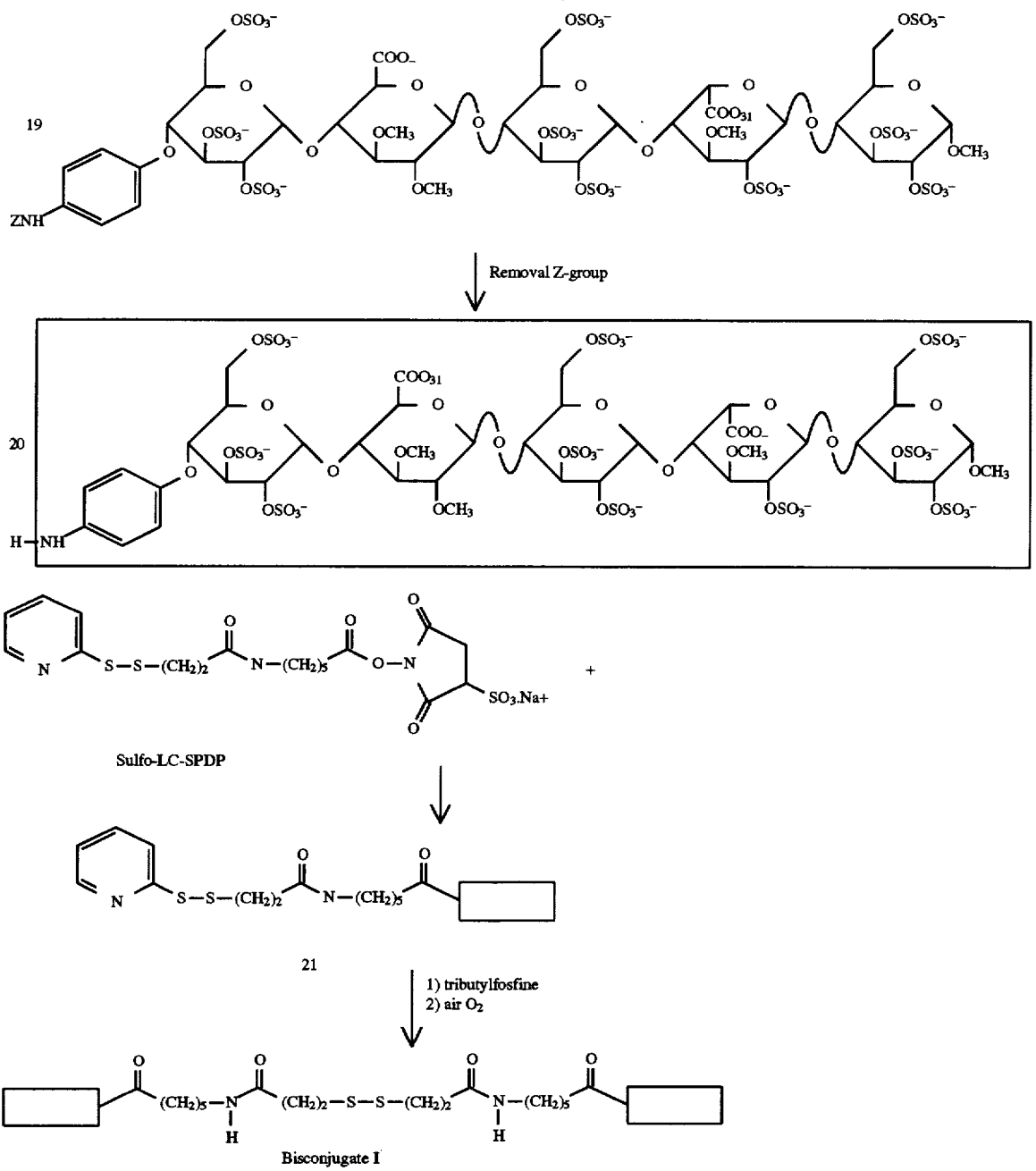

EXAMPLE 2

Monoconjugate 21 (14.7 mg) was dissolved in a mixture of 1 ml of methanol and 2 ml of an aqueous solution of 0.1M sodium dihydrogenphosphate pH 8. 247 μl of a 0.05M solution of tributylphosphine in isopropanol were added under nitrogen at room temperature. The mixture was stirred for 1 h and a solution of 1.68 mg of 23 in 0.5 ml of dimethylformamide were added and the mixture was stirred for another 3 h. After desalting of the mixture on a Sephadex G-25 column, the crude product was further purified by elution with a 0.05M aqueous sodium chloride solution containing 10% acetonitrile on a Sephadex G-50 column. The pooled fractions were desalted on Sephadex G-25 to give 5.5 mg of bisconjugate II. $[\alpha]_D^{20}$=+7.0° (c=0.34; water).

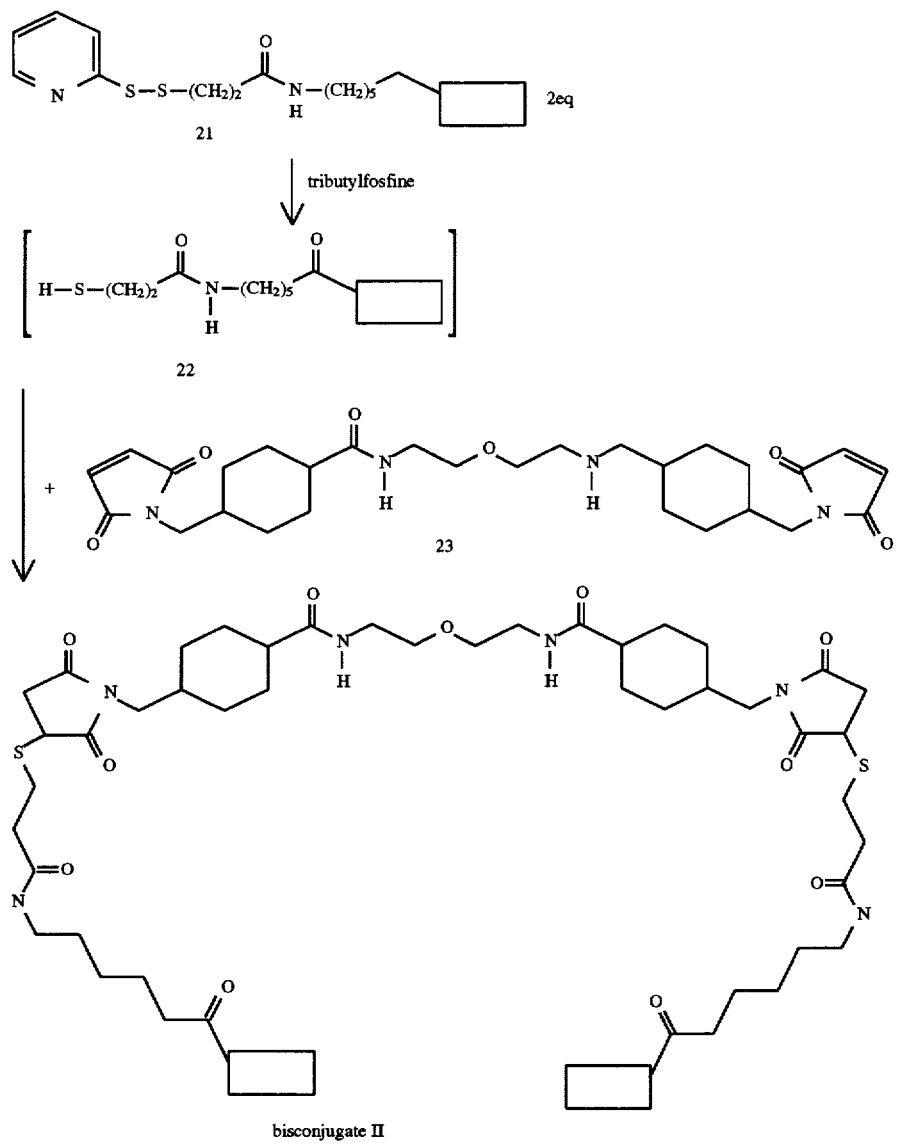

bisconjugate II

EXAMPLE 3

Methyl 2,3,6-tri-O-benzyl-α-D-glucopyranoside (2.1 g) 24 was dissolved in 75 ml of dimethylformamide and 5.5 ml of tetraethylene glycol di-p-tosylate were added at room temperature. Sodium hydride (162 mg) was added and the mixture was heated for 2 h at 50° C. Lithium azide (4.5 g) was added and the reaction mixture was stirred at 70° C. for another 5 h. The mixture was then concentrated and purified by column chromatography to give 1.52 g of compound 25.

To a solution of compound 25 (768 mg) in 40 ml of acetic anhydride at −20° C., 10 ml of a 5% (v/v) solution of sulfuric acid in acetic anhydride (cooled to −20° C.) were added. The mixture was stirred for 10 min at this temperature and sodium acetate (3.5 g) was then added to stop the reaction. After 10 min the mixture was extracted with ethyl acetate, the combined extracts were washed with a 10% aqueous sodium hydrogencarbonate solution, dried, and concentrated. Column chromatography of the crude product gave 573 mg of compound 26.

Compound 26 (269 mg) was dissolved in a mixture of 5.5 ml of dimethylformamide, 31 µl of acetic acid, and 28 µl of hydrazine monohydrate. The mixture was stirred for 3 h at room temperature, diluted with dichloromethane and water and extracted. Conventional work-up and column chromatography of the product yielded 158 mg of compound 27.

Compound 27 (158 mg) was dissolved in 2 ml of dichloromethane. Trichloroacetonitrile (0.13 ml) and cesium carbonate (17.8 mg) were added under nitrogen atmosphere. The mixture was stirred for 1 h at room temperature, filtered and evaporated. Column chromatography of the product yielded 182 mg of compound 28.

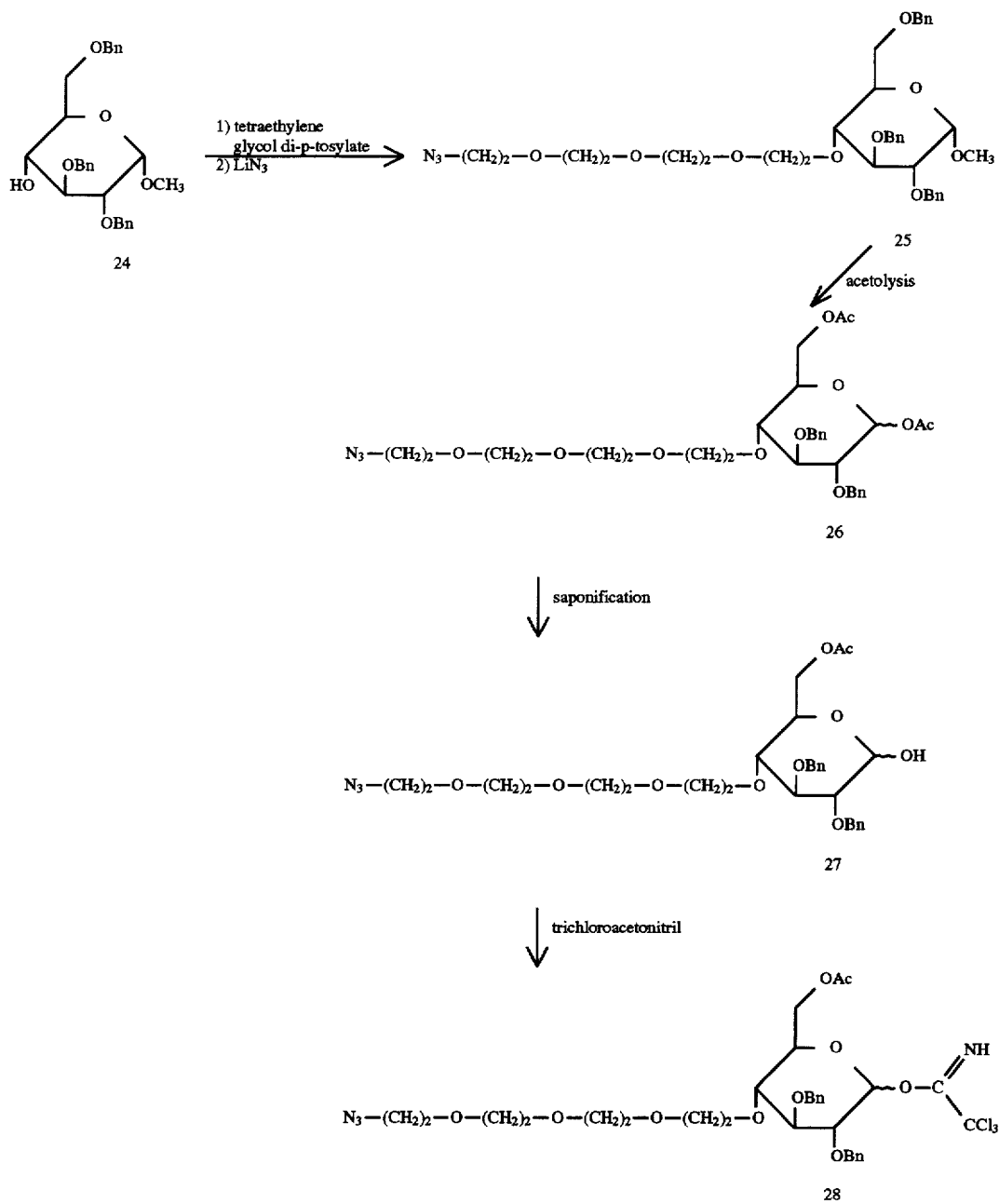
Compound 31 was prepared by coupling compound 11 with compound 29 (see H. Lucas et al., Angew. Chem. 1993, 105, 462–464) to form compound 30 from which the Lev- group was removed. Procedures as described for the preparation of compounds 43 and 44 were followed (see example 4).

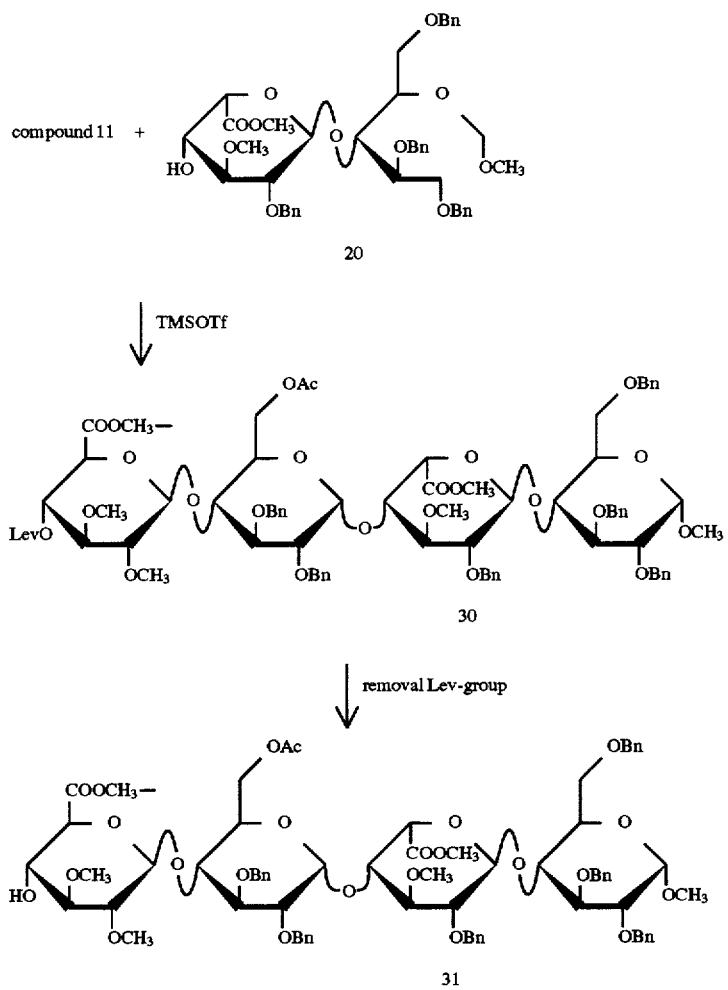

Compounds 32, 33, and 34 were prepared in a manner similar to that as described for compounds 15, 16, and 17 respectively (see example 1).

Compound 34 (35 mg) was dissolved in 0.35 mg of a stock-solution of 280 µl of triethylamine in 20 ml of dimethylformamide. N-(benzyloxycarbonyloxy)-succinimide (10.6 mg) was added at pH 7.5 and after 30 min of stirring the solvent was partly removed by evaporation. The residue was first purified on a Sephadex LH-20 column, followed by further purification on a Rp-18 column (acetonitrile:water:ammonia=95:5:2 v/v) to give 29.4 mg of compound 35.

Compound 36 was prepared in a similar manner as described for compound 19 (see example 1). $[\alpha]_D^{20}$=22.8° (c=0.3; water).

Compound 36 (51.4 mg) was dissolved in 4 ml of water and the catalyst (10% Pd/C) was added. The mixture was stirred under an atmosphere of hydrogen gas for 5 h at room temperature. After filtration the solvent was evaporated to give 47 mg of compound 37.

Compound 37 (15.1 mg) was dissolved in 450 µl of a solution of N,N-diisopropylethylamine in dimethylformamide:water=7:3 (pH 9.0) and excess of sulfosuccinimidyl 6-[3'(2-pyridyldithio)propioamido] hexanoate was added at a constant pH value of 9.0. After 20 min stirring the mixture was desalted on a Sephadex G-25 column with water:acetonitril 8:2 (v/v) to give 16 mg of crude compound 38.

Bisconjugate III was prepared from compound 38 in a similar manner as described in example 1 for the conversion of compound 21 into bisconjugate I. $[\alpha]_D^{20}$=+29.6° (c=0.125; water).

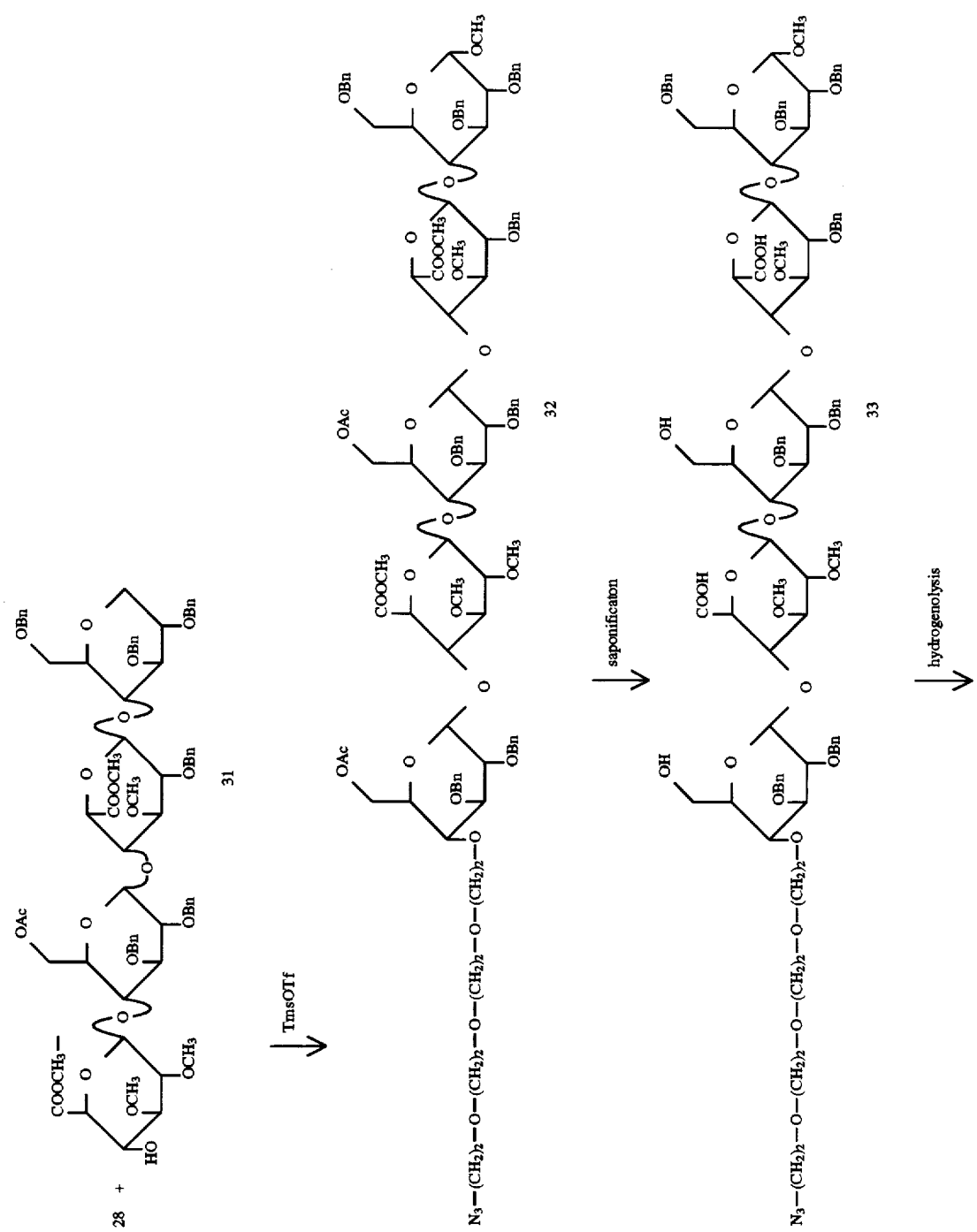

-continued
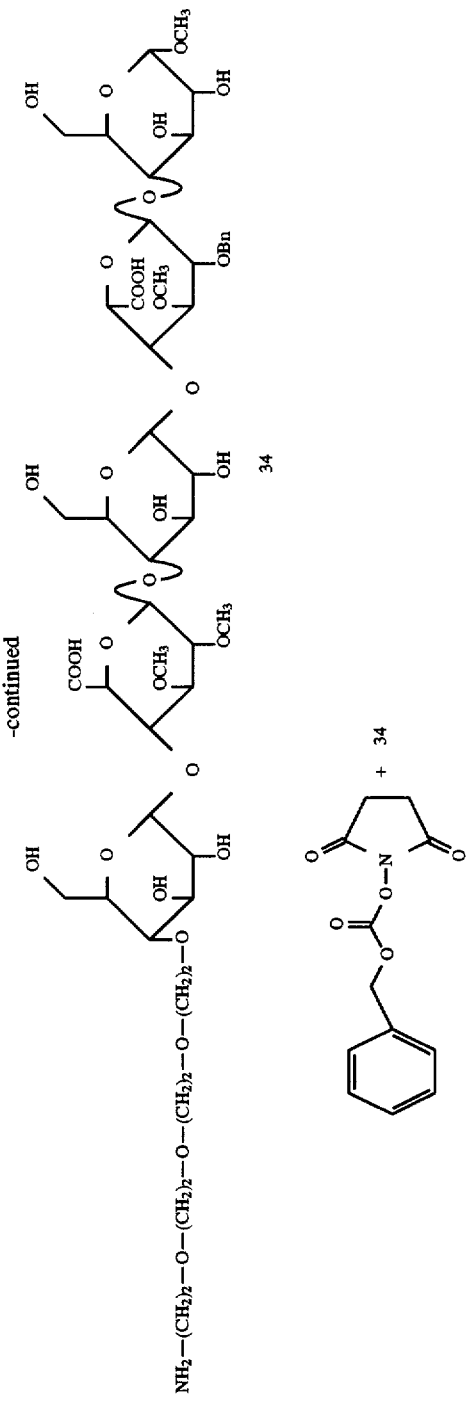
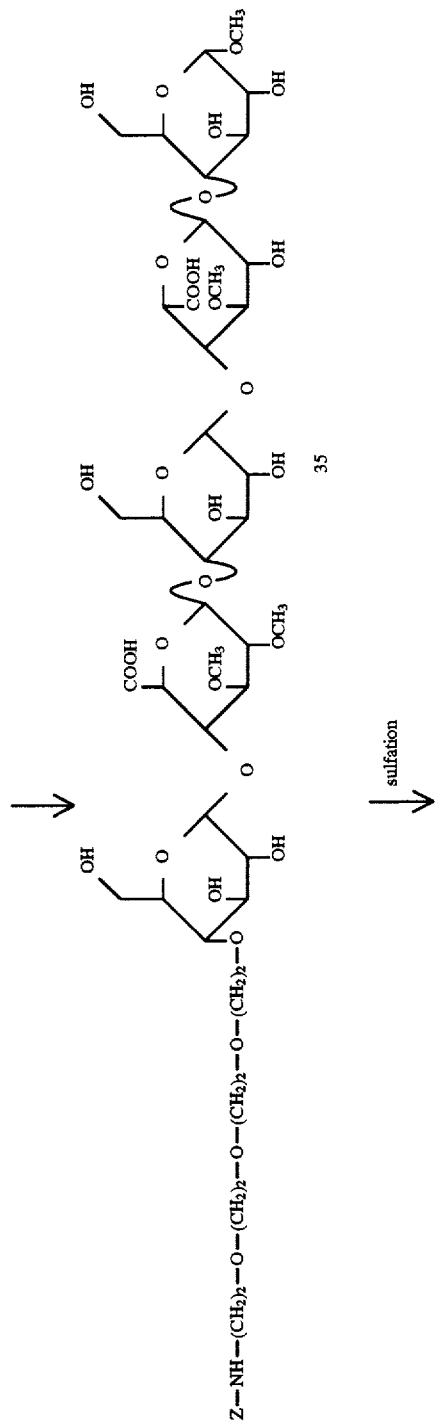

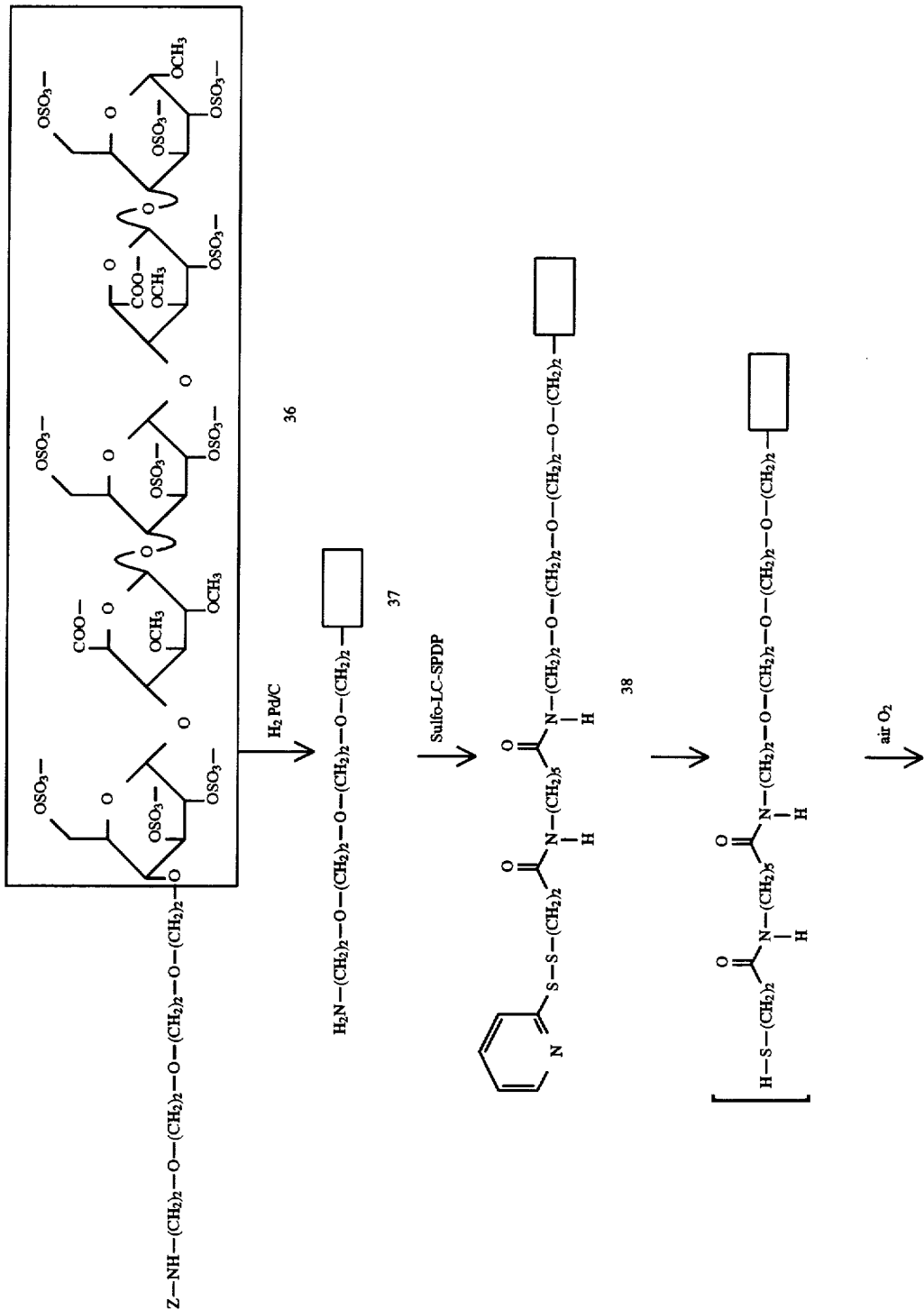

-continued
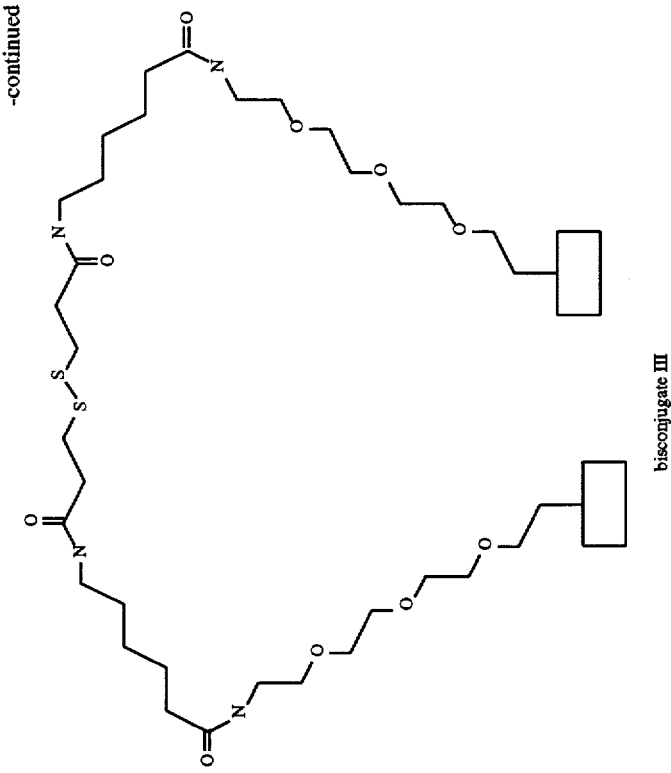
bisconjugate III

EXAMPLE 4

Bisconjugate IV ($[\alpha]_D^{20}$=+50.8° (c=0.32; water) was prepared according to the procedure of example 3, the differences being the use of tetrasaccharide 44 instead of 31, and the application of succinimido N-(benzyloxycarbonyloxy) glycine instead of N-(benzyloxycarbonylxoy) succinimide.

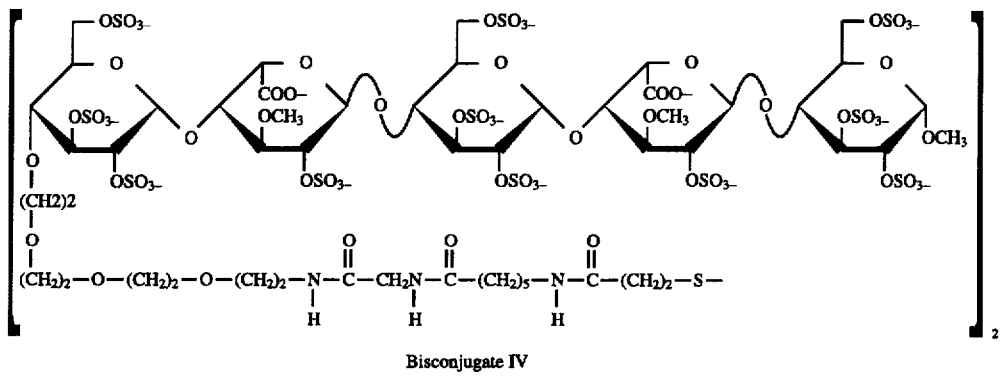

Bisconjugate IV

Preparation of tetrasaccharide 44

Disaccharide 29 (0.8 g) was dissolved in dioxane (5.3 ml), after which levulinic acid (278 mg), 1,3-dicyclohexylcarbodiimide (494 mg) and 4-dimethylaminopyridine (25 mg) were added. After 2 hours of stirring diethyl ether was added and the mixture was cooled to 0° C. Crystals were filtered off and the filtrate was concentrated. The residual oil was purified by column chromatography to give 900 mg of compound 39.

A solution of compound 39 (1 g) in acetic anhydride (50 ml) was cooled to −20° C. At this temperature 10 ml of solution A, which had been prepared by adding 1 ml of sulfuric acid 98% to 20 ml of acetic anhydride at −20° C., was added under nitrogen atmosphere. After 2.5 hours of stirring the reaction was stopped by addition of sodium acetate. Ethyl acetate and a saturated sodium hydrogencarbonate solution were added to the cold reaction mixture and after extraction and organic layer was washed with water, dried and concentrated. The crude product was purified by column chromatography to give 800 mg of compound 40.

Compound 40 (800 mg) was dissolved in dry tetrahydrofuran (10 ml) and piperidine (1.3 ml) was added under a nitrogen atmosphere. The mixture was stirred for 20 hours at 20° C. and subsequently diluted with ethyl acetate. The organic layer was washed with 0.3N hydrochloric acid and water and dried. After concentration of the organic layer the residue was purified by column chromatography to give 430 mg of compound 41.

To a solution of compound 41 (490 mg) in dichloromethane (5.4 ml) cesium carbonate (43 mg) and trichloroacetonitrile (0.52 ml) were added. The mixture was left for 1 hour at 20° C. After filtration the filtrate was concentrated and the residue was purified by column chromatography giving 417 mg of compound 42.

Compound 42 (317 mg) and compound 29 (243 mg) were coevaporated twice with toluene. Dichloromethane (7.1 ml) and powdered mol sieves 4Å (235 mg) were added and the mixture was cooled to −20° C. At this temperature a solution of trimethylsilyl trifluoromethanesulfonate (8.75 µl) in dichloromethane (2.8 ml) was added dropwise. After stirring for 1 hour the reaction was stopped by addition of solid sodium hydrogencarbonate. The mixture was stirred for another 15 min, filtered and concentrated. After purification by column chromatography 372 mg of compound 43 was obtained.

Compound 43 (370 mg) was dissolved in pyridine (1.2 ml). A mixture of pyridine (1.2 ml), acetic acid (1.56 ml) and hydrazine hydrate (0.18 ml) was added at 20° C. and the mixture was stirred for 7 min. After dilution with water and extraction with ethyl acetate the organic layer was washed with a sodium hydrogencarbonate solution and water, dried and purified by column chromatography to give 324 mg of compound 44.

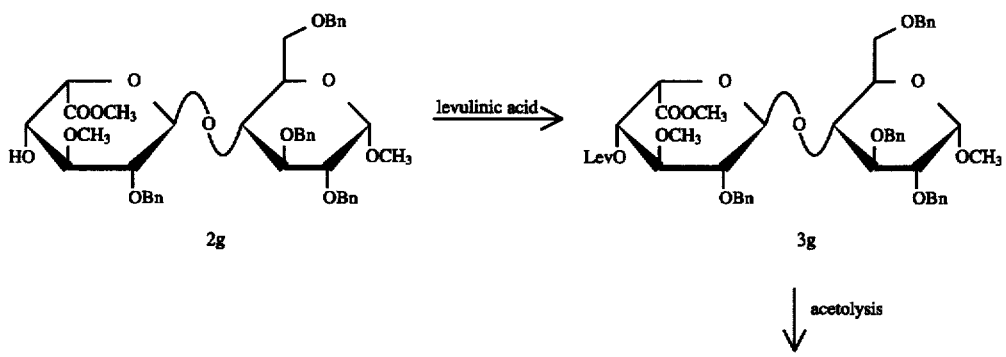

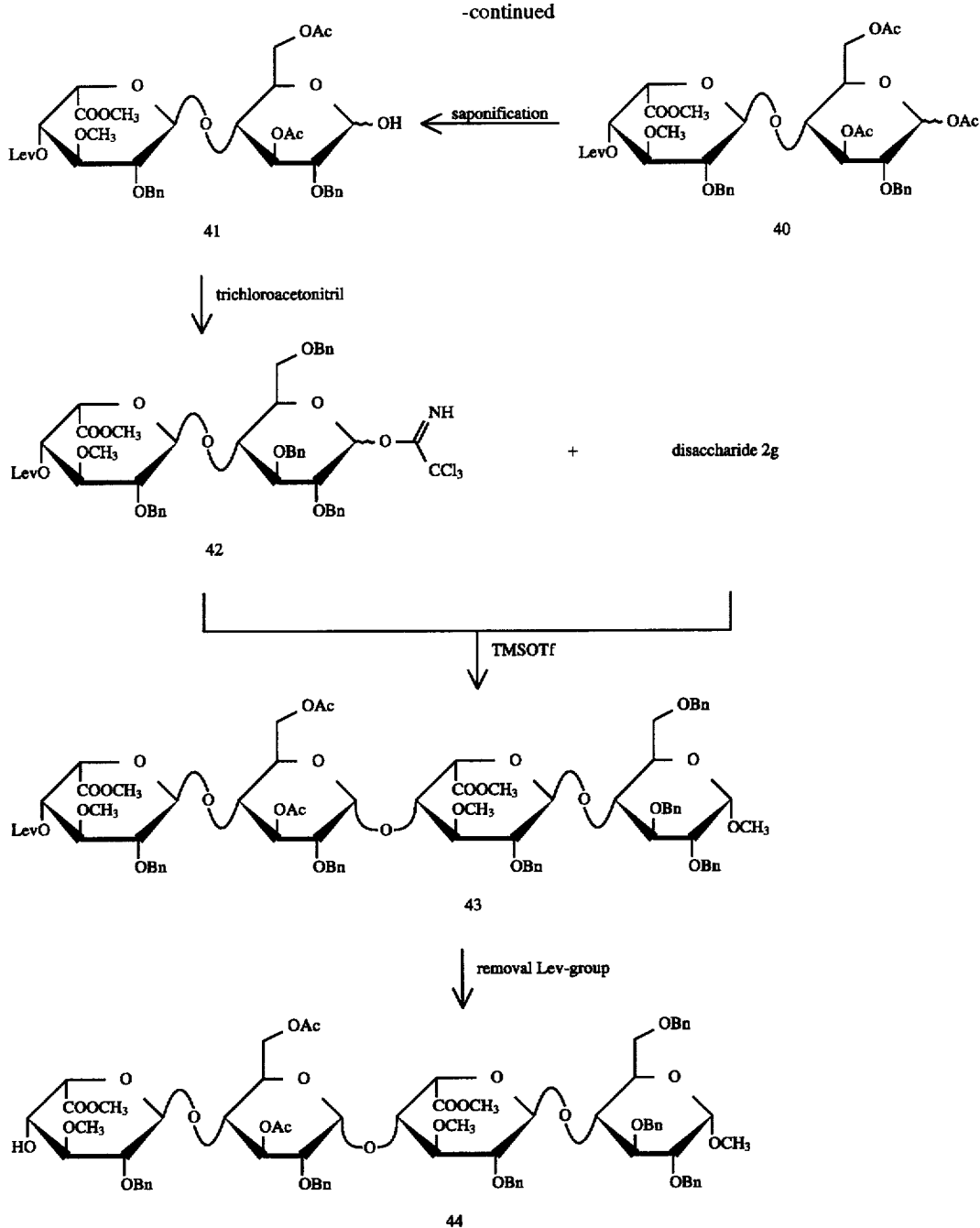

EXAMPLE 5

Preparation of active ester 52

Tetraethylene glycol 45 (10 g) was dissolved in dry tetrahydrofuran (150 ml) and sodium hydride (60% dispersion in mineral oil, 1.64 g), was added in small portions at 0° C. After 1 hour of stirring a solution of tert.-butyldimentylsilyl chloride (6.18 g) in tetrahydrofuran (20 ml) was added and the mixture was stirred for 15 min. After 10 min of stirring the mixture was diluted with water and extracted with ethyl acetate. The organic extract was dried and concentrated. Column chromatography of the crude product gave 6 g of compound 46.

Compound 46 (5.0 g) was dissolved in tetrahydrofuran (80 ml) and tert. butyl bromoacetate (26.2 ml) was added. The mixture was stirred at 50° C. and sodium hydride (1.16 g) was added in small portions under a nitrogen atmosphere. After one hour of stirring the mixture was worked up in the same manner as described for compound 46. Column chromatography of the residue yielded compound 46 (5 g).

A solution of compound 47 (3.1 g) in a mixture of acetic acid (25 ml), water (8.3 ml) and tetrahydrofuran (8.3 ml) was stirred for 24 hours at 20° C. The mixture was neutralised with sodium hydroxide solution, diluted with water and extracted with ethyl acetate. The combined extracts were dried and concentrated. The crude product was filtered on a column of silica gel to give 1.52 g of compound 48.

Compound 48 (1.4 g) was dissolved in dichloromethane (12.7 ml). Pyridine (7.7 ml) and p-toluenesulfonyl chloride (1.3 g) were added and the mixture was stirred for 20 hours at 20° C. After dilution with water the mixture was extracted with dichloromethane.

added at room temperature. After 4 hours of stirring the mixture was diluted with toluene and evaporated. The residue was coevaporated three times with toluene. Column chromatography of the crude product gave 91 mg of compound 51.

Compound 51 (29.1 mg) was dissolved in dry dimethylformamide (1.5 ml) and N,N-diisopropylethylamine (12.8 µl) was added. O-(N-succinimidyl)-N,N,N',N'-

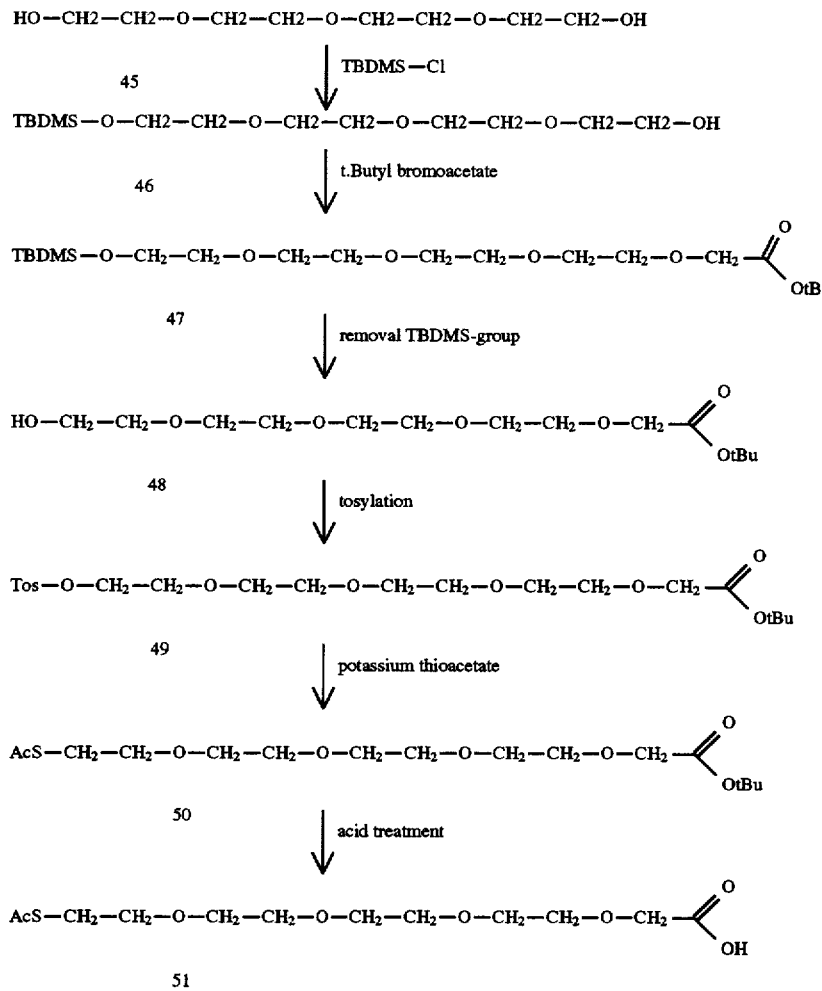

Conventional work-up and column chromatography of the crude product yielded 1.5 g of compound 49.

To a solution of compound 49 (570 mg) in acetone (20 ml) was added potassium thioacetate (350 mg). The solution was left at 20° C. for 1 hour. The mixture was diluted with water and extracted with ethyl acetate. After evaporation of the organic layer and filtration on a column of silica gel 440 mg of compound 50 was isolated.

Compound 50 (120 mg) was dissolved in dichloromethane (1.5 ml) and trifluoroacetic acid (0.20 ml) was tetramethyluronium tetrafluoroborate (22.3 mg) was added under a nitrogen atmosphere and the mixture was stirred for 1.5 hours. This stock-solution of active ester 52 was used for spacer elongation of compound 54.

For the preparation of compound 54 the procedure of example 3 for the preparation of compound 34 was followed, the only difference being the use tetrasaccharide 53 instead of compound 31:

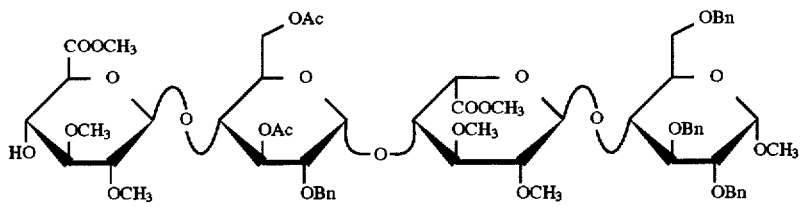

Compound 53 was prepared analogously to the procedures described by H. Lucas et al., Angew. Chem. 1993, 32(3), 434–436. In this reference the preparation of a tetrasaccharide (12) is depicted in Scheme 2. For the preparation of compound 53 step d) of Scheme 2 was adapted: a methyl group was introduced instead of a benzyl group by the use of $CH_3I$ instead of BnBr. Further reaction steps for the preparation of 53 were similar to the preparation of tetrasaccharide 12 of said reference.

Compound 54 (52 mg) was dissolved in a mixture of dimethylformamide (150 μl) and water (150 μl). 4-Methylmorpholine (50 μl) was added and after 5 min of stirring the the stock-solution of active ester 52 was added. After 1 hour of stirring the mixture was evaporated and the residue was purified on a Rp-18 column (water:methanol= 7:3 v/v) to give 48 mg of compound 55.

Compound 55 (48 mg) was coevaporated twice with dimethylformamide, dried and dissolved in dry dimethylformamide (2.1 ml). Triethylamine sulfurtrioxide (312 mg) was added under a nitrogen atmosphere and the mixture was stirred overnight at 50° C., after which an aqueous solution of sodium hydrogencarbonate was added. The mixture was stirred for 1 hour at room temperature, concentrated to a small volume and desalted on a Sephadex G-25 column. The isolated product was eluted with water on a Dowex WX8 $Na^+$ column to give 73 mg of a sulfated pentasaccharide derivative. This compound was treated with 0.2N hydrochloric acid solution (2.0 ml). After neutralisation the mixture was desalted on a Sephadex G-25 column to give 57 mg of compound 56.

Compound 56 (50 mg) was dissolved in 10.7 of a hydroxylamine solution in buffer. (To obtain this solution hydroxylamine.hydrochloric acid salt (174 mg) was dissolved in 100 ml of a 0.1M sodium dihydrogenphosphate solution and the pH was adjusted to 7.5 with a 4N sodiumhydroxide solution.) The reaction mixture was stirred for 90 min at 20° C., then the pH was brought to 8.5 and the mixture was stirred for another 24 hours. After desalting and purification of the mixture on a Sephadex G-50 column 40 mg of pure bisconjugate V was isolated. $[\alpha]^{20}_D=+42.9°$ (c=1; water)

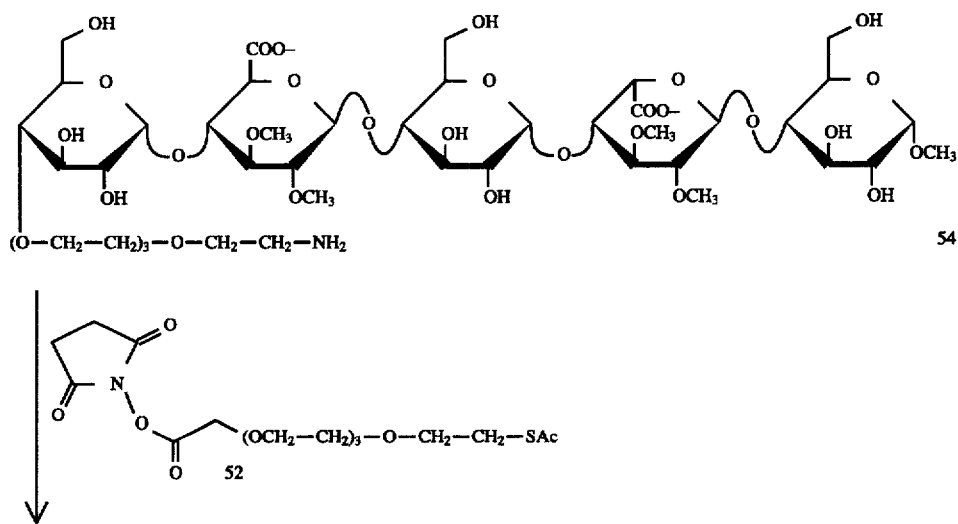

-continued
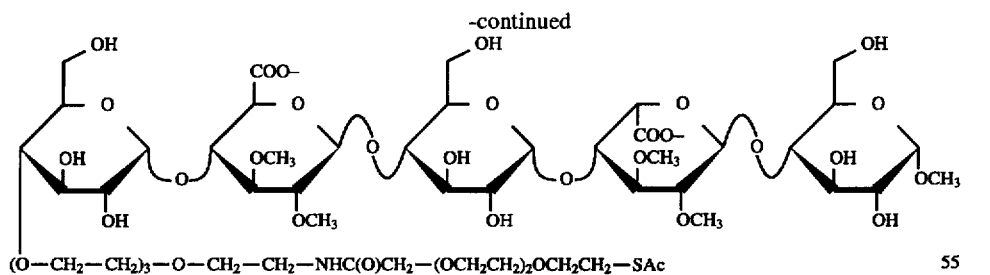
55
↓ sulfation
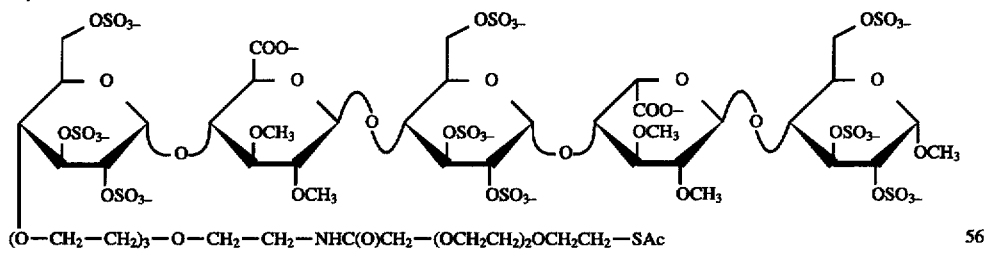
56
↓ hydroxylamine treatment
bisconjugate V
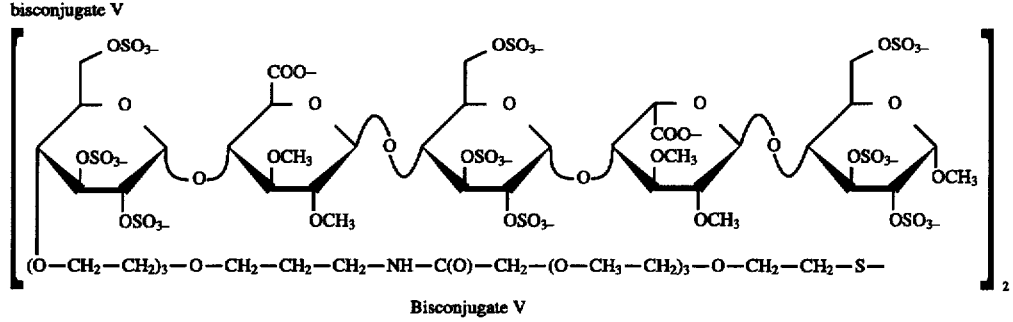
Bisconjugate V
EXAMPLE 6
Bisconjugate VI was prepared in a manner analogous to that described for bisconjugate V, the only difference being the use of tetrasaccharide 57 (which is tetrasaccharide 12 of H. Lucas et al., Angew. Chem. 1993, 32(3), 434–436) instead of compound 53. $[\alpha]^{20}_D = +31.6°$ (c=0.82; water)
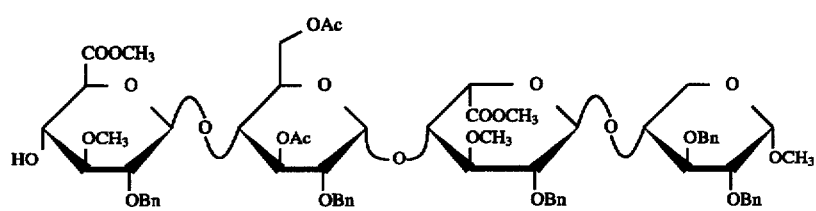
57

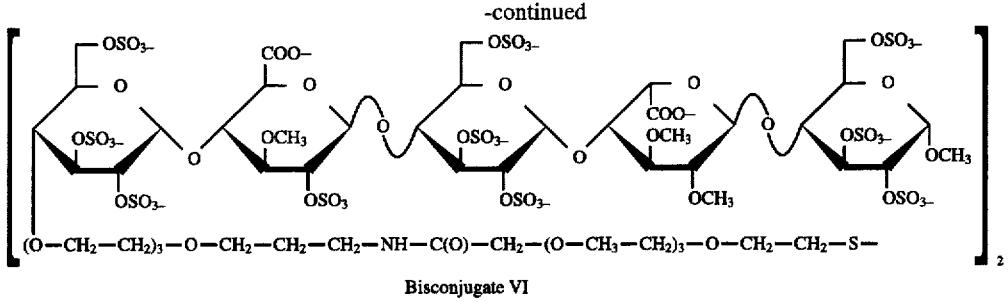

Bisconjugate VI

EXAMPLE 7

For the preparation of bisconjugate VII the procedure of example 5 was followed, the difference being that instead of monoconjugate 54 compound 89 was used. Compound 89 was prepared according to the procedure for the preparation of compound 34 (as described in example 3), using compound 60 instead of monosaccharide 24. $[\alpha]^{20}_D = +66.6°$ (c=0.5 water)

16 hours and the excess of sodium hydride was destroyed with methanol. Water was added and the mixture was extracted with ethyl acetate. After concentration 25 g of compound 59 was isolated. Compound 59 (44 g) was dissolved in dichloromethane (90 ml) and triethylsilane (92 ml) was added. A mixture of trifluoroacetic acid (44 ml) and trifluoroacetic anhydride (0.9 ml) was added dropwise and trifluoroacetic anhydride (0.9 ml) was added dropwise and

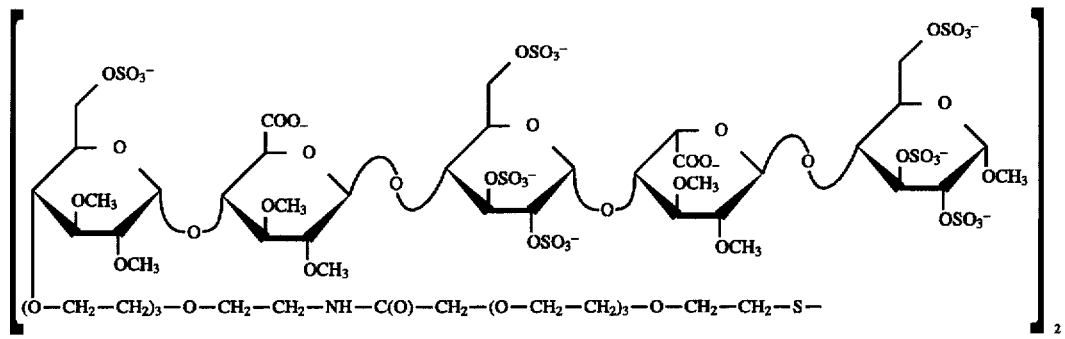

Bisconjugate VII

Preparation of compound 60:

Compound 58 (29 g) and iodomethane (15.5 ml) were dissolved in dimethylformamide (50 ml). The solution was added dropwise to a suspension of sodium hydride (10.5 g) in dimethylformamide at 20° C. The mixture was stirred for the mixture was stirred for 1 hour at 20° C. The reaction was quenched with a cold sodium hydrogencarbonate solution, extracted with ethyl acetate, dried and concentrated. Silica gel chromatography of the residue yielded 31 g of compound 60.

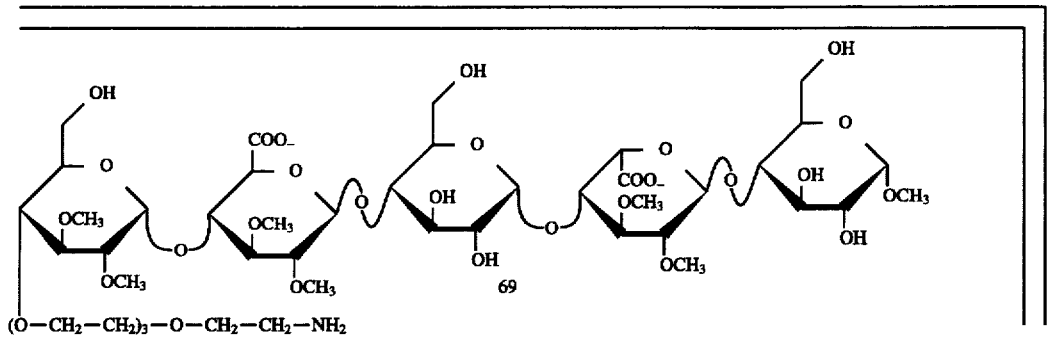

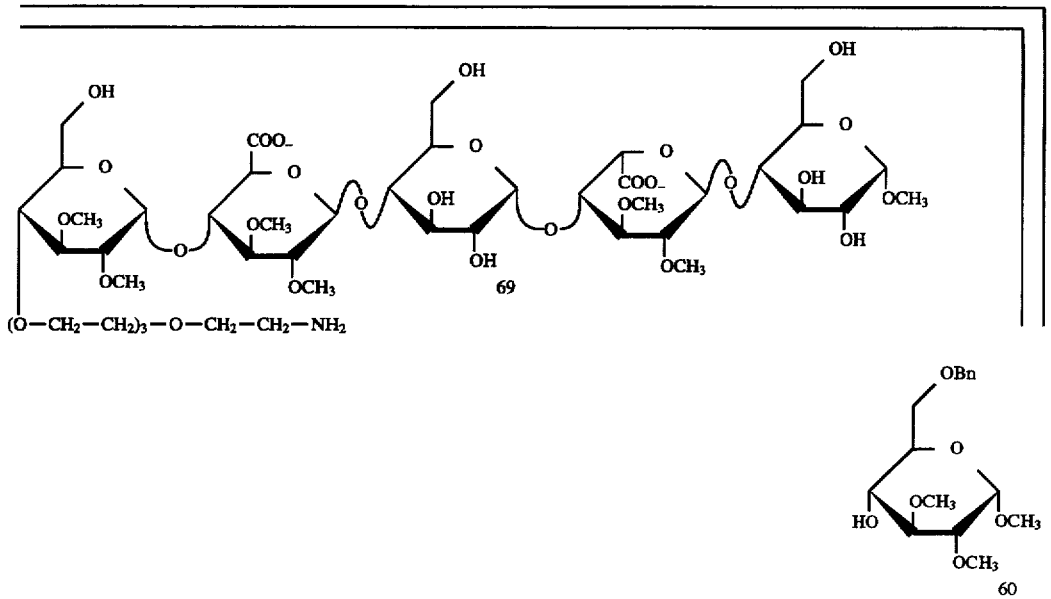

EXAMPLE 8

Monosaccharide 69 was prepared as follows:

To a solution of 1,6-anhydromannose 61 (19.1 g) in acetone (75 ml) and 2,2-dimethoxypropane (75 ml), camphorsulfonic acid (200 mg) was added. The reaction mixture was stirred overnight. Triethylamine was added and the solvent was evaporated. Dichloromethane was added to the residue, salts were filtered off and the filtrate was evaporated to dryness. Column chromatography of the crude product yielded 15 g of compound 62.

Compound 62 (3.0 g) and tetraethylene glycol di-p-tosylate were dissolved in dry tetrahydrofuran (250 ml). The mixture was heated to 60° C. and sodium hydride (900 mg) was added under nitrogen atmosphere. After 30 min of stirring the mixture was concentrated and purified by column chromatography to give 3.9 g of crude compound 63.

Compound 63 (3.9 g) was dissolved in tetrahydrofuran (25 ml) and N-methylbenzylamine (1.95 ml) was added. The mixture was heated to reflux temperature for 30 min and concentrated to give 5.0 g of crude compound 64.

Crude compound 64 (5.1 g) was dissolved in 30 ml of methanol:1N hydrochloric acid 9:1 (v/v) and the mixture was stirred for 5 hours at 85° C. After cooling, pyridine (50 ml) was added and the solution was concentrated to give crude compound 65.

Crude compound 65 was dissolved in 75 ml of pyridine:acetic anhydride 2:1 (v/v); 4-dimethylaminopyridine (25 mg) was added and the mixture was stirred for 4 hours at room temperature. The mixture was diluted with toluene and evaporated. The residue was dissolved in ethyl acetate and diluted hydrochloric acid was added. After extraction the acid water layer was brought to pH 10 with sodium hydroxide solution and extracted again with ethyl acetate. The organic layer was dried and concentrated. The crude product was purified by column chromatography to give 1.86 g of compound 66.

Compound 66 (1.86 g) was dissolved in a mixture of acetic anhydride (45 ml) and trifluoroacetic acid (3.8 ml). The solution was stirred for 60 hours at 20° C. and was then diluted with toluene. After concentration the residue was dissolved in ethyl acetate and washed with sodium hydrogencarbonate. The organic layer was dried and concentrated. Column chromatography of the crude product gave 0.5 g of compound 67.

Compounds 68 and 69 were prepared according to the manner as described in example 3 for compounds 27 and 28, respectively.

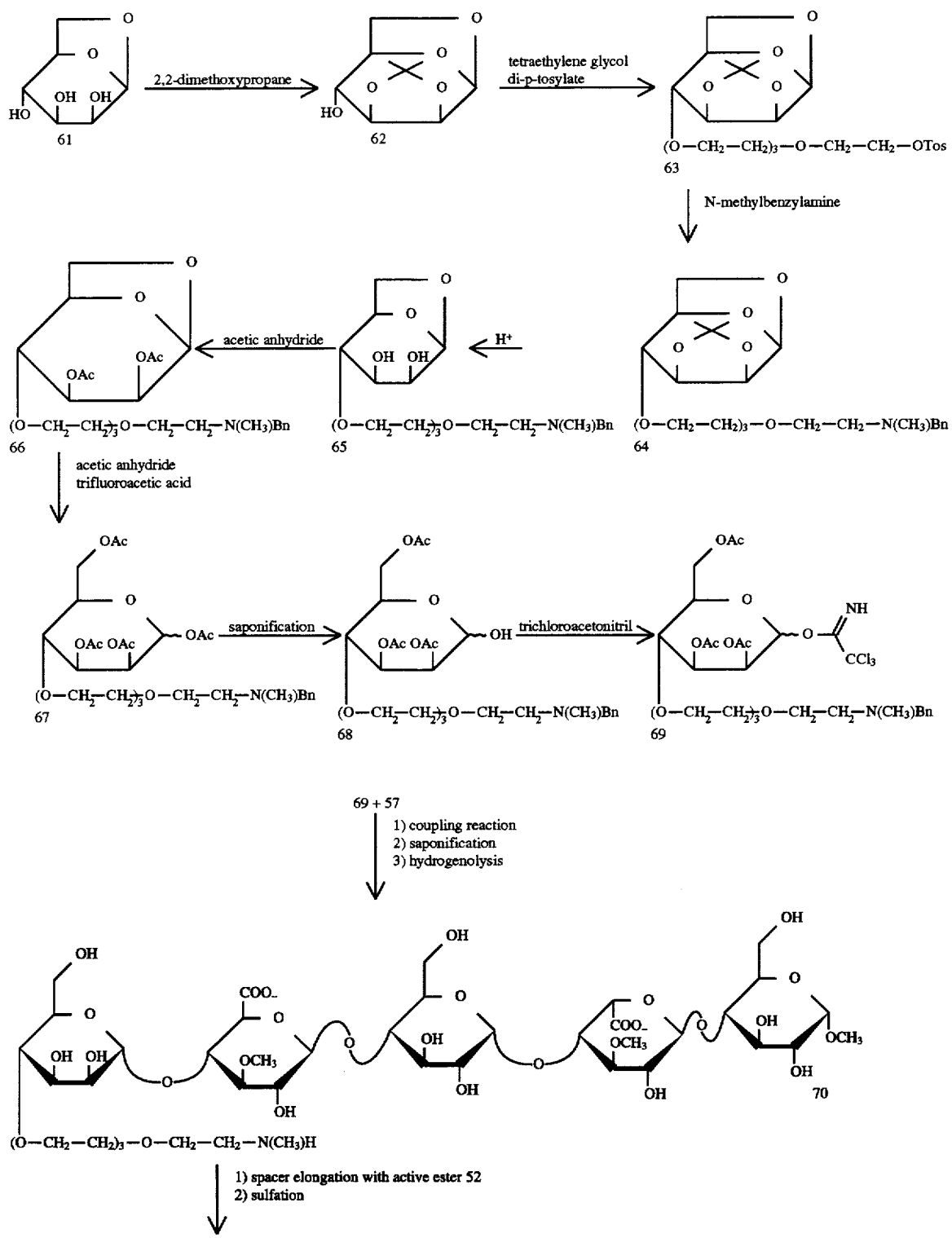

-continued

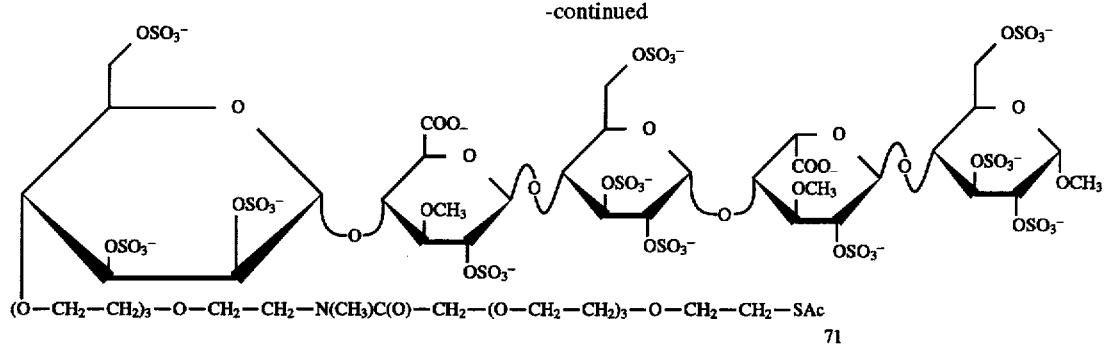

Bisconjugate VIII

Compound 69 was coupled with tetrasaccharide 57, followed by saponification and hydrogenolysis (as described in example 3 for compounds 32, 33 and 34, respectively) after which compound 70 was obtained.

Compound 70 was treated with active ester 52, followed by sulfation (according to the preparations of compounds 55 and 56, example 5), giving compound 71.

Compound 71 was treated with hydroxylamine (according to the preparation of bisconjugate V from compound 56, example 5) to form bisconjugate VIII. $[\alpha]^{20}_D = +27.3°$ (c=1; water)

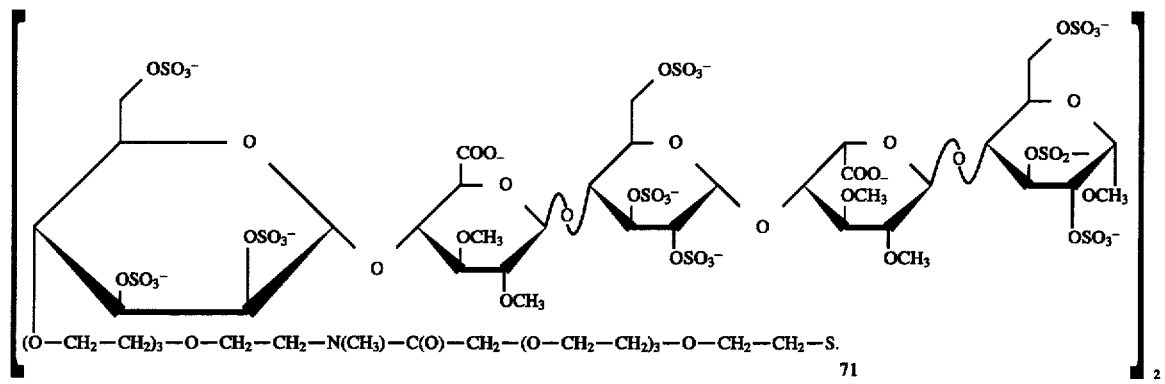

EXAMPLE 9

Bisconjugate IX was prepared according to the procedure of example 4, differing at one point; instead of glucopyranosyl imidate 28 and analogue of mannopyranosyl imidate 69 was used, having —$N_3$ at the end of the tetraethylene glycol side chain instead of —$N(CH_3)Bn$. The —$N_3$ containing compound was prepared by reacting compound 63 with lithium azide instead of N-methylbenzylamine. All other reaction steps towards the azide containing mannopyranosyl imidate were similar to the synthesis of 69. $[\alpha]^{20}_D = +33.2°$ (c=0.25; water)

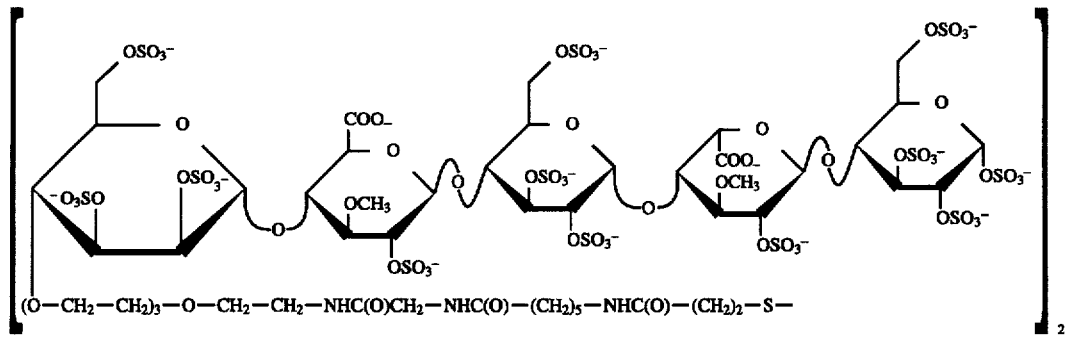

Bisconjugate IX

EXAMPLE 10

For the preparation of bisconjugate X the procedure of example 9 was followed, the difference being the use of tetrasaccharide 53 instead of tetrasaccharide 57 in the preparation of the pentasaccharide moiety. $[\alpha]^{20}_D=+26.5°$ (c=1; water)

romethanesulphonate in dichloromethane were added. The reaction mixture was stirred for 15 minutes and then filtered over celite, subsequently washed with an aqueous sodium hydrogencarbonate solution and water and evaporated to dryness. The residue was subjected to acetolysis by dissolving it in a mixture of trifluoroacetic acid and acetic anhy-

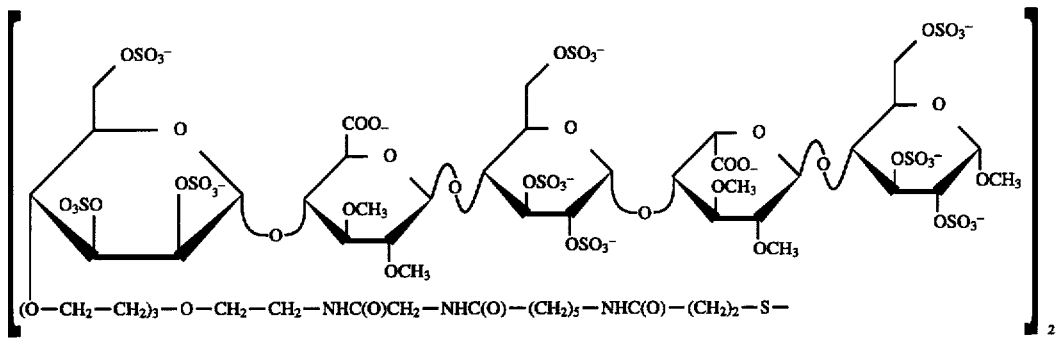

Bisconjugate X

EXAMPLE 11

Bisconjugated XI was prepared from compound 75 according to the conversion of compound 32 into bisconjugated III (example 3), the difference being the application of succinimido N-(benzyloxycarbonyloxy) glycine instead of N-(benzyloxycarbonyloxy) succinimide. $[\alpha]^{20}_D=+25.7°$ (c=0.49; water)

dride. The reaction product was treated with benzylamine in diethyl ether and thereafter with trichloroacetonitrile in dichloromethane in the presence of potassium carbonate, to obtain compound 73 (yield: 50%).

0.121 mmol of compound 73 and 0.093 mmol of compound 74 (see EP 529715, Preparation IX) were dissolved in 3.2 ml of dichloromethane. In the presence of molecular

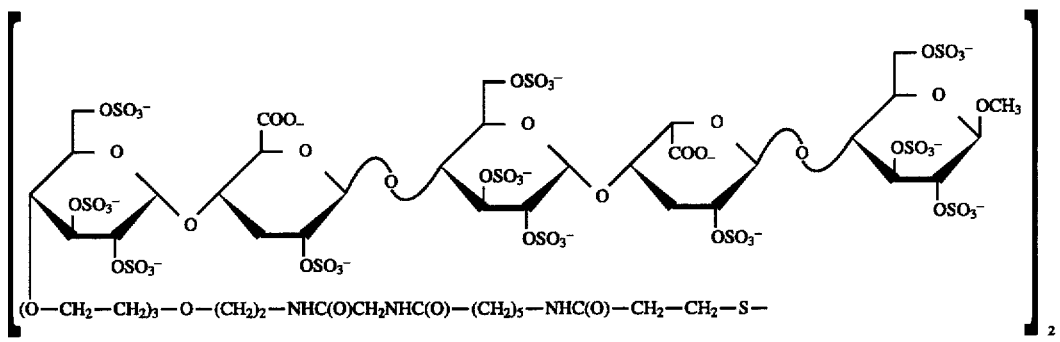

Bisconjugate XI

Preparation of compound 75

214 mmol of compound 28 and 178 mmol of compound 72 (see EP 529715, Preparation V) were dissolved in 4 ml of dichloromethane at room temperature, and 160 mg of molecular sieves 4 Å were added. This mixture was stirred for 1 hour. The mixture was then cooled to –20° C. and 21.4 mmol of a 40 mM solution of trimethylsilyl trifluosieves and under an argon atmosphere the mixture was cooled to –20° C., and then 0.470 ml of a solution of trimethylsilyl trifluoromethanesulphonate in dichloromethane were added. The reaction mixture was stirred at –20° C. for 1 hour, after which it was filtered, washed with water, evaporated and purified on a Sephadex LH-20 column and then on a silica column, to obtain of compound 75 (62%).

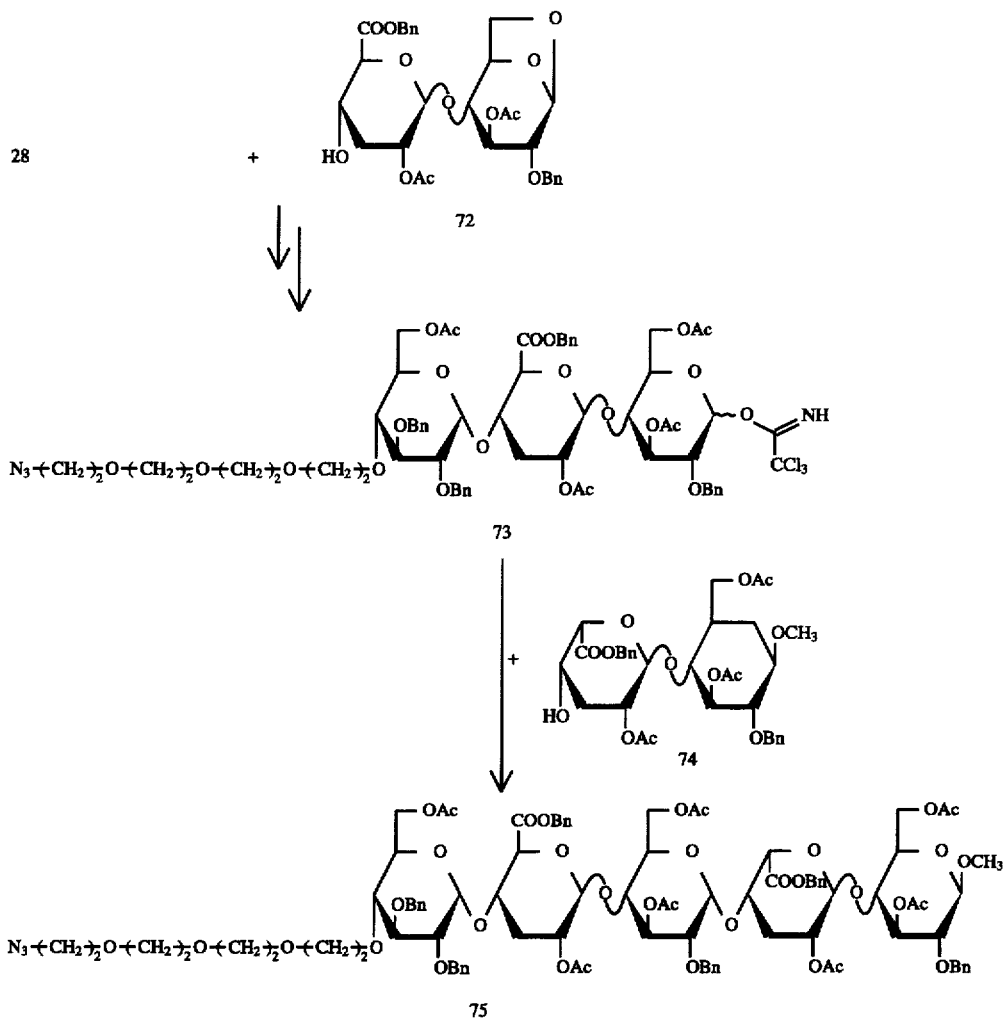

EXAMPLE 12

Maltophentaose 76 (500 mg) was dissolved in 15 ml of pyridine:acetic anhydride=2:1 (v/v), stirred overnight and concentrated. After coevaporation with toluene 930 mg of compound 77 was obtained.

The reactions 77→78→79 were performed following the procedures as described for the conversion of 26→27→28 and the subsequent coupling reaction resulting in compound 80 was carried out according to the procedure as described for the coupling reaction of compounds 28 and 31 (see example 3).

Compound 80 (300 mg) was dissolved in dry methanol and a small quantity of potassium tert. butoxide was added. The mixture was stirred overnight. Dowex H⁺ was added to neutralise the mixture and after filtration the filtrate was concentrated to give 180 mg of compound 81.

Compound 81 was sulfated according to the procedure as described for compound 35 (example 3), forming compound 82. After hydrogenolysis of compound 82 according to the procedure as described for the conversion of compound 16 into 17 (see example 1), compound 83 was obtained.

Preparation of asymmetric bisconjugate XII

Solution A

Compound 83 (42 mg) was dissolved in a mixture of 0.1M sodium dihydrogen phosphate buffer pH 7.5 (1.3 ml) and dimethylformamide (0.5 ml) and sulfosuccinimidyl 4-(p-maleimidophenyl)butyrate (7 mg) was added. The mixture was stirred for 15 min.

Reaction mixture B

The monoconjugate 71 (17.5 mg) was dissolved in 1.7 ml of a 50 mMol hydroxylamine solution in 0.1M sodium dihydrogen phosphate buffer pH 7.5 under an argon atmosphere. The mixture was stirred for 1 hour giving a solution of compound 84. To this solution 1 equivalent of solution A was added under an argon atmosphere. The mixture was stirred for another 2 hours. During this process also symmetric bisconjugate was formed, which was removed by dithiothreitol treatment. After 30 min of stirring the mixture was purified on a Sephadex G-50 column to give 4.7 mg of asymmetric bisconjugate XII. $[\alpha]^{20}_D = +40.3°$ (c=0.38; water)

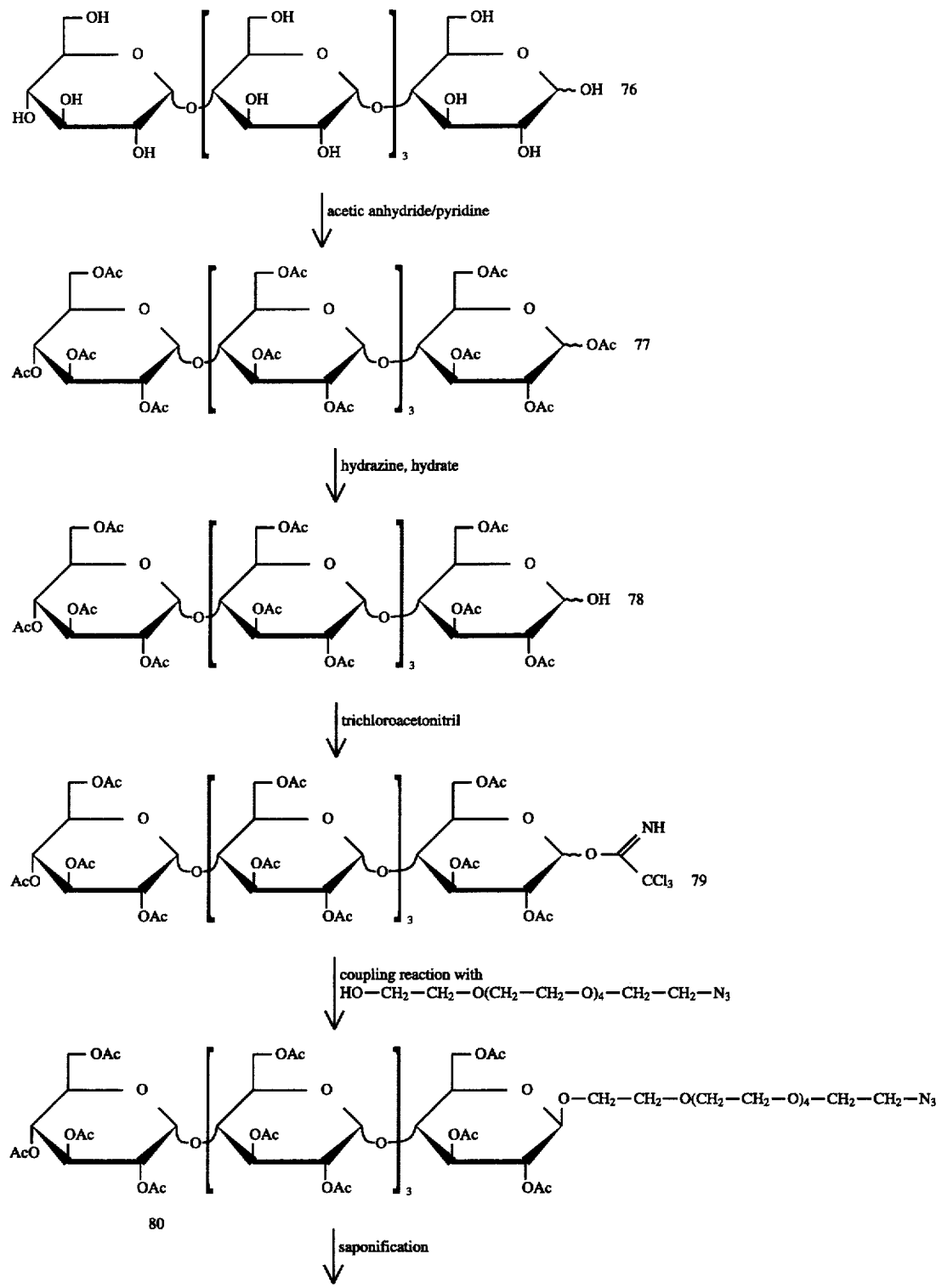

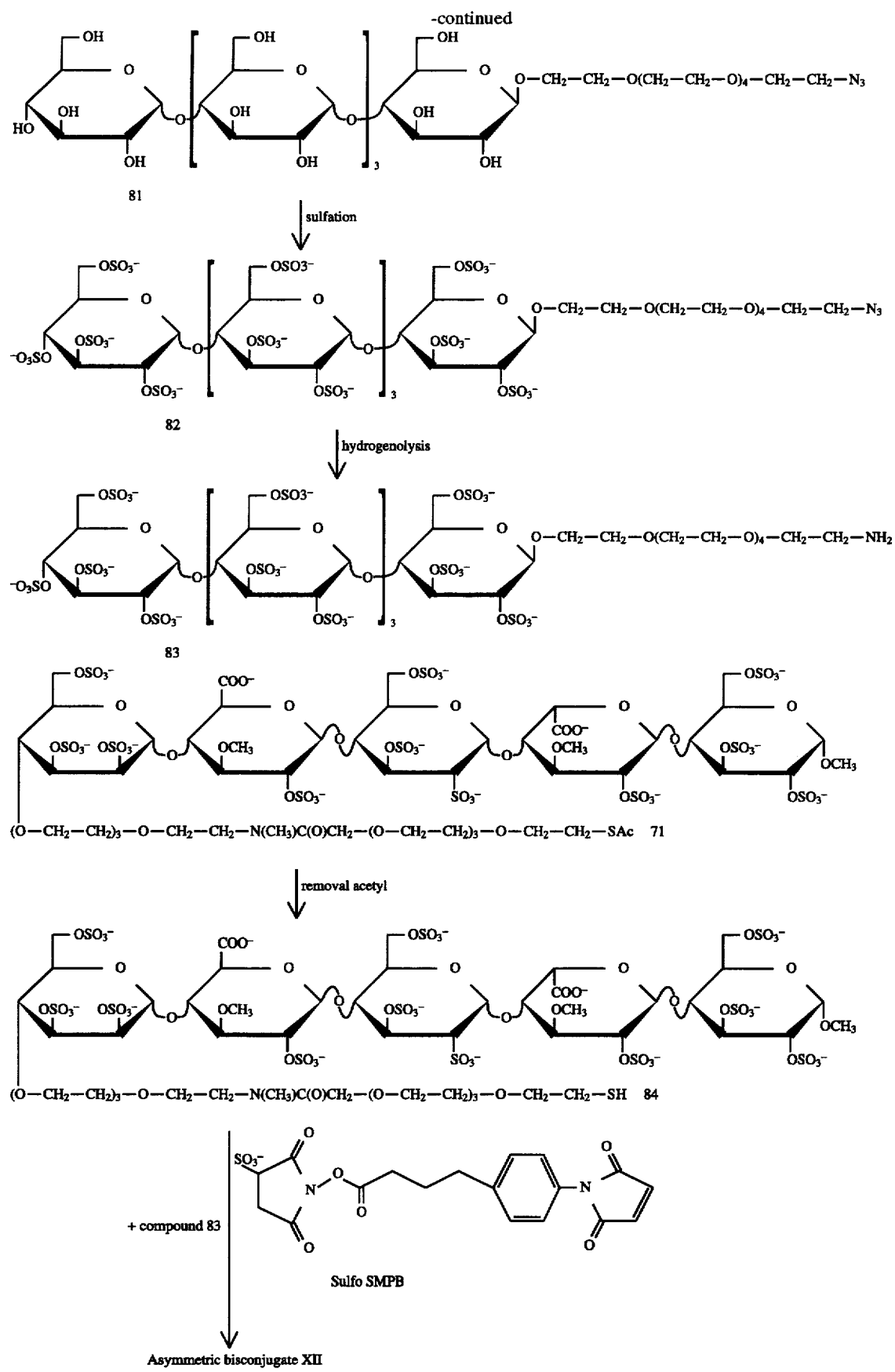

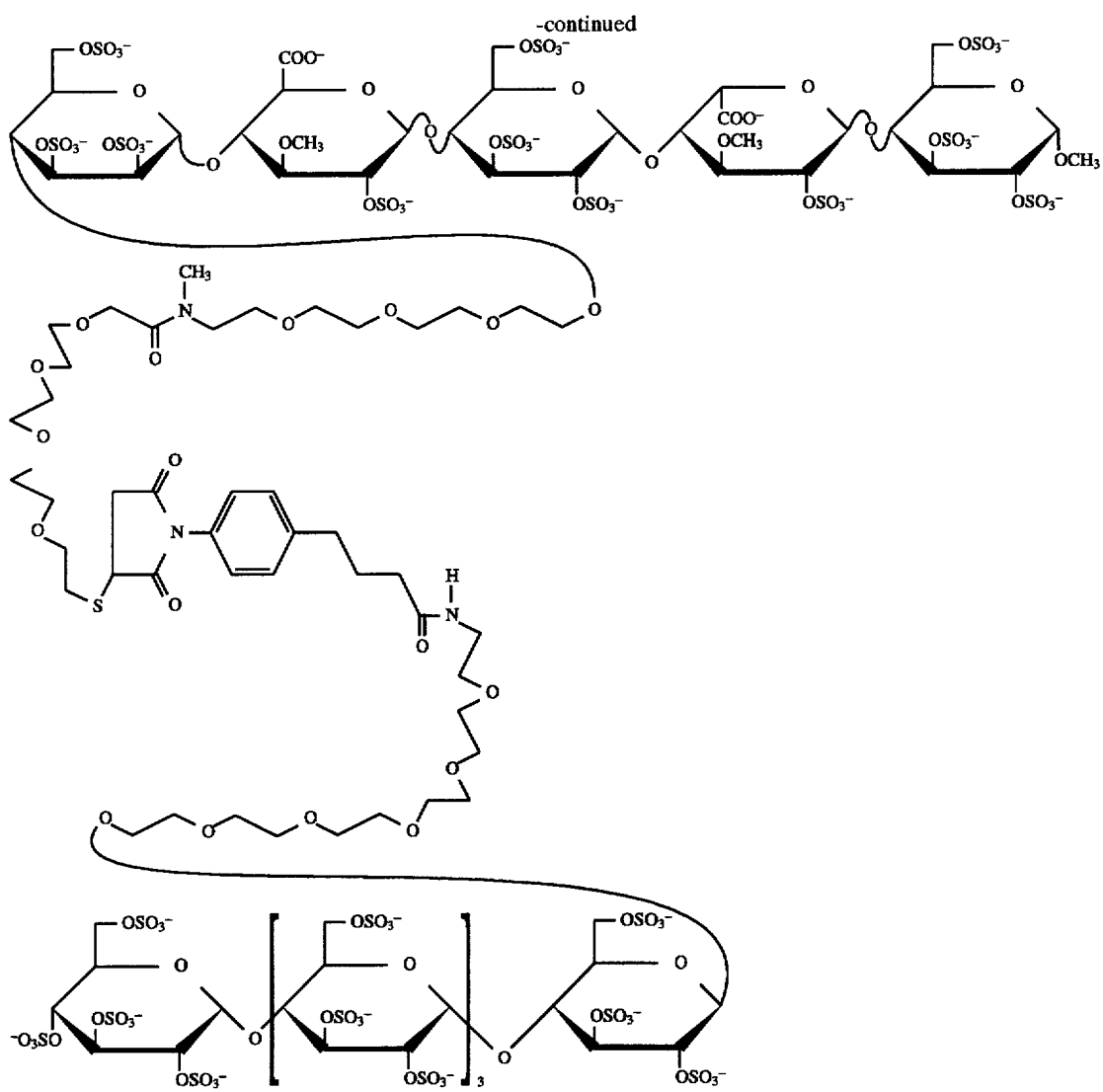

EXAMPLE 13

Asymmetric bisconjugate XIII was prepared according to the procedure as described for the preparation of bisconjugate XII. Instead of pentasaccharide 71 the analogous compound 85 was used. Compound 85 was obtained from the conversion of compound 89 by spacer elongation with active ester 52 and sulfation, as described for the conversion of 54 into 56 (see example 5). Compound 89 was mentioned in example 7. $[\alpha]^{20}_D = +65.4°$ (c=0.09; water)

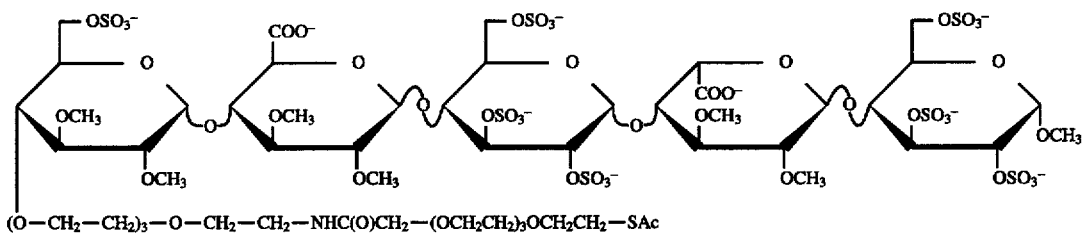

85
Asymmetric bisconjugate XIII

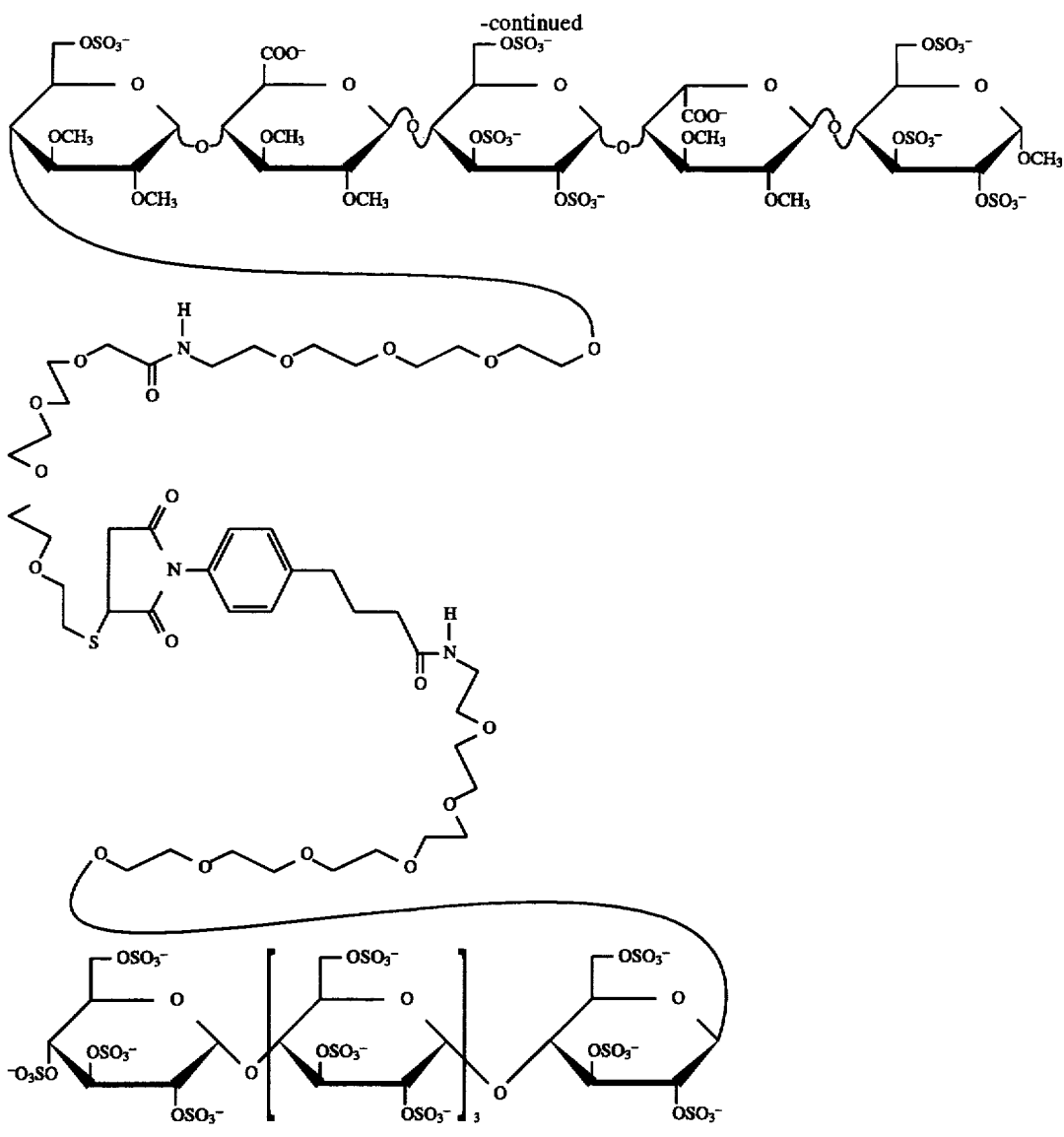

EXAMPLE 14

The sulfated maltotrioside 87 was prepared from compound 86 according to the procedure as described for the preparation of maltopentaoside 83 from compound 76 (see example 12).

Reaction A: Compound 87 (25 mg) was dissolved in 1.0 ml of 0.1M sodium dihydrogen phosphate buffer pH 7.5 and sulfosuccinimidyl-(4-iodoacetyl)aminobenzoate (21 mg) was added. The mixture was stirred for 30 min at 20° C. and purified on a Sephadex G-15 column giving 30 mg of product.

Reaction B: Compound 85 (15 mg) was dissolved in 1.7 ml of a 50 mMol. hydroxylamine solution in 0.1M sodium dihydrogen phosphate buffer pH 7.5 under an argon atmosphere. The mixture was stirred for 1 hour at 20° C. and purified on a Sephadex G-25 column giving 14 mg of compound 88.

The product obtained from reaction A and compound 88 were dissolved in 1 ml 0.1M sodium hydrogenphosphate buffer and stirred for 60 hours under an argon atmosphere at 4° C. The symmetric bisconjugate was removed by dithiothreitol treatment. After 30 min of stirring the mixture was purified on a Sephadex G-50 column to give 13 mg of bisconjugate XIV. $[\alpha]^{20}_D = +55.7°$ (c=0.46; water)

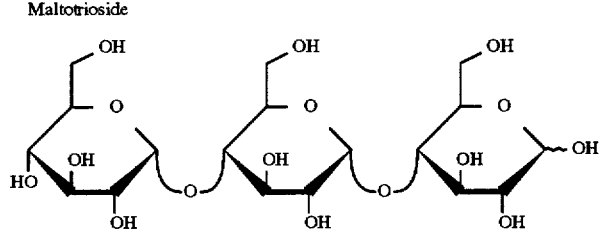
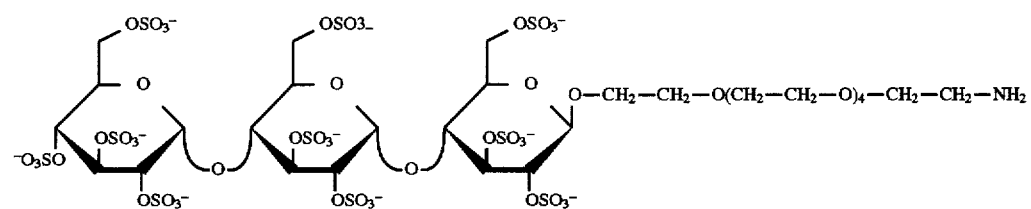
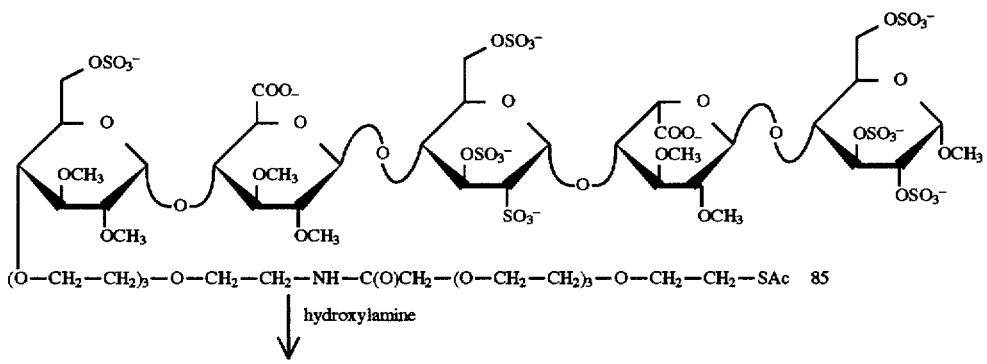

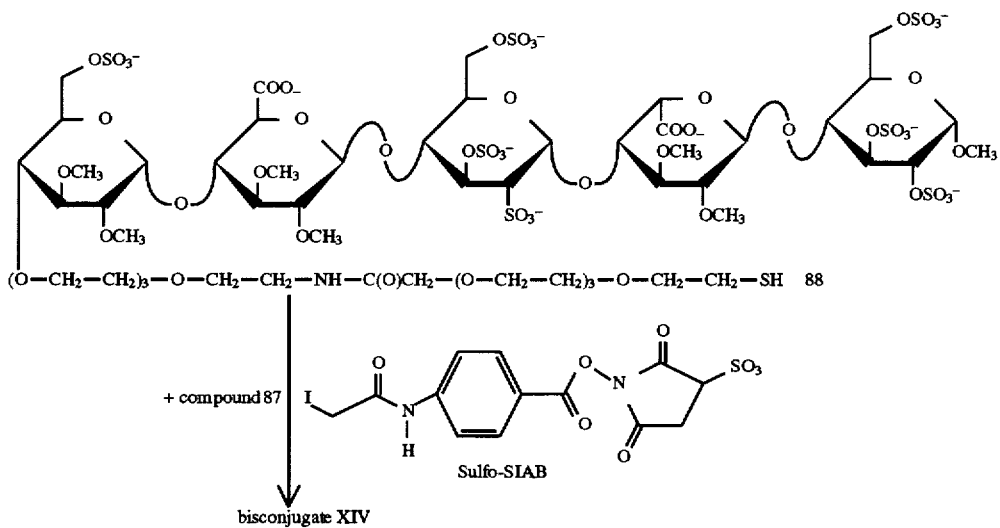
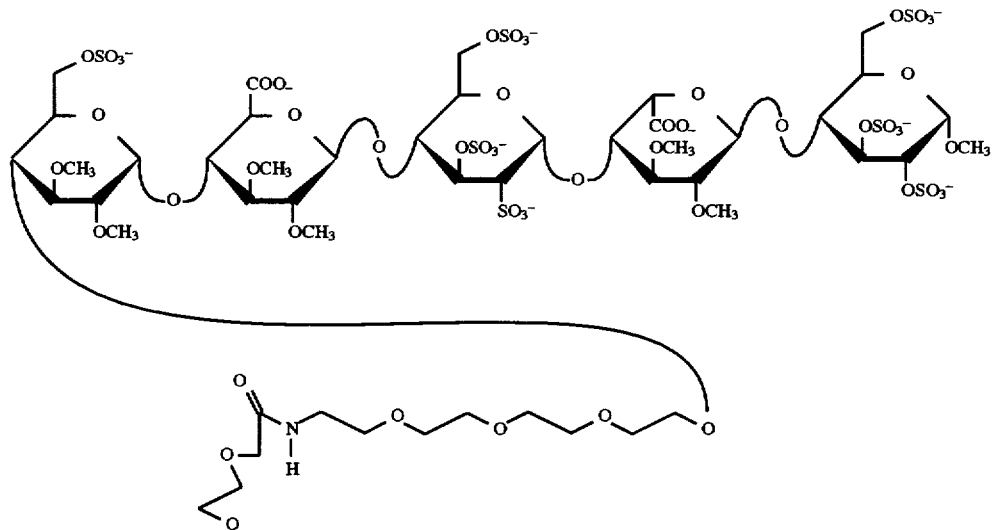

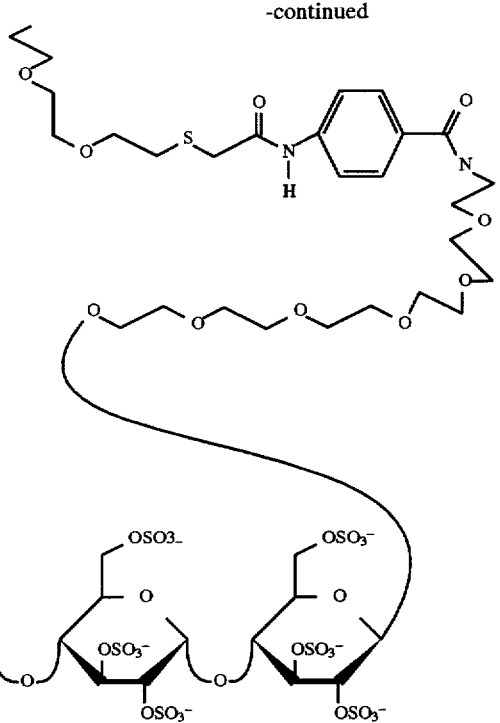

EXAMPLE 15

Asymmetric bisconjugate XV was prepared according to the procedure as described for the preparation of asymmetric bisconjugate XIV. Instead of maltotrioside 87 compound 91 was used.

The sulfated cellobiose derivative 91 was prepared from cellobiose octacetate 90 according to the procedure as described for the preparation of compound 83 from compound 77 (example 12). $[\alpha]^{20}_D=+51.2°(c=0.83;$ water)

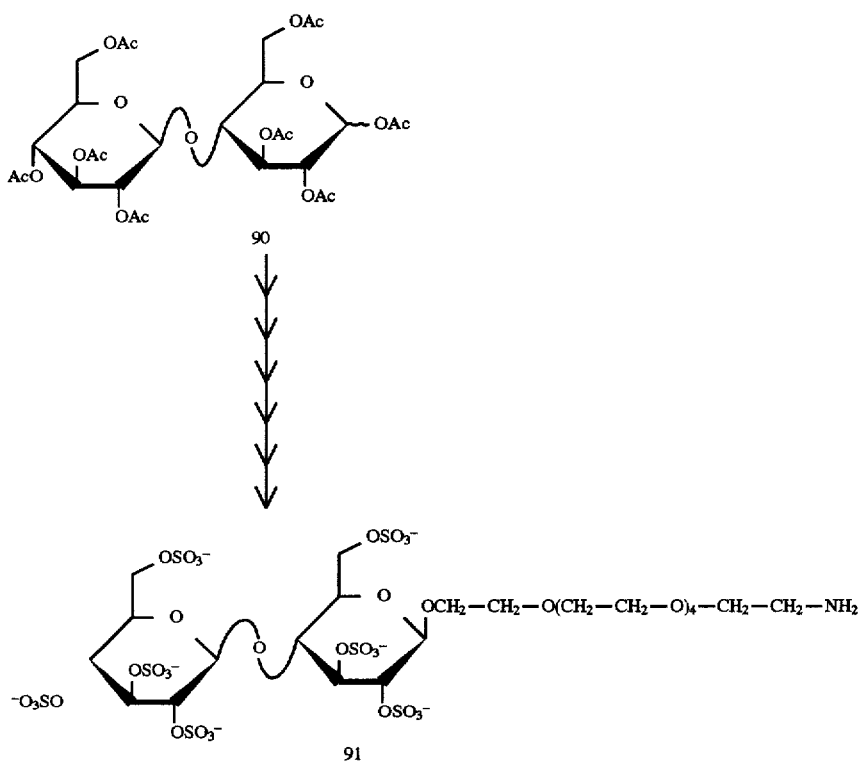

Asymmetric bisconjugate XV

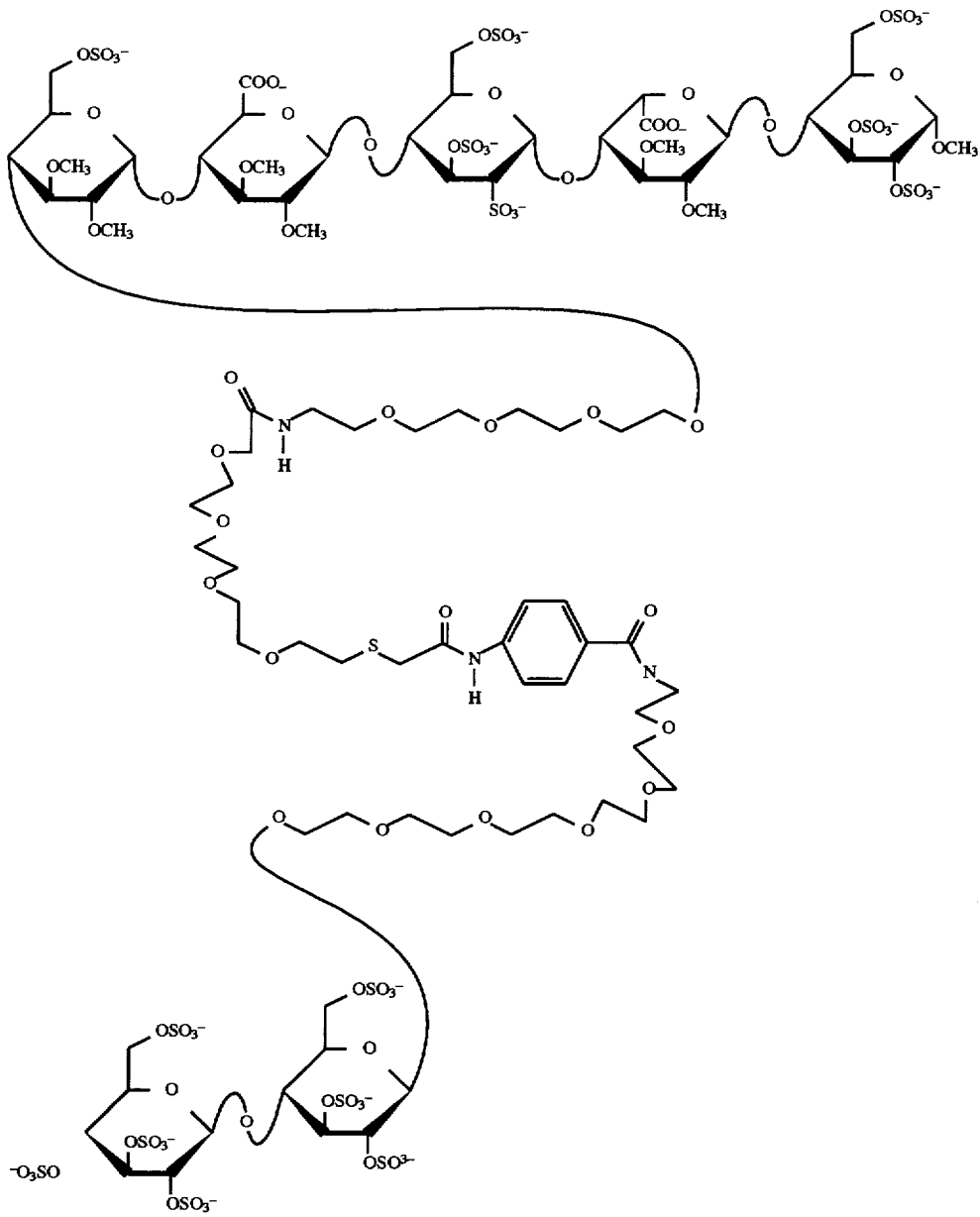

We claim:

1. A bis/mixed conjugate consisting of two saccharides and a spacer, each saccharide being the same or different and comprising two to six monosaccharide units, at least one unit being uronic acid, wherein at least one of the saccharides per se has anti-thrombotic activity, and the spacer connects at least one saccharide to the other through its non-reducing end, the chain length of the spacer consisting of at least twenty atoms.

2. The bis/mixed conjugate of claim 1, wherein at least one of the saccharides per se has affinity for at least one of AT-III and HC-II and/or has at least one activity selected from the group consisting of anti-factor IIa and anti-factor Xa activity.

3. The bis/mixed conjugate of claim 2, wherein both saccharides per se have affinity for at least one of AT-III and HC-II and/or have at least one activity selected from the group consisting of anti-factor IIa and anti-factor Xa activity.

4. The bis/mixed conjugate of claim 1, wherein at least one of the saccharides has the formula

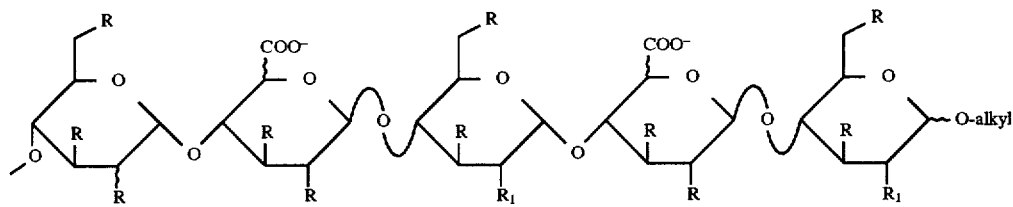

wherein each

R is independently selected from H, OH, OSO$_3^-$ and C1–C8 alkoxy;

R$_1$ is independently selected from OSO$_3^-$ and NSHO$_3^{3-}$;

and the negative charges are compensated by hydrogen or an alkali metal cation.

5. The bis/mixed conjugate of claim 1, wherein at least one of the saccharides has the formula

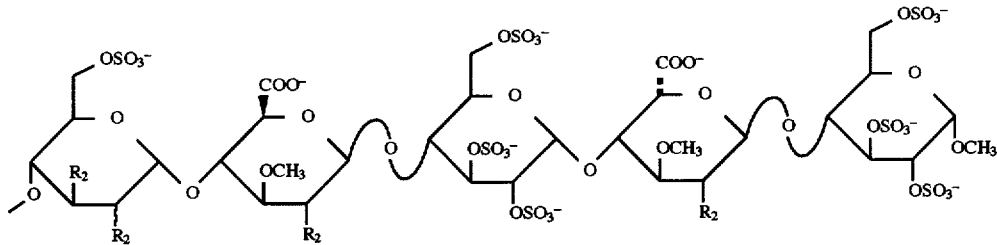

wherein R$_2$ is independently OSO$_3^-$ or OCH$_3$.

6. The bis/mixed conjugate of claim 1, wherein the spacer has the formula

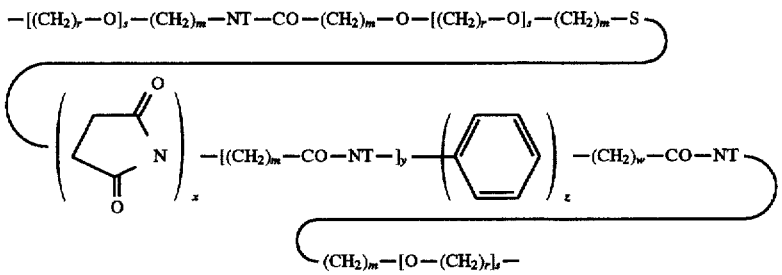

wherein one of the two free valencies of the spacer is attached to the non-reducing end of one of the saccharides and the other free valency of the spacer is attached to the reducing or non-reducing end of the other saccharide, and T is independently H or C1–C8 alkyl; m is independently 1–8; r is independently 2–4; s is independently 1–12; w is 0–10; x is 0 or 1; y is 0 or 1; z is 0 or 1, and the total number of atoms in the spacer is 20–120.

7. A pharmaceutical composition comprising the bis/mixed conjugate of claim 1 and pharmaceutically acceptable auxiliaries.

8. A method for the treatment or prevention of thrombotic disorders or smooth muscle cell proliferation comprising administering an effective amount of a composition according to claim 7.

9. The bis/mixed conjugate of claim 1, wherein the length of the spacer is from 20 to 120.

10. The bis/mixed conjugate of claim 1, wherein the spacer has the formula

or

wherein one of the two groups Q is attached to the non-reducing end of one of the saccharides and the other group Q is attached to the reducing or non-reducing end of the other saccharide, and each of the groups Q is a phenylene (C$_6$H$_4$) group or —[(CH$_2$O)$_q$—(CH$_2$)$_r$—O]$_s$—[(CH$_2$)$_r$—NT—CO]$_u$—(CH$_2$)$_v$, and T is independently hydrogen or C1–C8 alkyl; q is 0 or 1; r and t are independently 2–4; and s is 1–12; u and v are independently 1–6; n is 1–8; m is 1–8; p is 1–12; and the total number of atoms in the spacer is 20–120.

11. The bis/mixed conjugate of claim 1, wherein the spacer has the formula

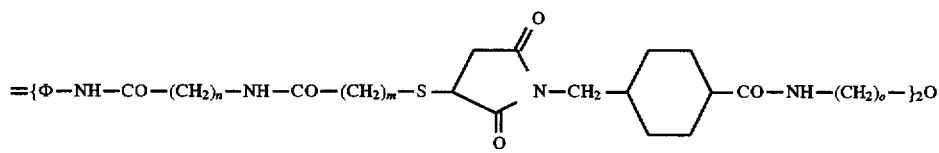
wherein
one of the two groups φ is attached to the non-reducing end of one of the saccharides and the other group φ is attached to the reducing or non-reducing end of the other saccharide, and φ denotes a phenylene ($C_6H_4$) group; n, m and o are independently 1–8; and the total number of atoms in the spacer is 20–120.
12. The bis/mixed conjugate of claim 1, which has the formula
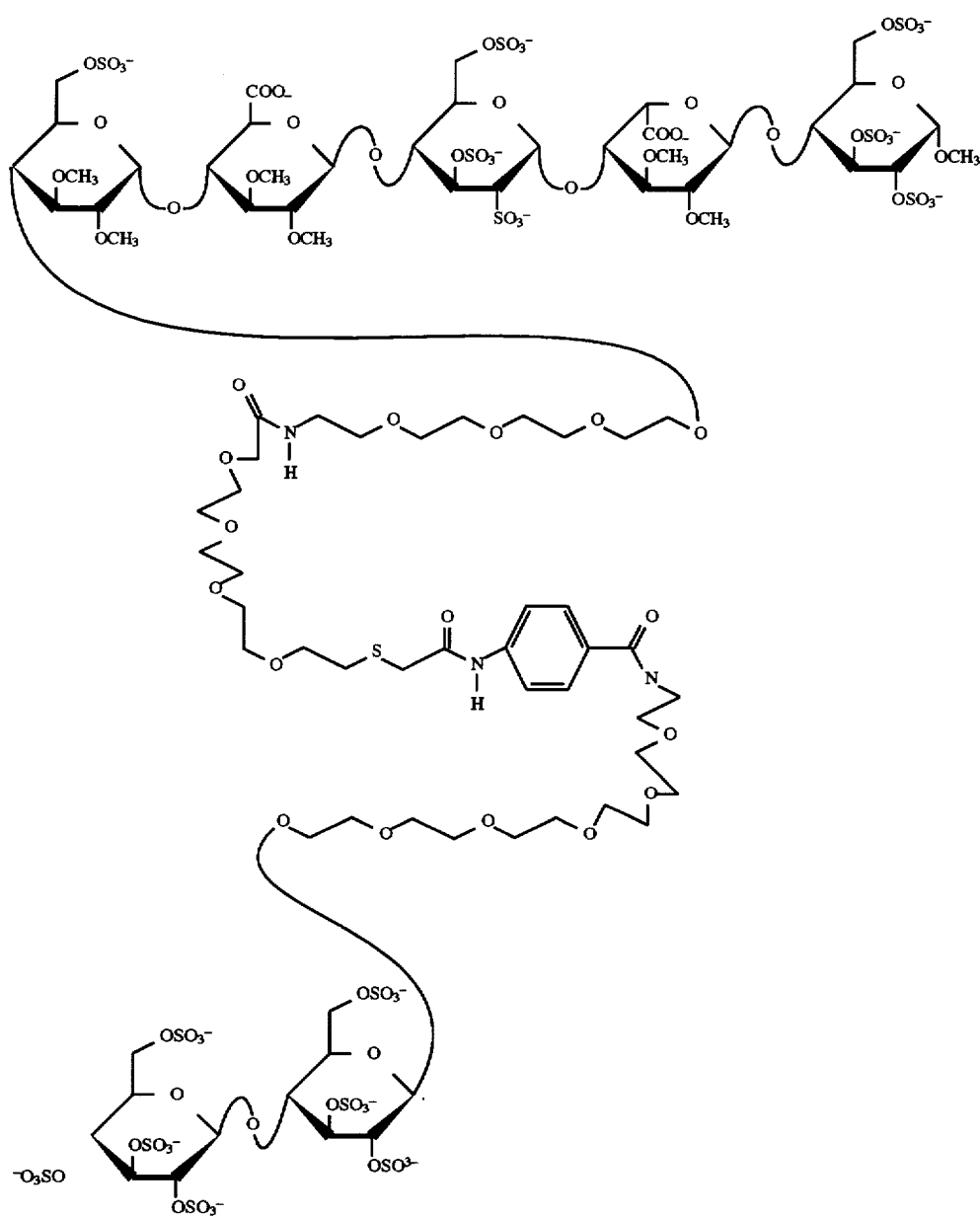

UNITED STATES PATENT AND TRADEMARK OFFICE
CERTIFICATE OF CORRECTION

PATENT NO.    : 5,705,489
DATED         : January 6, 1998
INVENTOR(S)   : Constant A. A. Van Boeckel et al.

It is certified that error appears in the above-identified patent and that said Letters Patent is hereby corrected as shown below:

Delete entire spec. Columns 1 - 72, & substitute the attached spec. columns 1 - 70, as per attached.

Signed and Sealed this

Nineteenth Day of November, 2002

*Attest:*

*Attesting Officer*

JAMES E. ROGAN
*Director of the United States Patent and Trademark Office*

BISCONJUGATES COMPRISING TWO SACCHARIDES AND A SPACER

This application is a continuation of U.S. Ser. No. 08/299,183, filed Aug. 31, 1994, now abandoned.

The invention relates to tuneable bisconjugates comprising two saccharides and a spacer, to a process for the preparation thereof, a pharmaceutical composition containing the same, and a use of said bisconjugates for the manufacture of a medicament.

Antithrombotic bisconjugates comprising two saccharides and a spacer are known from European patent application 312,086. The saccharide moieties of these compounds contain sulfated galactopyranosyl, mannopyranosyl, or glucopyranosyl units. These saccharides do not belong to the class of glycosaminoglycans or glycosamino-glycanoids such as disclosed in European patent application 529,715, which contain uronic acids. It is not disclosed whether these saccharides per se show anti-thrombotic activity. Moreover, only a spacer is disclosed which has a very specific structure, and which can have a chain length as small as 8 atoms, whereas it is found that the bisconjugates of the present invention are not active when they have a spacer chain length smaller than 20 atoms. In addition, in the bisconjugates disclosed in EP 312,086 the saccharides are connected to the spacer through both their reducing ends.

The present invention relates to a tuneable bisconjugate comprising two saccharides and a spacer, each saccharide being the same or different and comprising two to six monosaccharide units, at least one unit being uronic acid, characterized in that at least one of the saccharides per se has anti-thrombotic activity, and that the spacer connects at least one saccharide to the other through its non-reducing end, the chain length of the spacer being 20–120 atoms.

It is known that small carbohydrate molecules of the glycosaminoglycan type, are potent anti-Xa inhibitors. See for instance European patent 84999. Later filed patent applications showed that many variants of these basic molecules have similar activities. It is nowadays clear that these relatively small molecules (pentasaccharides are typical examples) interact with only one of the serine protease inhibitors, usually with anti-thrombin III (AT-III). The activated saccharide AT-III complex then inhibits selectively factor Xa. From investigations with natural occurring heparin and its fragments, it is known that longer glycosaminoglycans are required for the AT-III mediated inactivation of factor IIa (thrombin). Longer glycosaminoglycans having at least 16 saccharide units show anti-Xa as well as anti-IIa activity. Practically it is not interesting to synthesize glycosaminoglycans having 16 or more saccharide units, whereas fragmentation of heparin or other naturally occurring glycosaminoglycans leads to mixtures of compounds, mostly contaminated with other types of compounds, such as proteins, DNA, viruses and the like. From a medical point of view such mixtures are less attractive than pure and well-defined synthetic compounds, for instance because of the commonly occurring bleeding risks.

It has now been found that the properties of these larger glycosaminoglycans can be mimicked by two small saccharide molecules (comprising two to six mono-saccharide units), at least one saccharide being able to interact with protease inhibitors such as AT-III or HC-II, connected to each other by a spacer. To obtain the minimal required distance between the two saccharides, a spacer length of minimal 20 atoms is required. Spacers longer than 120 atoms are less suitable because of synthetic reasons. It has further been found that the chemical structure of the spacer is of minor or no importance. The anti-thrombotic activity and the αXa/αIIa activity ratio of the bisconjugates of this invention depend on the nature of the saccharides, the site of their connection to the spacer, and the length of the spacers. Saccharides connected to a spacer through both their reducing ends, for instance, are not active. At least one of the saccharides per se, preferably both saccharides per se, has (have) affinity for AT-III and/or HC-II, and/or has (have) anti-factor IIa and/or anti-factor Xa activity.

Suitable bisconjugates are bisconjugates wherein at least one of the saccharides has the formula:

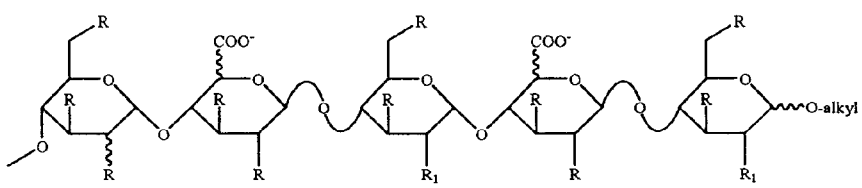

wherein each
R is independently selected from H, OH, $OSO_3^-$, and alkoxy; $R_1$ is independently selected from $OSO_3^-$ and $NHSO_3^-$; and the wrinkled lines denote either an upward or a downward bond, and the negative charges are compensated by hydrogen or an alkali metal cation.

The term alkyl, as used in this formula, is an alkyl group having 1–8, and preferably 1–4 carbon atoms. The most preferred alkyl group is the methyl group.

The term alkoxy means an alkoxy group having 1–8, and preferably 1–4 carbon atoms. Most preferred is the methoxy group. Sodium is the preferred alkali metal.

In the most preferred bisconjugates at least one of the saccharides has the formula:

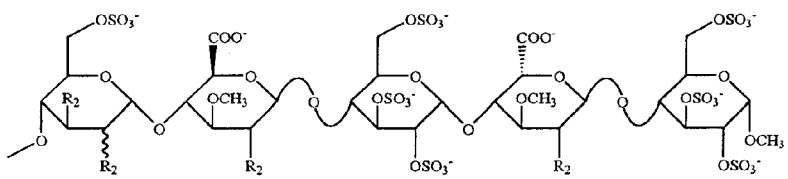

wherein $R_2$ is independently $OSO_3^-$ or $OCH_3$.

As previously emphasized, the chemical structure of the spacer is of secondary importance. For synthetic convenience, however, some spacers are more appropriate than others. Simple spacers that can easily be introduced are for example spacers having the formula:

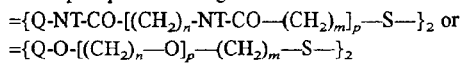

wherein
one of the two groups Q is attached to the non-reducing end of one of the saccharides and the other group Q is attached to the reducing or non-reducing end of the other saccharide, and each of the groups Q is a phenylene ($C_6H_4$) group or $—[(CH_2O)_q—(CH_2)_r—O]_s—[(CH_2)_t-NT-CO]_u—(CH_2)_v$, and T is independently hydrogen or alkyl as previously defined; q being 0 or 1; r and t being independently 2–4; and s being independently 1–12, preferably 1–6; u and v being independently 1–6; n is 1–8, m is 1–8, p is 1–12, and the total number of atoms is 20–120.

Another suitable spacer has the formula:

wherein
one of the two free valencies of the spacer is attached to the non-reducing end of one of the saccharides and the other free valency of the spacer is attached to the reducing or non-reducing end of the other saccharide, and T is independently H or alkyl as previously defined; m is independently 1–8; r is independently 2–4; s is independently 1–12, preferably 1–6; w is 0–10, preferably 0–7; x is 0 or 1; y is 0 or 1; z is 0 or 1, and the total number of atoms is 20–120.

These embodiments are preferred because of their easy accessibility, however, the spacers are by no means limited to the above-mentioned.

The bisconjugates of the invention are called symmetric when both saccharides are the same. The bisconjugates are called asymmetric when both saccharides are different from each other. Preferably asymmetric bisconjugates comprise one saccharide not having uronic acid units, thus being different from glycosaminoglycans and glycosaminoglycanoids, for example a saccharide consisting of glucose-units, e.g. cellobiose, maltotriose or maltopentaose or derivatives thereof.

The bisconjugates of the invention can be prepared by methods known for the preparation of analogous compounds. Usually the carbohydrate moieties are prepared by using methods known in the literature (for example using the methods of EP 84999, EP 301618, EP 454220, EP 529715 and EP application 9304769). By application of temporary protective groups the desired hydroxy group can be freed for coupling to the spacer. More preferred, however, is the attachment of a suitable linker group to the desired hydroxy group, for instance a nitrophenyl group, which during the

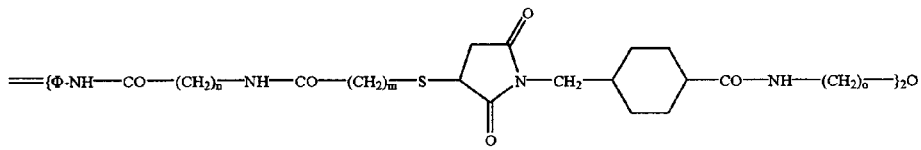

wherein
one of the two groups Φ is attached to the non-reducing end of one of the saccharides and the other group Φ is attached to the reducing or non-reducing end of the other saccharide and Φ denotes a phenylene ($C_6H_4$) group; n, m, and o are independently 1–8, and the total number of atoms is 20–120.

Other equally suitable spacers have the formula:

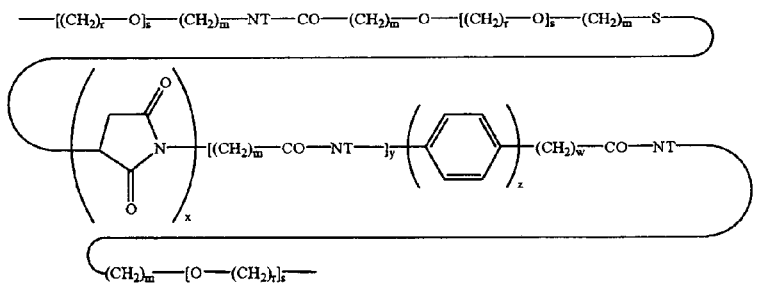

usual reduction step (the cleavage of the benzyl protective groups) converts into the corresponding aniline group, the amino group of which can be used to couple with the remainder of the spacer (having for instance a halogen or an active ester of a carboxylic group at its end), or can optionally be temporarily protected and coupled to the remainder of the spacer in a later stage. The aniline group thereby becomes part of the spacer. Another method, especially useful when the carbohydrate moieties are the same, is the coupling of the carbohydrate moiety to a moiety which corresponds to a half of the spacer and whose end not to be bonded to the saccharide is protected with a protective group, which moiety is prone to dimerization without said protective group. After deprotection the molecule dimerizes under the suitable reaction conditions to the bisconjugate of the invention. A variant of the above-mentioned method is the coupling of a part of the spacer to the carbohydrate moiety, after which the spacer part is further built-up by chemical condensation. This method is particularly useful for the preparation of bisconjugates with various spacer lengths, starting from the same carbohydrate moieties. Yet another method is coupling of the spacer, or a half of the spacer, to a part of the carbohydrate moiety, which is coupled by standard carbohydrate coupling techniques with the remaining carbohydrate part to the required bisconjugate or half of the bisconjugate, after which, when necessary, deprotection and dimerization of the spacer can be performed as previously described. The bisconjugates of the invention can be used for the treatment or prevention of thrombotic disorders or smooth muscle cell proliferation. The bisconjugates of the invention may be administered enternally or parenterally, and for humans preferably in a daily dosage of 0,001–10 mg per kg body weight. Mixed with pharmaceutically suitable auxiliaries, e.g. as described in the standard reference, Gennaro et al, Remington's Pharmaceutical Sciences, (18th ed., Mack Publishing Company, 1990, see especially Part 8; Pharmaceutical Preparations and Their Manufacture) the bisconjugates, when orally, buccally or sublingually active, may be compressed into solid dosage units, such as pills and tablets, or they may be processed into capsules or suppositories. When parenterally active, the bisconjugates can also be applied as an injection or infusion preparation by means of pharmaceutically suitable liquids in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The tuneability of the compounds of the invention is demonstrated in Tables I, II and III. It appears that the saccharides, the length of the spacer, and combinations thereof can tune the αXa/αIIa activity ratio.

The spacer length is the number of atoms of the spacer, counted along the shortest chain between the two saccharides, not counting the oxygen atoms of the saccharides which are connected to the spacer.

TABLE I

Bisconjugates having different saccharide moieties and the same spacer length.

| bisconj. | spacerl. (atoms) | αXa act.[a] | αIIa act.[b] | αXa/αIIa |
|---|---|---|---|---|
| VII | 54 | 767 | 14 | 54.8 |
| V | 54 | 638 | 36 | 17.7 |
| VI | 54 | 278 | 156 | 1.78 |
| VIII | 54 | 49 | 91 | 0.54 |
| X | 52 | 181 | 71 | 2.56 |
| XI | 52 | 163 | 161 | 1.01 |
| IX | 52 | 79 | 108 | 0.73 |
| IV | 52 | 17 | 31 | 0.54 | bisconj. = bisconjugate
spacerl. = spacer length
[a]anti-Xa activity (units/mg) was determined according to the method of A. N. Teien and M. Lee, Thrombosis Research, 10, 399–410 (1977).
[b]anti-IIa activity (units/mg) was determined according to the method of M. L. Larson et al., Thrombosis Research, 13, 285–288 (1978).

Conclusion: In Table I it is shown that the αXa/αIIa activity ratio of the bisconjugates can be tuned by variation of the saccharides.

TABLE II

Bisconjugates with the same saccharide moieties and different spacer lengths.

| bisconj. | spacerl. (atoms) | αXa act. | αIIa act. | αXa/IIa |
|---|---|---|---|---|
| I | 32 | 704 | 15 | 46.9 |
| III | 46 | 419 | 21 | 20.0 |
| II | 57* | 628 | 120 | 5.23 |

*spacer length determined via the methylene group of the cyclopentyl groups (shortest chain).

Conclusion: Table II illustrates that the αXa/αIIa activity ratio of the bisconjugates can be tuned by variation of the spacer length.

TABLE III

Bisconjugates having miscellaneous saccharides and/or spacer lengths.

| bisconj. | spacerl. (atoms) | αXa act. | αIIa act. | αXa/αIIa |
|---|---|---|---|---|
| XIV | 53 | 493 | 64 | 7.7 |
| XIII | 56* | 281 | 327 | 0.86 |
| XII | 56* | 41 | 279 | 0.15 |

*spacer length determined via the methylene group of the cyclopentyl groups (shortest chain).

Conclusion: Table III shows tuning of the αXa/αIIa activity ratio of the bisconjugates by changing saccharides and spacer lengths.

The invention is further illustrated by the following examples.

EXAMPLE 1

Monosaccharide 5

Compound 1 (3.5 g) (see Carb. Res. 1989, 186(2), 189–205) was dissolved in dimethylformamide (30 ml) and sodium hydride (560 mg) was added under nitrogen atmo sphere. The mixture was cooled to 0° C. and 1-fluoro-4-nitrobenzene (1.63 ml) was added during 2 min. After 30 min of stirring the mixture was concentrated, diluted with dichloromethane and water and extracted. After conventional work-up the residue was purified by column chromatogrpahy to give 4 g of compound 2. Compound 2 was converted into compound 3 by acetolysis, followed by saponification which gave compound 4, which after reaction with trichloroacetonitrile afforded compound 5. For the synthesis of compounds 3, 4, and 5 procedures were used as described for the preparation of compounds 9 (vide infra), 41, and 42 (see example 4), respectively.

of chromium(VI)oxide was destroyed with methanol and after neutralisation of the mixture with sodium hydrogencarbonate, water was added. After extraction with dichloromethane the organic layer was dried and concentrated. The residual oil was dissolved in dry dimethylformamide (174 ml). Potassium hydrogen-carbonate (7 g) and iodomethane (7 ml) were added and the mixture was stirred for 3 hours at room temperature. After concentration the residue was purified by silica gel chromatography to give 9.1 g of compound 8.

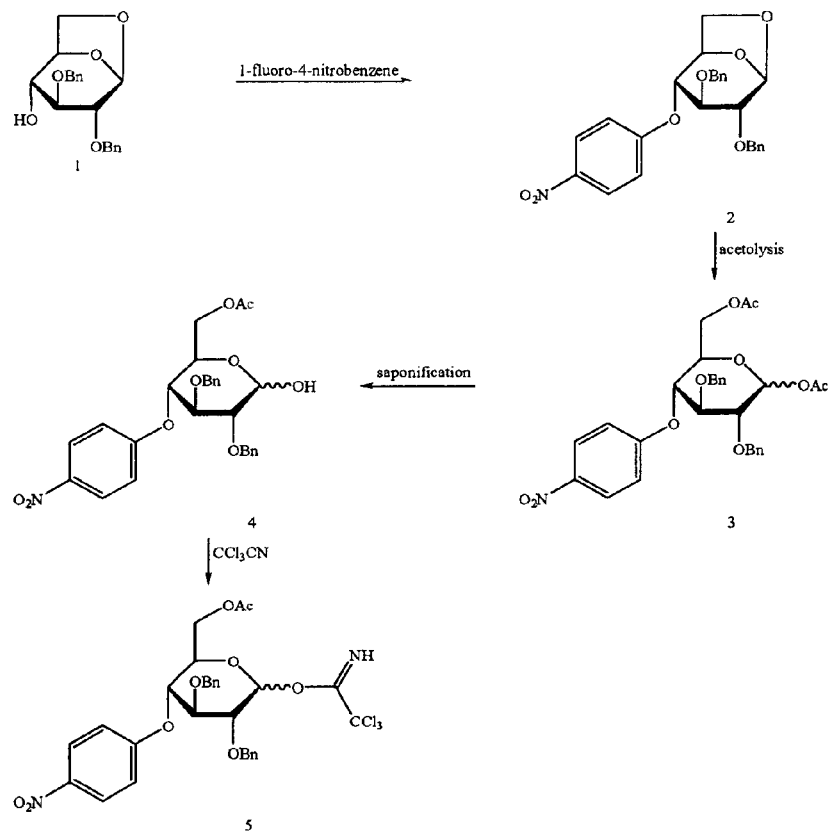

Tetrasaccharide 14

Compound 7 was prepared from compound 6 (see Bioorganic and Medicinal Letters 1992, 2(9), 905) according to the procedure as described for compound 39 (see example 4).

Compound 7 (14.6 g) was dissolved in acetone (260 ml) and cooled to 0° C. At this temperature a solution of chromium(VI)oxide (10.8 g) in a mixture of water (53 ml) and concentrated sulfuric acid (10.5 ml) was added dropwise. The mixture was stirred for 16 hours at 2° C. Excess Compound 8 (2.8 g) was dissolved in a mixture of acetic anhydride (50 ml), acetic acid (0.3 ml) and trifluoroacetic acid (3.0 ml). After 3 hours of stirring the mixture was concentrated and coevaporated with toluene to give 3.1 g of compound 9.

Compound 10 was prepared by saponification of compound 9 which subsequently was converted to imidate 11. Procedures as described for the preparation of compounds 41 and 42 were utilized (see example 4).

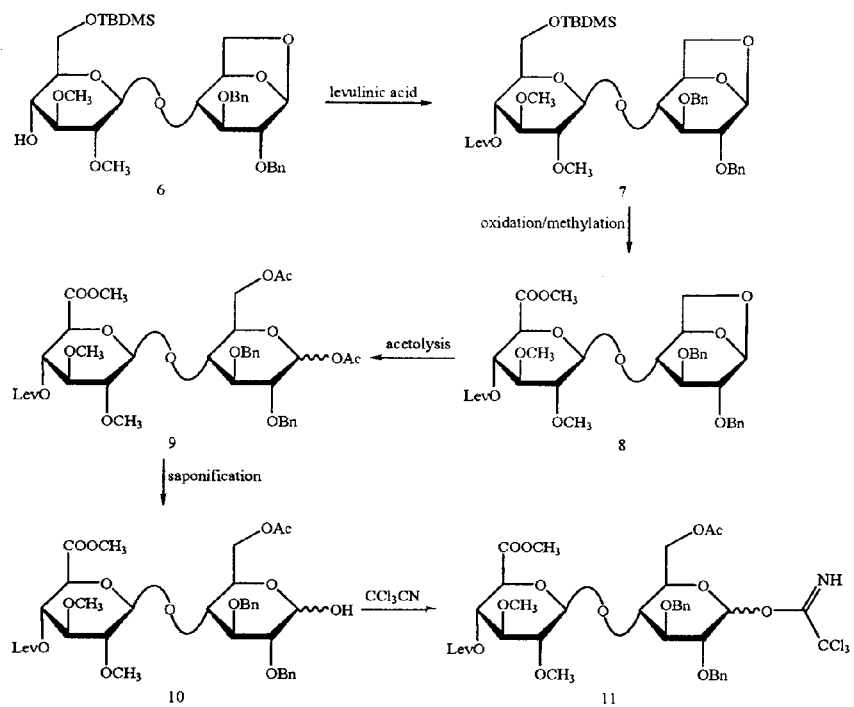

Compound 11 was coupled with compound 12 (see Jaurand G., et al., Bioorganic and Medicinal Chem. Lett., 2 )9), 897–900 (1992), compound 12) to form compound 13 from which the Lev-group was removed as a result of which the tetrasaccharide 14 was obtained. Procedures as described for the preparation of compounds 43 and 44 were followed (see example 4).

Mol sieves 4 Å (70 mg) were added to a solution of 79 mg of tetrasaccharide 14 and 70 mg of monosaccharide 5 in 2.5 ml of dichloromethane. The mixture was cooled to 31 20° C. and 6.8 μmol of trimethylsilyl trifluoromethanesulfonate were added. The mixture was stirred for 30 min and sodium hydrogencarbonate was added. The mixture was filtered, the solvent evaporated, and the residue purified by silica chromatography to give 88 mg of pentasaccharide 15 which were dissolved in 7.3 ml of tetrahydrofuran and cooled to −5° C. At this temperature 2.6 ml of 30% aq. hydrogen peroxide were added and after 10 min 1.2 ml of 1.25M lithium hydroxide solution were added. The mixture was stirred overnight at 0° C., 4.8 ml of methanol and 1.3 ml of 4M sodium hydroxide solution were added, and after stirring for 1 h the temperature was raised to 20° C. and the mixture was stirred for another 20 h. The reaction mixture was acidified to pH 3 with 6N hydrochloric acid at 0° C., and the saponified product was extracted with ethyl acetate. The excess of hydrogen peroxide was decomposed by extraction with a 5% sodium sulfite solution, and the organic mixture was dried over magnesium sulfate and evaporated to give 89 mg of crude pentasaccharide 16.

Pentasaccharide 16 was dissolved in 10.2 ml of dimethylformamide and 55 mg of 10% Pd on charcoal were added. After hydrogenolysis overnight 64 mg of crude pentasaccharide 17 were obtained.

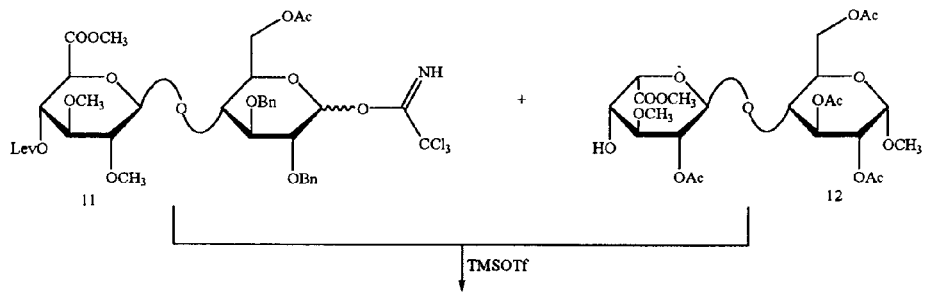

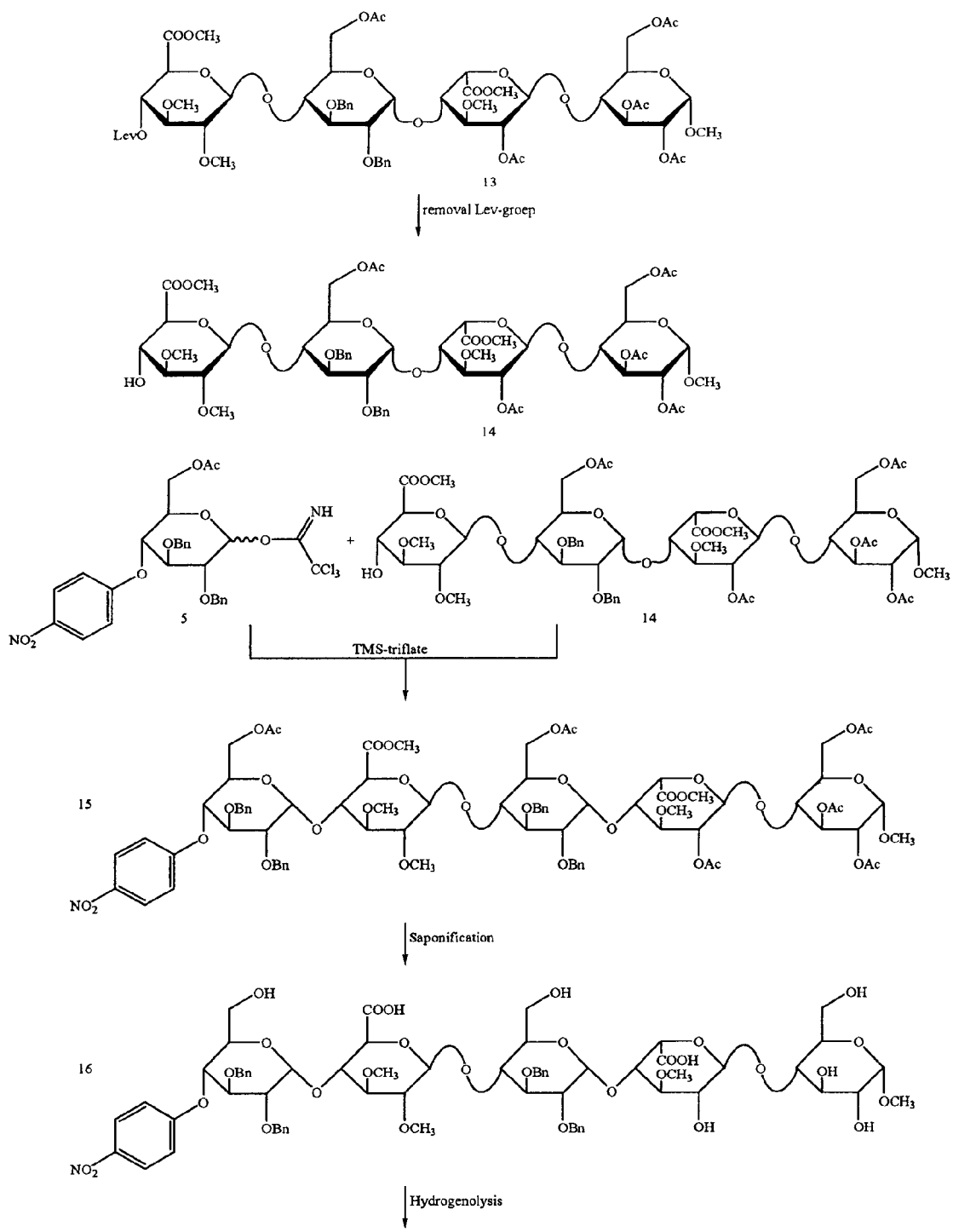

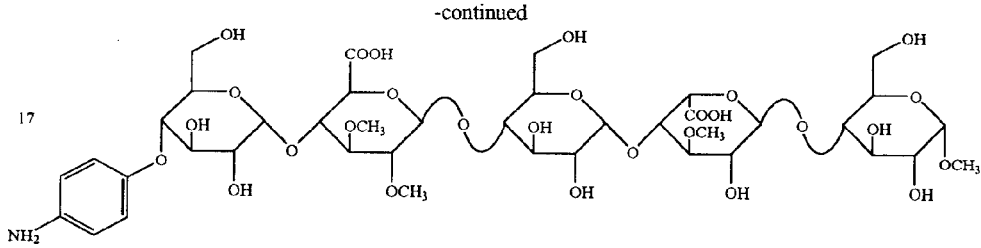

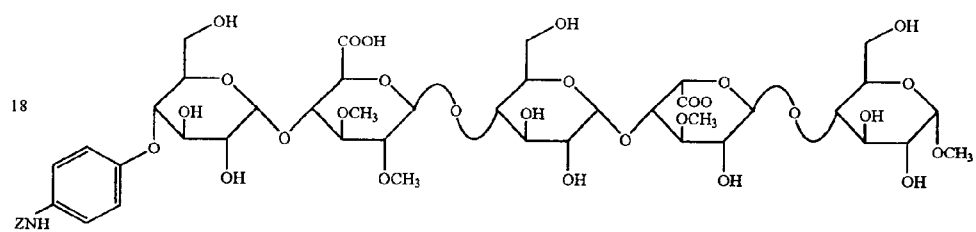

Pentasaccharide 17 (49 mg) was dissolved in 2 ml of a mixture of ethanol-water (1:1), and to this mixture were added 16 mg of sodium hydrogencarbonate and 10.4 µl of benzyloxycarbonylchloride (Z-Cl). After stirring for 4 h at room temperature the solvent was evaporated and methanol was added to the residue. The salts were filtered off and the filtrate was evaporated to give 67 mg of crude pentasaccharide 18, which were dissolved in 2.5 ml of dry dimethylformamide. Under nitrogen 442 mg of triethylamine sulfurtrioxide were added and the mixture was stirred overnight at 50° C., after which an aqueous solution of sodium hydrogencarbonate was added under ice cooling. The mixture was stirred for 1 h at room temperature, concentrated to a small volume and desalted on a Sephadex G-25 column. The isolated product was eluted with water on a Dowex 50WX8 Na⁺ column to give 104 mg of pentasaccharide 19. 100 mg of pentasaccharide 19 were dissolved in 8 ml of water, 10% Pd on charcoal was added, and the mixture was hydrogenolysed overnight to give 83 mg of pentasaccharide 20. $[\alpha]_D^{20}=+58.1°$ (c=1; water). 9.6 mg of pentasaccharide 20 and 4.8 mg of sulfo-LC-SPDP were dissolved in a mixture of 0.1 ml of ethanol and 0.35 ml of an aqueous 0.05M disodium hydrogenphosphate solution having a pH 7.8. The mixture was stirred for 3 h and desalted on a Sephadex G-25 column to give 9.0 mg of monoconjugate 21. Monoconjugate 21 (8.9 mg) was dissolved in 1.5 ml of an aqueous 0.05M sodium dihydrogenphosphate solution having a pH 8.0. 157 µl of a 0.05M solution of tributylphosphine in isopropanol were added at room temperature, the mixture was stirred for 1 h and air was passed through the reaction mixture. After desalting of the mixture on a Sephadex G-25 column, the crude bisconjugate was purified by HPLC using a mono Q anion exchange column to give 4.0 mg of bisconjugate I. $[\alpha]_D^{20}=+45.7°$ (c=0.35; water).

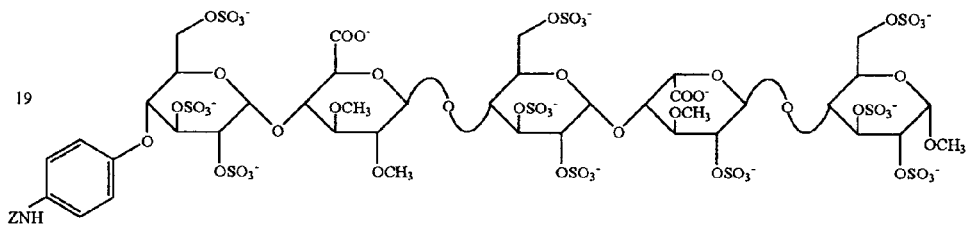

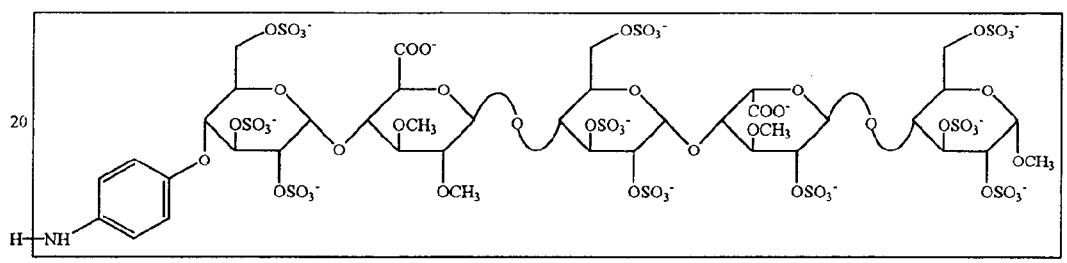

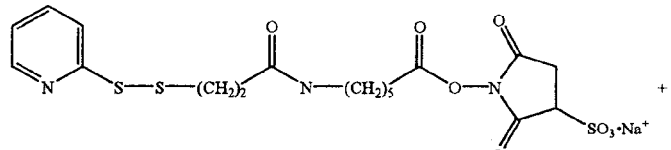

Sulfo-LC-SPDP

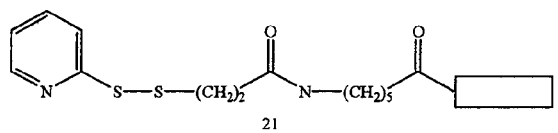

21

1) tributylfosfine
2) air $O_2$

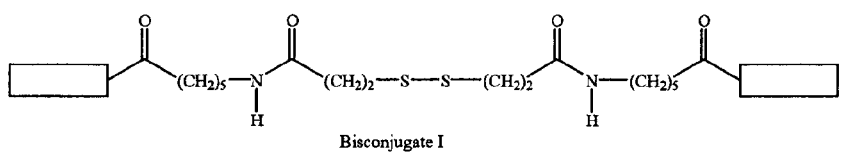

Bisconjugate I

EXAMPLE 2

Monoconjugate 21 (14.7 mg) was dissolved in a mixture of 1 ml of methanol and 2 ml of an aqueous solution of 0.1M sodium dihydrogenphosphate pH 8. 247 μl of a 0.05M solution of tributylphosphine in isopropanol were added under nitrogen at room temperature. The mixture was stirred for 1 h and a solution of 1.68 mg of 23 in 0.5 ml of dimethylformamide were added and the mixture was stirred for another 3 h. After desalting of the mixture on a Sephadex G-25 column, the crude product was further purified by elution with a 0.05M aqueous sodium chloride solution containing 10% acetonitrile on a Sephadex G-50 column. The pooled fractions were desalted on Sephadex G-25 to give 5.5 mg of bisconjugate II. $[\alpha]_D^{20}=+7.0°$ (c=0.34; water).

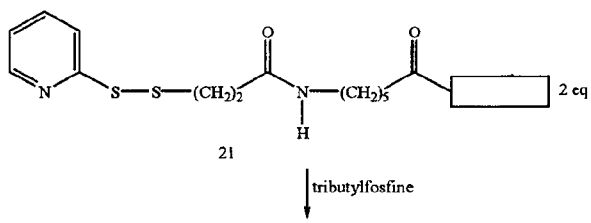

21 tributylfosfine

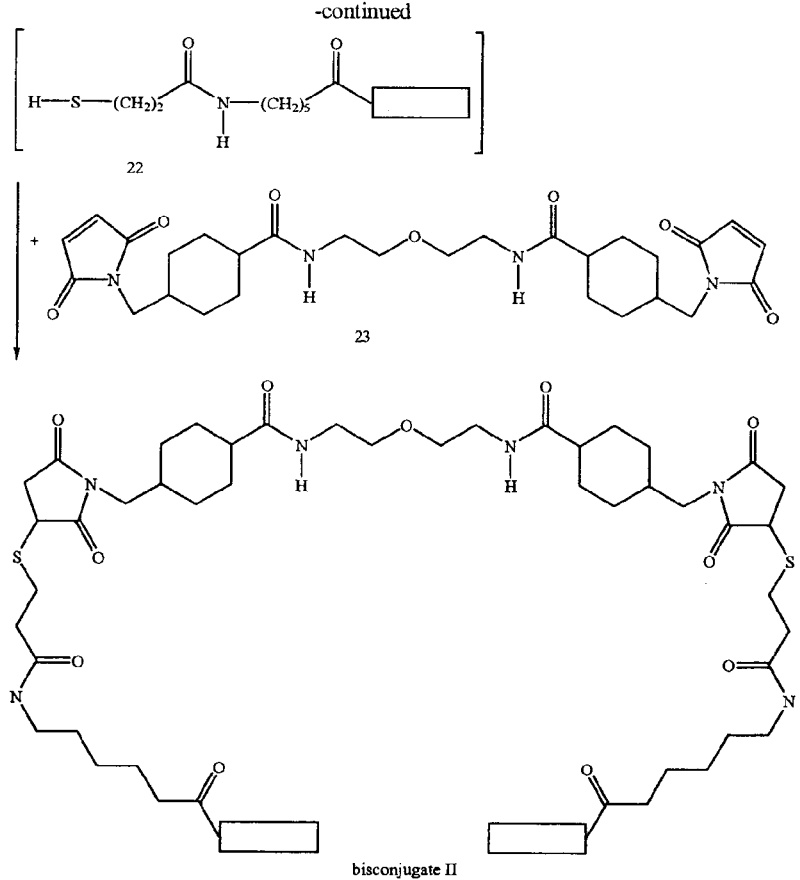

bisconjugate II

EXAMPLE 3

Methyl 2,3,6-tri-0-benzyl-α-D-glucopyranoside (2.1 g) 24 was dissolved in 75 ml of dimethylformamide and 5.5 ml of tetraethylene glycol di-p-tosylate were added at room temperature. Sodium hydride (162 mg) was added and the mixture was heated for 2 h at 50° C. Lithium azide (4.5 g) was added and the reaction mixture was stirred at 70° C. for another 5 h. The mixture was then concentrated and purified by column chromatography to give 1.52 g of compound 25. To a solution of compound 25 (768 mg) in 40 ml of acetic anhydride at −20° C., 10 ml of a 5% (v/v) solution of sulfuric acid in acetic anhydride (cooled to 31 20° C.) were added. The mixture was stirred for 10 min at this temperature and sodium acetate (3.5 g) was then added to stop the reaction. After 10 min the mixture was extracted with ethyl acetate, the combined extracts were washed with a 10% aqueous sodium hydrogencarbonate solution, dried, and concentrated. Column chromatography of the crude product gave 573 mg of compound 26. Compound 26 (269 mg) was dissolved in a mixture of 5.5 ml of dimethylformamide, 31 µl of acetic acid, and 28 µl of hydrazine monohydrate. The mixture was stirred for 3 h at room temperature, diluted with dichloromethane and water and extracted. Conventional work-up and column chromatography of the product yielded 158 mg of compound 27. Compound 27 (158 mg) was dissolved in 2 ml of dichloromethane. Trichloroacetonitrile (0.13 ml) and cesium carbonate (17.8 mg) were added under nitrogen atmosphere. The mixture was stirred for 1 h at room temperature, filtered and evaporated. Column chromatography of the product yielded 182 mg of compound 28.

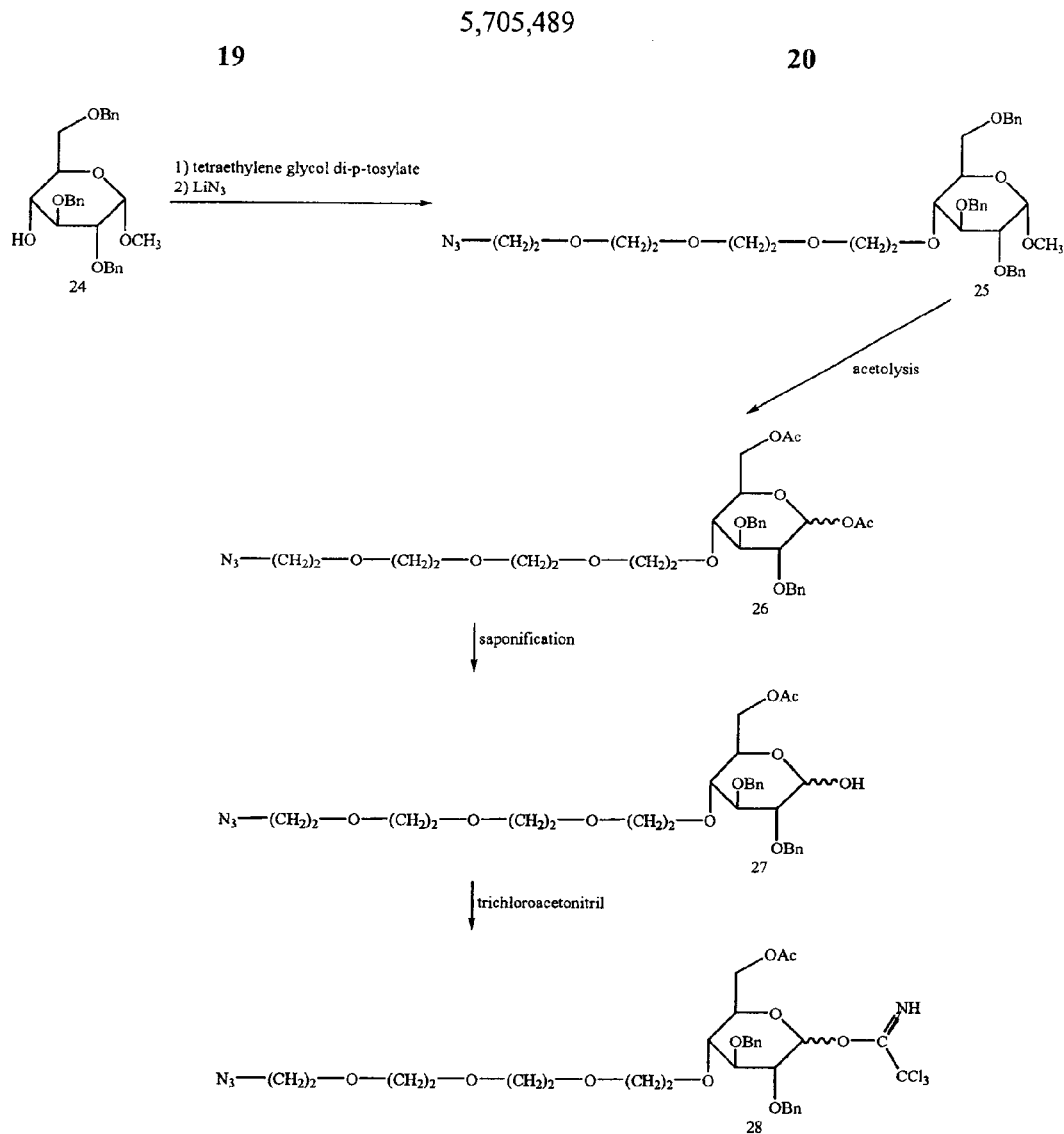
Compound 31 was prepared by coupling compound 11 with compound 29 (see H. Lucas et al., Angew. Chem. 1993, 105, 462–464) to form compound 30 from which the Lev- group was removed. Procedures as described for the preparation of compounds 43 and 44 were followed (see example 4).
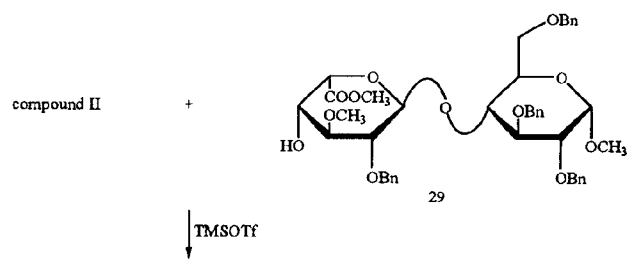

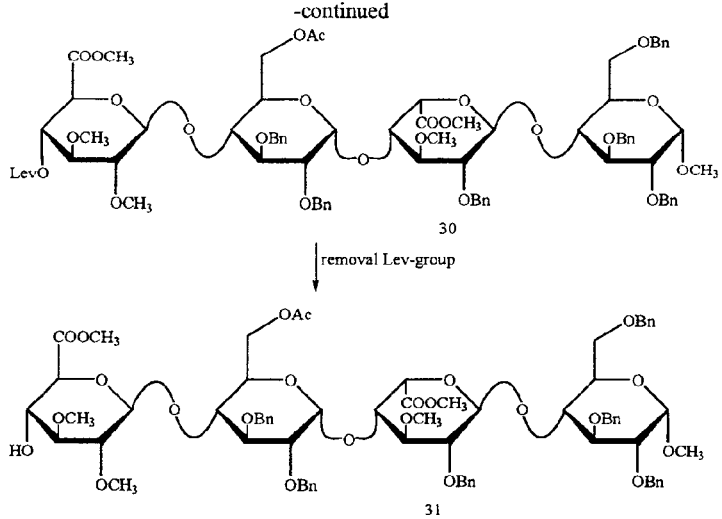

Compounds 32, 33, and 34 were prepared in a manner similar to that as described for compounds 15, 16, and 17 respectively (see example 1). Compound 34 (35 mg) was dissolved in 0.35 ml of a stock-solution of 280 μl of triethylamine in 20 ml of dimethylformamide. N-(benzyloxycarbonyloxy)-succinimide (10.6 mg) was added at pH 7.5 and after 30 min of stirring the solvent was partly removed by evaporation. The residue was first purified on a Sephadex LH-20 column, followed by further purification a Rp-18 column (acetonitrile:water:ammonia= 95:5:2 v/v) to give 29.4 mg of compound 35. Compound 36 was prepared in a similar manner as described for compound 19 (see example 1). $[\alpha]_D^{20}=22.8°$ (c=0.3; water). Compound 36 (51.4 mg) was dissolved in 4 ml of water and the catalyst (10% Pd/C) was added. The mixture was stirred under an atmosphere of hydrogen gas for 5 h at room temperature. After filtration the solvent was evaporated to give 47 mg of compound 37. Compound 37 (15.1 mg) was dissolved in 450 μl of a solution of N,N-diisopropylethylamine in dimethylformamide:water=7:3 (pH 9.0) and excess of sulfosuccinimidyl 6-[3'(2-pyridyldithio)propioamide] hexanoate was added at a constant pH value of 9.0. After 20 min stirring the mixture was desalted on a Sephadex G-25 column with water:acetonitril 8:2 (v/v) to give 16 mg of crude compound 38. Bisconjugate III was prepared from compound 38 in a similar manner as described in example 1 for the conversion of compound 21 into bisconjugate I. $[\alpha]_D^{20}=+29.6°$ (c=0.125; water).

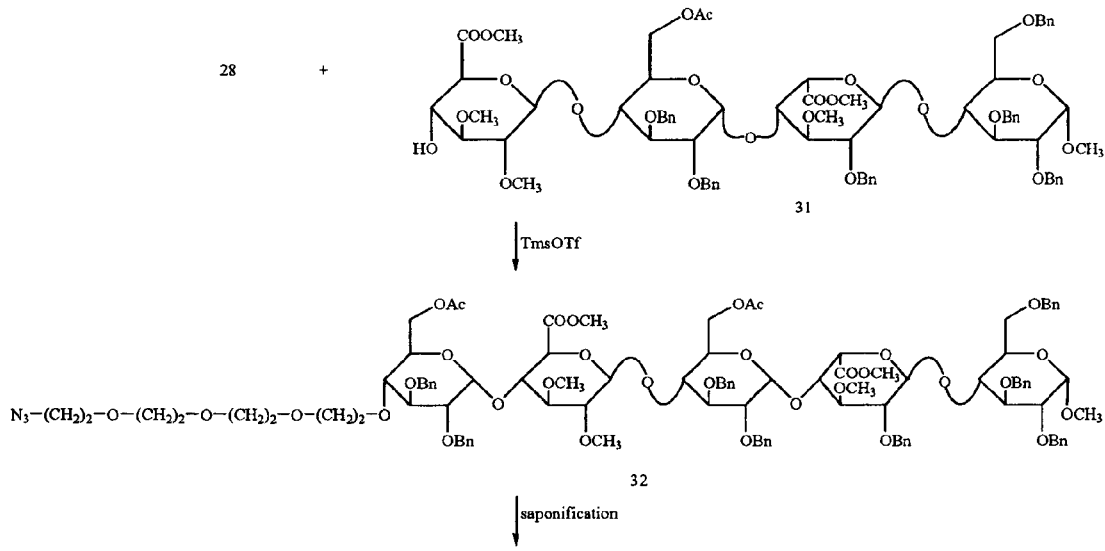

-continued
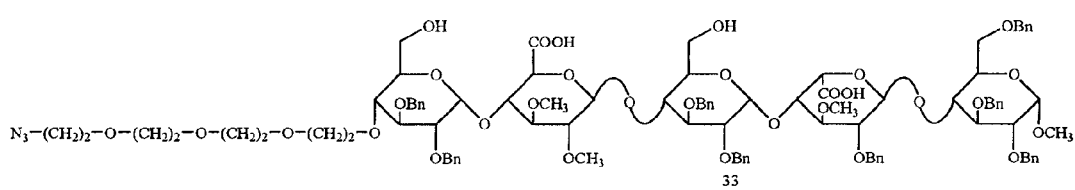
33
↓ hydrogenolysis
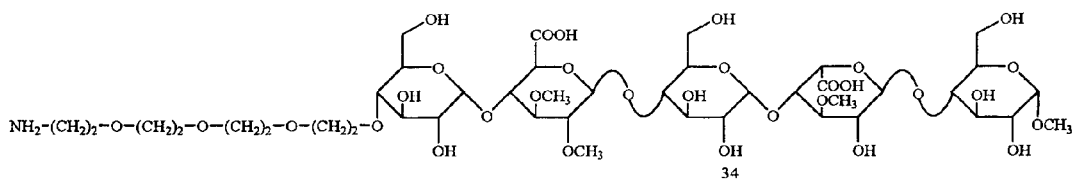
34
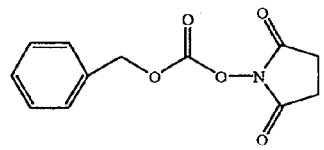 + 34
↓
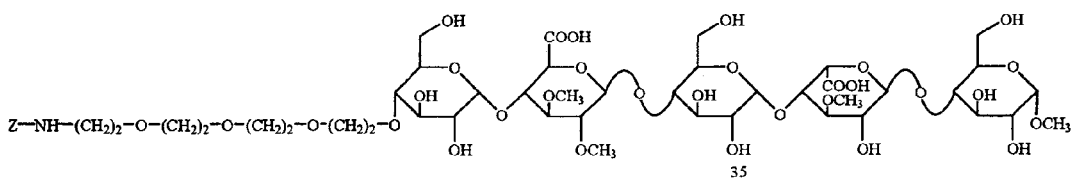
35
↓ sulfation
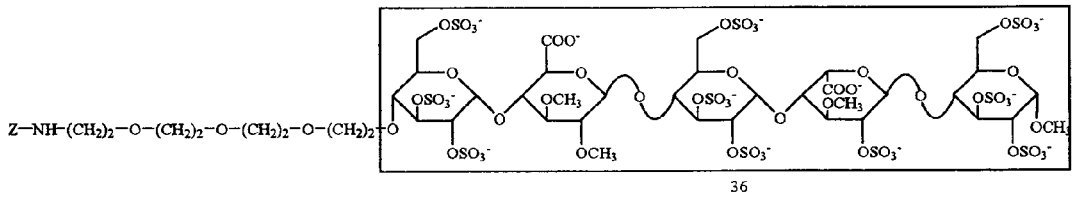
36
↓ H₂ Pd/C
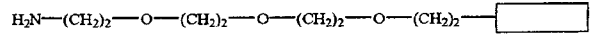
37
↓ Sulfo-LC-SPDP
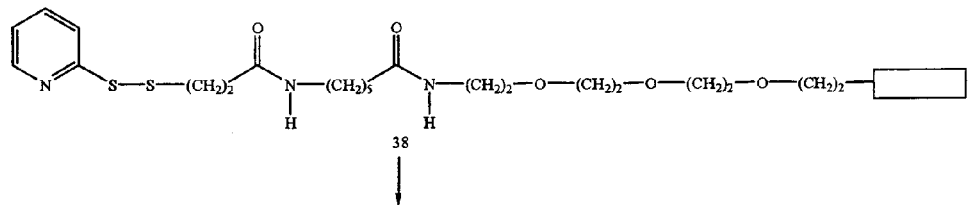
38
↓

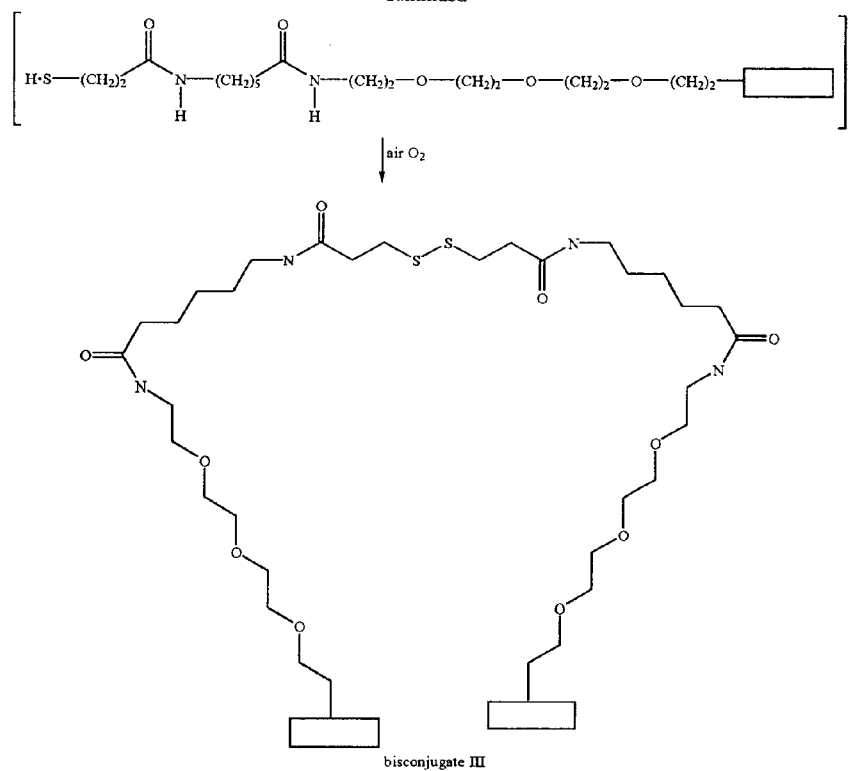

bisconjugate III

EXAMPLE 4

Bisconjugate IV ($[\alpha]_D^{20}=+50.8°$ (c=0.32; water) was prepared according to the procedure of example 3, the differences being the use of tetrasaccharide 44 instead of 31, and the application of succinimido N-(benzyl-oxycarbonyloxy) glycine instead of N-(benzyl-oxycarbonyloxy) succinimide.

4-dimethylaminopyridine (25 mg) were added. After 2 hours of stirring diethyl ether was added and the mixture was cooled to 0° C. Crystals were filtered off and the filtrate was concentrated. The residual oil was purified by column chromatography to give 900 mg of compound 39. A solution of compound 39 (1 g) in acetic anhydride (50 ml) was cooled to −20° C. At this temperature 10 ml of solution A, which

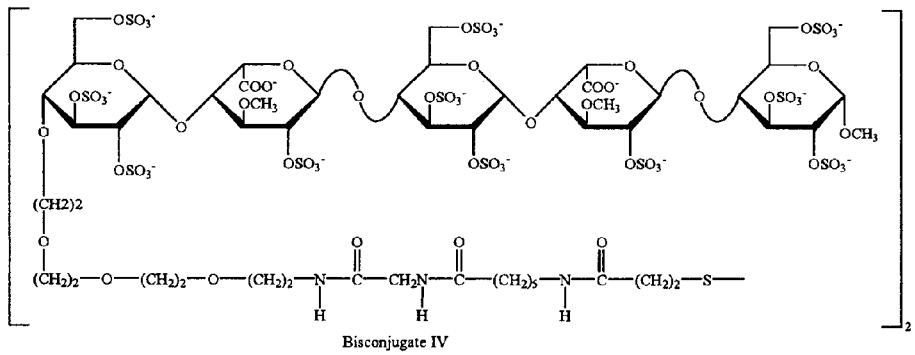

Bisconjugate IV

Preparation of tetrasaccharide 44

Disaccharide 29 (0.8 g) was dissolved in dioxane (5.3 ml), after which levulinic acid (278 mg), 1,3-dicyclohexylcarbodiimide (494 mg) and had been prepared by adding 1 ml of sulfuric acid 98% to 20 ml of acetic anhydride at −20° C., was added under nitrogen atmosphere. After 2.5 hours of stirring the reaction was stopped by addition of sodium acetate. Ethyl acetate and a saturated sodium hydrogencarbonate solution were added to the cold reaction mixture and after extraction the organic layer was washed with water, dried and concentrated. The crude product was purified by column chromatography to give 800 mg of compound 40. Compound 40 (800 mg) was dissolved in dry tetrahydrofuran (10 ml) and piperidine (1.3 ml) was added under a nitrogen atmosphere. The mixture was stirred for 20 hours at 20° C. and subsequently diluted with ethyl acetate. The organic layer was washed with 0.3N hydrochloric acid and water and dried. After concentration of the organic layer the residue was purified by column chromatography to give 430 mg of compound 41. To a solution of compound 41 (490 mg) in dichloromethane (5.4 ml) cesium carbonate (43 mg) and trichloroacetonitrile (0.52 ml) were added. The mixture was left for 1 hour at 20° C. After filtration the filtrate was concentrated and the residue was purified by column chromatography giving 417 mg of compound 42. Compound 42 (317 mg) and compound 29 (243 mg) were co-evaporated twice with toluene. Dichloromethane (7.1 ml) and powdered mol sieves 4 Å (235 mg) were added and the mixture was cooled to −20° C. At this temperature a solution of trimethylsilyl trifluoromethanesulfonate (8.75 µl) in dichloromethane (2.8 ml) was added dropwise. After stirring for 1 hour the reaction was stopped by addition of solid sodium hydrogencarbonate. The mixture was stirred for antoher 15 min, filtered and concentrated. After purification by column chromatography 372 mg of compound 43 was obtained. Compound 43 (370 mg) was dissolved in pyridine (1.2 ml). A mixture of pyridine (1.2 ml), acetic acid (1.56 ml) and hydrazine hydrate (0.18 ml) was added at 20° C. and the mixture was stirred for 7 min. After dilution with water and extraction with ethyl acetate the organic layer was washed with a sodium hydrogencarbonate solution and water, dried and purified by column chromatography to give 324 mg of compound 44.

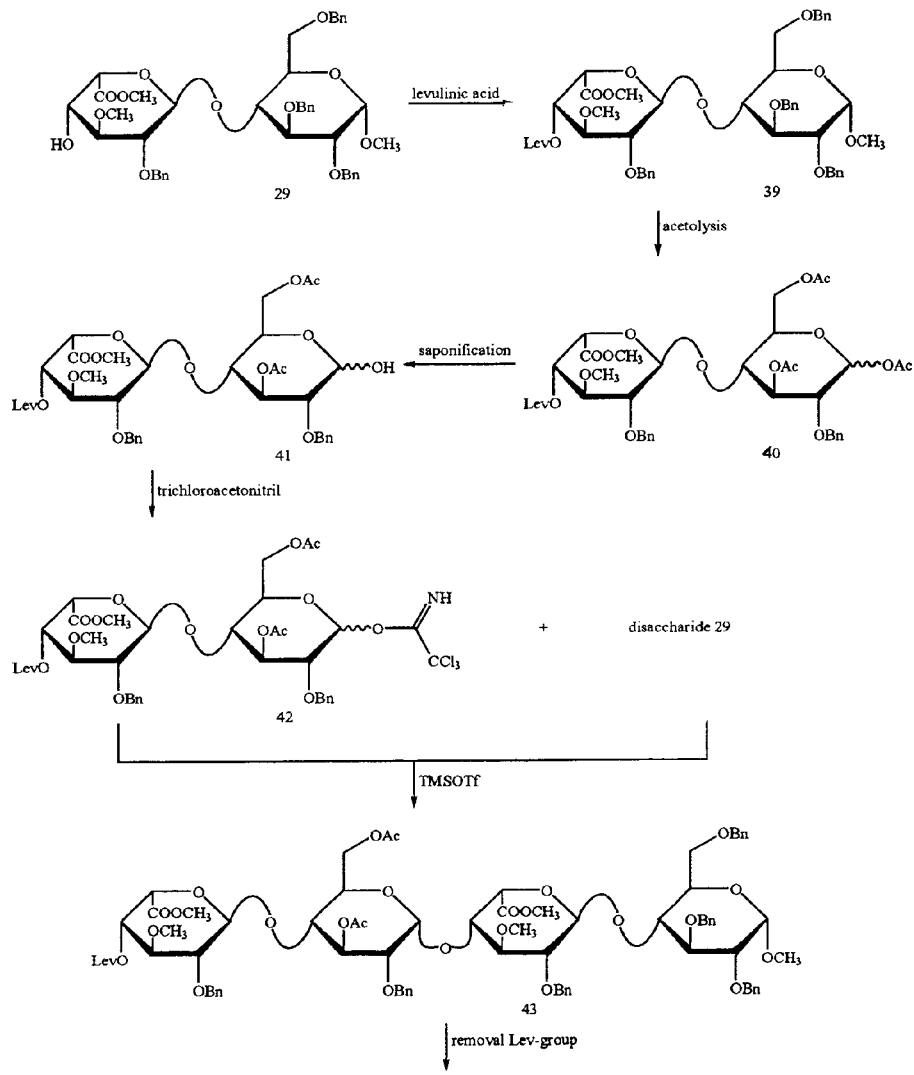

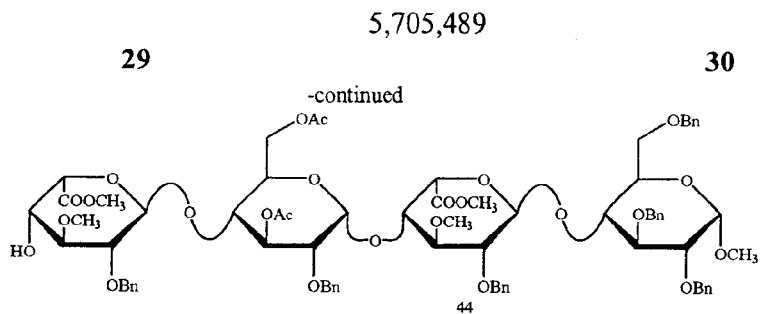

EXAMPLE 5

Preparation of active ester 52

Tetraethylene glycol 45 (10 g) was dissolved in dry tetrahydrofuran (150 ml) and sodium hydride (60% dispersion in mineral oil, 1.64 g), was added in small portions at 0° C. After 1 hour of stirring a solution of tert.-butyldimethylsilyl chloride (6.18 g) in tetrahydrofuran (20 ml) was added and the mixture was stirred for 15 min. After 10 min of stirring the mixture was diluted with water and extracted with ethyl acetate. The organic extract was dried and concentrated. Column chromatography of the crude product gave 6 g of compound 46. Compound 46 (5.0 g) was dissolved in tetrahydrofuran (80 ml) and tert. butyl bromacetate (26.2 ml) was added. The mixture was stirred at 50° C. and sodium hydride (1.16 g) was added in small portions under a nitrogen atmosphere. After one hour of stirring the mixture was worked up in the same manner as described for compound 46. Column chromatography of the residue yielded compound 47 (5 g). A solution of compound 47 (3.1 g) in a mixture of acetic acid (25 ml), water (8.3 ml) and tetrahydrofuran (8.3 ml) was stirred for 24 hours at 20° C. The mixture was neutralised with sodium hydroxide solution, diluted with water and extracted with ethyl acetate. The combined extracts were dried and concentrated. The crude product was filtered on a column of silica gel to give 1.52 g of compound 48. Compound 48 (1.4 g) was dissolved in dichloromethane (12.7 ml). Pyridine (7.7 ml) and p-toluenesulfonyl chloride (1.3 g) were added and the mixture was stirred for 20 hours at 20° C. After dilution with water the mixture was extracted with dichloromethane.

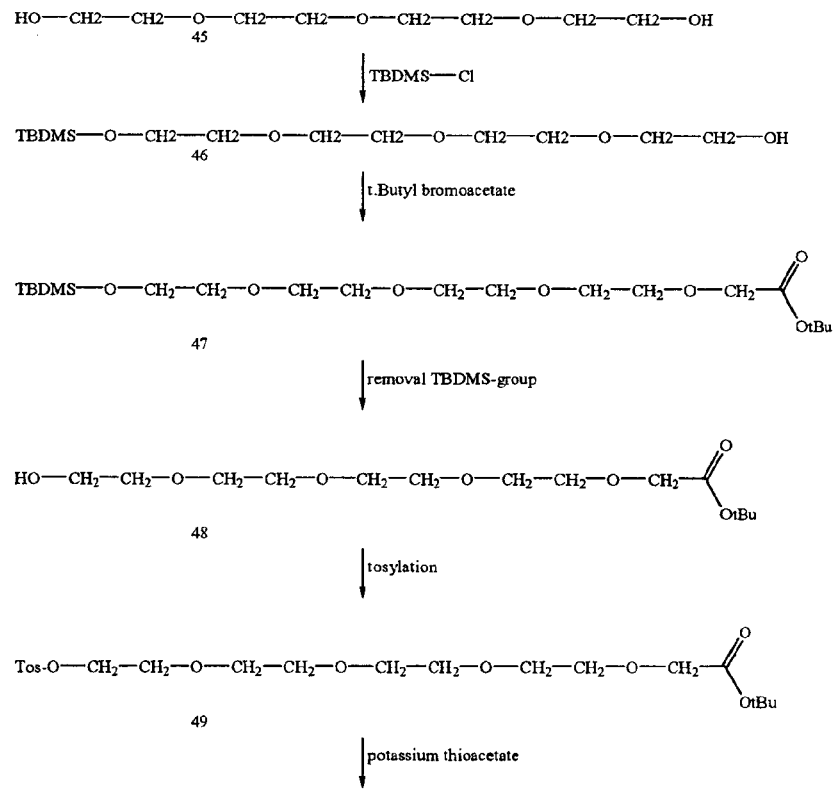

31

-continued

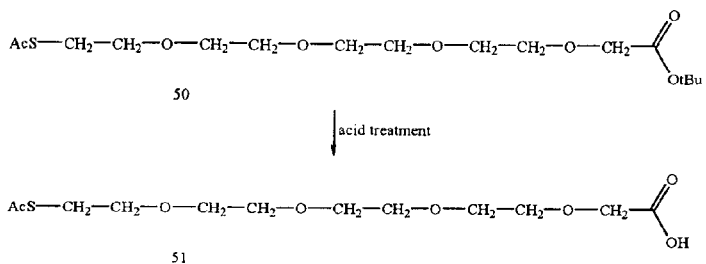

50

↓ acid treatment

51

Conventional work-up and column chromatography of the crude product yielded 1.5 g of compound 49. To a solution of compound 49 (570 mg) in acetone (20 ml) was added potassium thioacetate (350 mg). The solution was left at 20° C. for 1 hour. The mixture was diluted with water and extracted with ethyl acetate. After evaporation of the organic layer and filtration on a column of silica gel 440 mg of compound 50 was isolated. Compound 50 (120 mg) was dissolved in dichloromethane (1.5 ml) and trifluoroacetic acid (0.20 ml) was added at room temperature. After 4 hours of stirring the mixture was diluted with toluene and evaporated. The residue was coevaporated three times with toluene. Column chromatography of the crude product gave 91 mg of compound 51. Compound 51 (29.1 mg) was dissolved in dry dimethylformamide (1.5 ml) and N,N-diisopropylethylamine (12.8 µl) was added. O-(N-succinimidyl)-N,N,N',N'-tetramethyluronium tetrafluoroborate (22.3 mg) was added under a nitrogen atmosphere and the mixture was stirred for 1.5 hours. This stock-solution of active ester 52 was used for spacer elongation of compound 54.

For the preparation of compound 54 the procedure of example 3 for the preparation of compound 34 was followed, the only difference being the use tetrasaccharide 53 instead of compound 31:

Compound 54 (52 mg) was dissolved in a mixture of dimethylformamide (150 µl) and water (150 µl). 4-Methylmorpholine (50 µl) was added and after 5 min of stirring the stock-solution of active ester 52 was added. After 1 hour of stirring the mixture was evaporated and the reside was purified on a Rp-18 column (water:methanol=7:3 v/v) to give 48 mg of compound 55. Compound 55 (48 mg) was coevaporated twice with dimethylformamide, dried and dissolved in dry dimethylformamide (2.1 ml). Triethylamine sulfurtrioxide ((312 mg) was added under a nitrogen atmosphere and the mixture was stirred overnight at 50° C., after which an aqueous solution of sodium hydrogencarbonate was added. The mixture was stirred for 1 hour at room temperature, concentrated to a small volume and desalted on a Sephadex G-25 column. The isolated product was eluted with water on a Dowex WX8 Na$^+$ column to give 73 mg of a sulfated pentasaccharide derivative. This compound was treated with 0.2N hydrochloric acid solution (2.0 ml). After neutralisation the mixture was desalted on a Sephadex G-25 column to give 57 mg of compound 56. Compound 56 (50 mg) was dissolved in 10.7 ml of a hydroxylamine solution in buffer. (To obtain this solution hydroxylamine.hydrochlo-

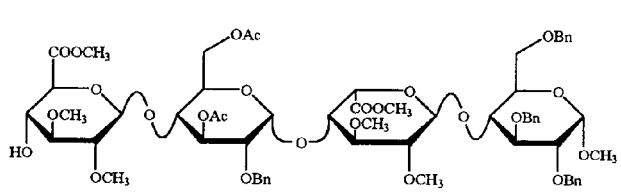

53

Compound 53 was prepared analogously to the procedures described by H. Lucas et al., Angew. Chem. 1993, 32(3), 434–436. In this reference the preparation of a tetrasaccharide (12) is depicted in Scheme 2. For the preparation of compound 53 step d) of Scheme 2 was adapted: a methyl group was introduced instead of a benzyl group by the use of CH$_3$I instead of BnBr. Further reaction steps for the preparation of 53 were similar to the preparation of tetrasaccharide 12 of said reference.

ric acid salt (174 mg) was dissolved in 100 ml of a 0.1M sodium dihydrogenphosphate solution and the pH was adjusted to 7.5 with a 4N sodiumhydroxide solution.) The reaction mixture was stirred for 90 min at 20° C., then the pH was brought to 8.5 and the mixture was stirred for another 24 hours. After desalting and purification of the mixture on a Sephadex G-50 column 40 mg of pure bisconjugate V was isolated. $[\alpha]^{20}_D = +42.9°$ (c=1; water)

33 34
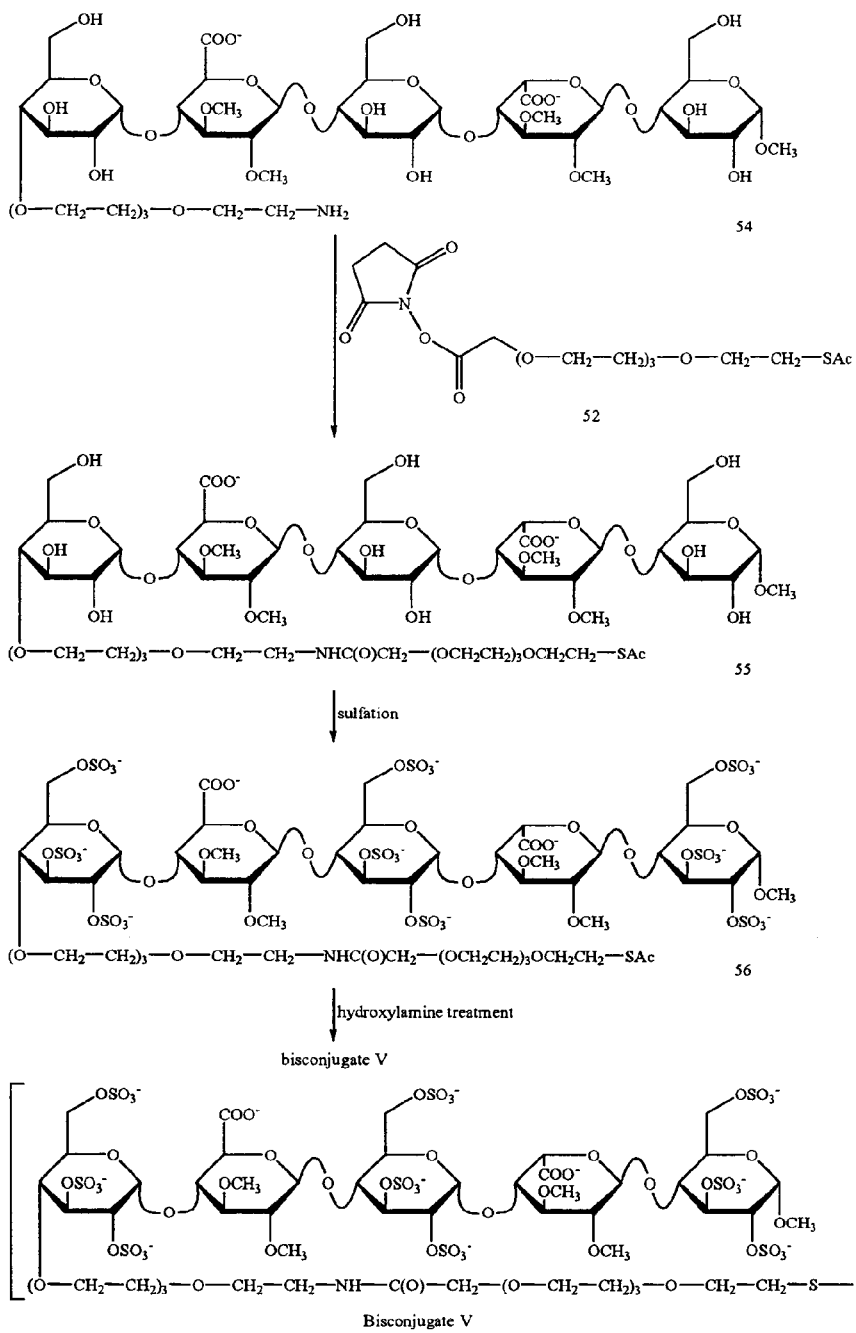
EXAMPLE 6
Bisconjugate VI was prepared in a manner analogous to that described for bisconjugate V, the only difference being the use of tetrasaccharide 57 (which is tetrasaccharide 12 of H. Lucas et al., Angew. Chem. 1993 32(3), 434–436) instead of compound 53. $[\alpha]^{20}_D = +31.6°$ (c=0.82; water)

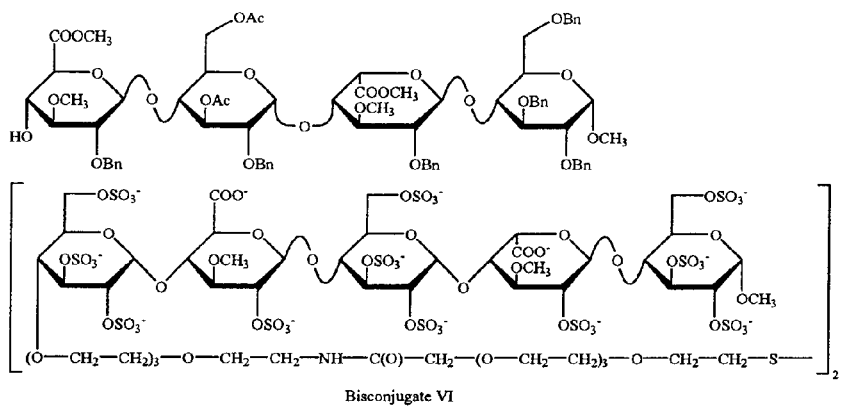

Bisconjugate VI

EXAMPLE 7

For the preparation of bisconjugate VII the procedure of example 5 was followed, the difference being that instead of monoconjugate 54 compound 89 was used. Compound 89 was prepared according to the procedure for the preparation of compound 34 (as described in example 3), using compound 60 instead of monosaccharide 24. $[\alpha]^{20}_D = +66.6°$ (c=0.5 water)

in dimethylformamide at 20° C. The mixture was stirred for 16 hours and the excess of sodium hydride was destroyed with methanol. Water was added and the mixture was extracted with ethyl acetate. After concentration 25 g of compound 59 was isolated. Compound 59 (44 g) was dissolved in dichloromethane (90 ml) and triethylsilane (92 ml) was added. A mixture of trifluoroacetic acid (44 ml) and trifluoroacetic anhydride (0.9 ml) was added dropwise and

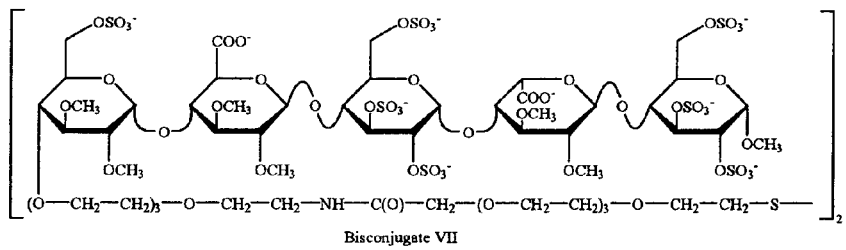

Bisconjugate VII

Preparation of compound 60:

Compound 58 (29 g) and iodomethane (15.5 ml) were dissolved in dimethylformamide (50 ml). The solution was added dropwise to a suspension of sodium hydride (10.5 g)

the mixture was stirred for 1 hour at 20° C. The reaction was quenched with a cold sodium hydrogencarbonate solution, extracted with ethyl acetate, dried and concentrated. Silica gel chromatography of the residue yielded 31 g of compound 60.

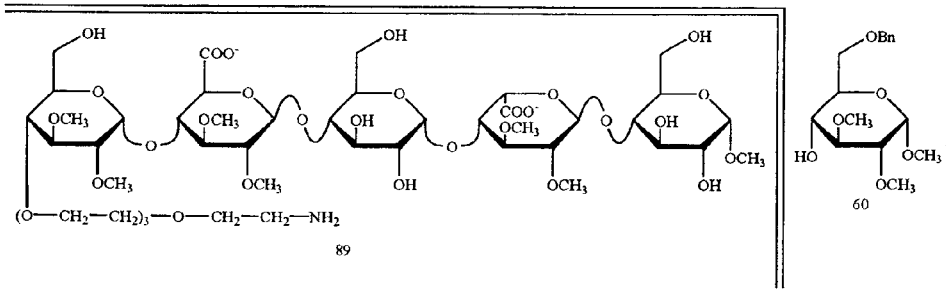

EXAMPLE 8

Monosaccharide 69 was prepared as follows:

To a solution of 1,6-anhydromannose 61 (19.1 g) in acetone (75 ml) and 2,2-dimethoxypropane (75 ml), camphorsulfonic acid (200 mg) was added. The reaction mixture was stirred overnight. Triethylamine was added and a the solvent was evaporated. Dichloromethane was added to the residue, salts were filtered off and the filtrate was evaporated to dryness. Column chromatography of the crude product yielded 15 g of compound 62.

Compound 62 (3.0 g) and tetraethylene glycol di-p-tosylate were dissolved in dry tetrahydrofuran (250 ml). The mixture was heated to 60° C. and sodium hydride (900 mg) was added under nitrogen atmosphere. After 30 min of stirring the mixture was concentrated and purified by column chromatography to give 3.9 g of crude compound 63.

Compound 63 (3.9 g) was dissolved in tetrahydrofuran (25 ml) and N-methylbenzylmaien (1.95 ml) was added. The mixture was heated to reflux temperature for 30 min and concentrated to give 5.0 g of crude compound 64.

Crude compound 64 (5.1 g) was dissolved in 30 ml of methanol:1N hydrochloric acid 9:1 (v/v) and the mixture was stirred for 5 hours at 85° C. After cooling, pyridine (50 ml) was added and the solution was concentrated to give crude compound 65.

Crude compound 65 was dissolved in 75 ml of pyridine:acetic anhydride 2:1 (v/v); 4-dimethylaminopyridine (25 mg) was added and the mixture was stirred for 4 hours at room temperature. The mixture was diluted with toluene and evaporated. The residue was dissolved in ethyl acetate and diluted hydrochloric acid was added. After extraction the acid water layer was brought to pH 10 with sodium hydroxide solution and extracted again with ethyl acetate. The organic layer was dried and concentrated. The crude product was purified by column chromatogrpahy to give 1.86 g of compound 66.

Compound 66 (1.86 g) was dissolved in a mixture of acetic anhydride (45 ml) and trifluoroacetic acid (3.8 ml). The solution was stirred for 60 hours at 20° C. and was then diluted with toluene. After concentration the residue was dissolved in ethyl acetate and washed with sodium hydrogencarbonate. The organic layer was dried and concentrated. Column chromatography of the crude product gave 0.5 g of compound 67.

Compounds 68 and 69 were prepared according to the manner as described in example 3 for compounds 27 and 28, respectively.

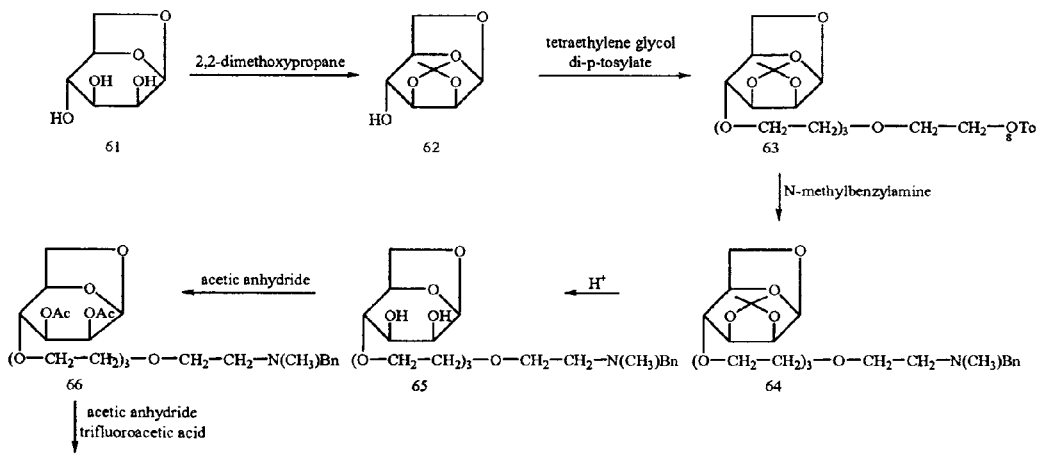

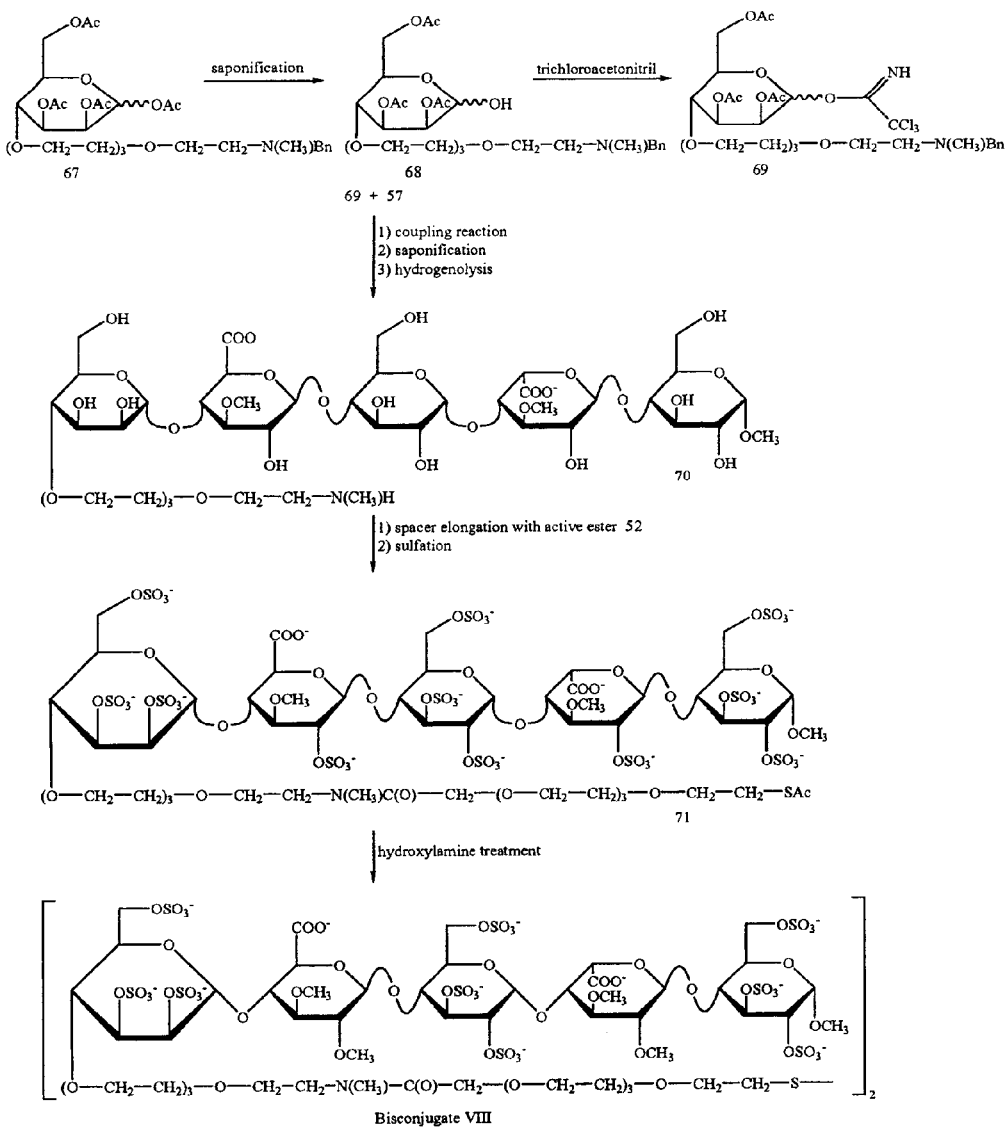

Compound 69 was coupled with tetrasaccharide 57, followed by saponification and hydrogenolysis (as described in example 3 for compounds 32, 33 and 34, respectively) after which compound 70 was obtained.

Compound 70 was treated with active ester 52, followed by sulfation (according to the preparations of compounds 55 and 56, example 5), giving compound 71.

Compound 71 was treated with hydroxylamine (according to the preparation of bisconjugate V from compound 56, example 5) to form bisconjugate VIII. $[\alpha]^{20}_D = +27.3°$ (c=1; water)

EXAMPLE 9

Bisconjugate IX was prepared according to the procedure of example 4, differing at one point: instead of glucopyranosyl imidate 28 an analogus of mannopyranosyl imidate 69 was used, having —N₃ at the end of the tetraetylene glycol side chain instead of —N(Ch₃)Bn. The —N₃ containing compound was prepared by reacting compound 63 with lithium azide instead of N-methylbenzylamine. All other reaction steps towards the azide containing mannopyranosyl imidate were similar to the synthesis of 69. $[\alpha]^{20}_D = +33.2°$ (c=0.25; water)

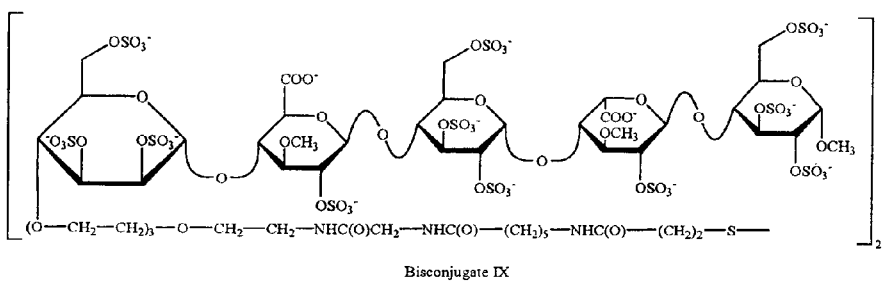

Bisconjugate IX

EXAMPLE 10

For the preparation of bisconjugate X the procedure of example 9 was followed, the difference being the use of tetrasaccharide 53 instead of tetrasaccharide 57 in the preparation of the pentasaccharide moiety. $[\alpha]^{20}_D = +26.5°$ (c=1; water)

for 1 hour. The mixture was then cooled to $-20°$ C. and 21.4 mmol of a 40 mM solution of trimethylsilyl trifluoromethanesulphonate in dichloromethane were added. The reaction mixture was stirred for 15 minutes and then filtered over celite, subsequently washed with an aqueous sodium hydrogencarbonate solution and water and evaporated to dryness. The residue was subjected to acetolysis by dissolv-

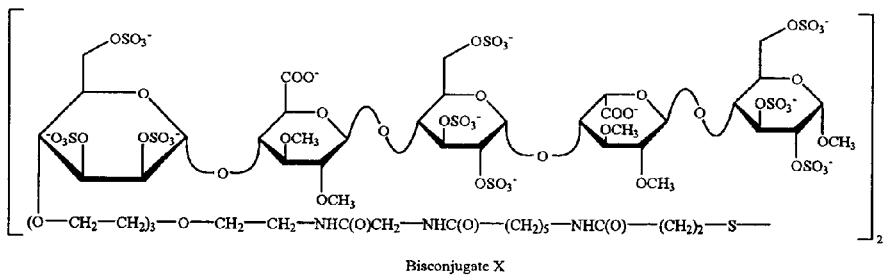

Bisconjugate X

EXAMPLE 11

Bisconjugate XI was prepared from compound 75 according to the conversion of compound 32 into bisconjugate III (example 3), the difference being the application of succinimido N-(benzyloxycarbonyloxy) glycine instead of N-(benzyloxycarbonyloxy) succinimide. $[\alpha]^{20}_D = +25.7°$ (c=0.49; water)

ing it in a mixture of trifluoroacetic acid and acetic anhydride. The reaction product was treated with benzylamine in diethyl ether and thereafter with trichloroacetonitrile in dichloromethane in the presence of potassium carbonate, to obtain compound 73 (yield: 50%). 0.121 mmol of compound 73 and 0.093 mmol of compound 74 (see EP 529715, Preparation IX) were dissolved in 3.2 ml of dichloromethane. In the presence of molecular sieves and under an

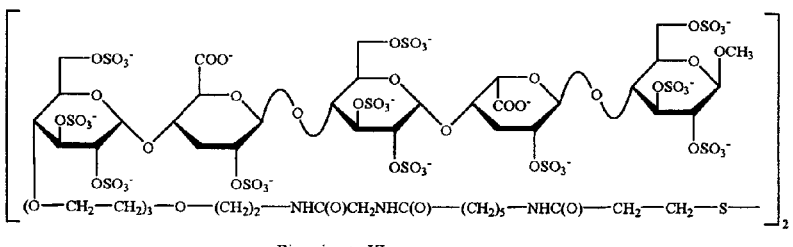

Bisconjugate XI

Preparation of compound 75

214 mmol of compound 28 and 178 mmol of compound 72 (see EP 529715, Preparation V) were dissolved in 4 ml of dichloromethane at room temperature, and 160 mg of molecular sieves 4 Å were added. This mixture was stirred argon atmosphere the mixture was cooled to 31 20° C., and then 0.470 ml of a solution of trimethylsilyl trifluoromethanesulphonate in dichloromethane were added. The reaction mixture was stirred at $-20°$ C. for 1 hour, after which it was filtered, washed with water, evaporated and Preparation of asymmetric bisconjugate XII
Solution A

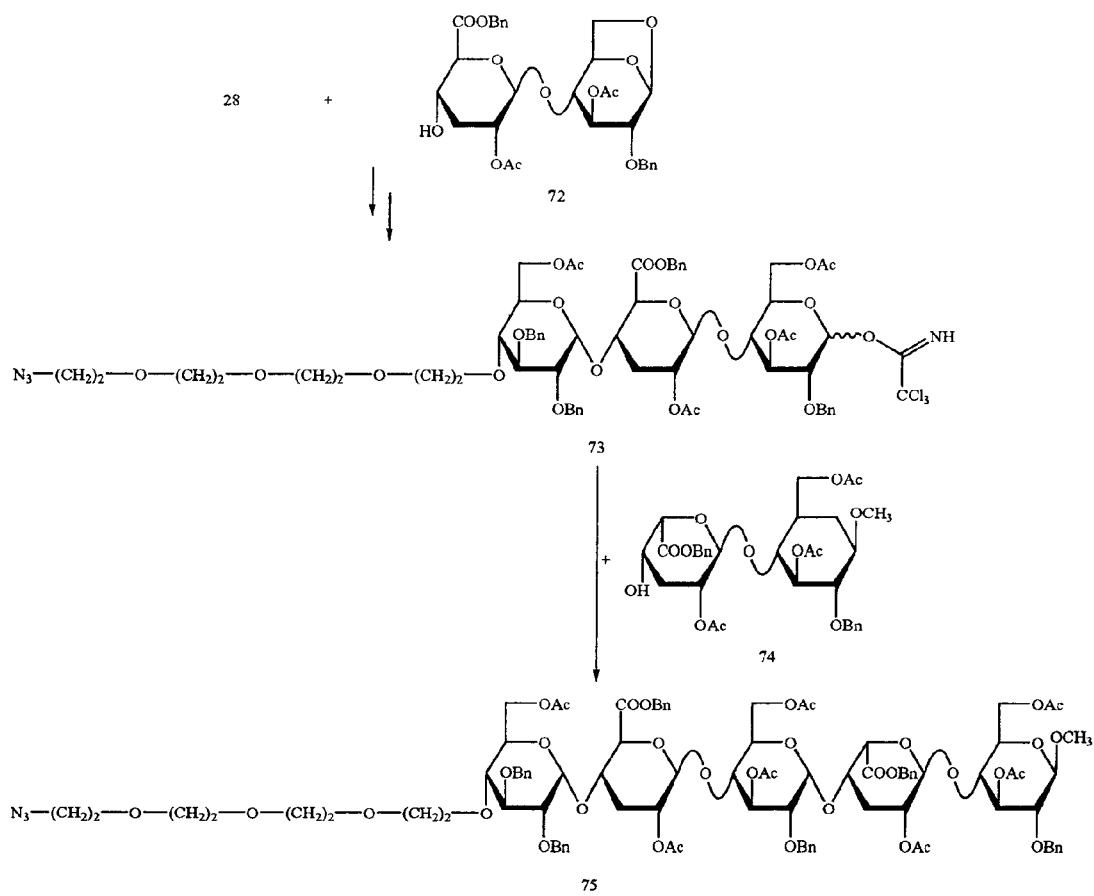

EXAMPLE 12

Maltopentaose 76 (500 mg) was dissolved in 15 ml of pyridine:acetic anhydride=2:1 (v/v), stirred overnight and concentrated. After coevaporation with toluene 930 mg of compound 77 was obtained. The reactions 77→78→79 were performed following the procedures as described for the conversion of 26→27→28 and the subsequent coupling reaction resulting in compound 80 was carried out according to the procedure as described for the coupling reaction of compounds 28 and 31 (see example 3). Compound 80 (300 mg) was dissolved in dry methanol and a small quantity of potassium tert. butoxide was added. The mixture was stirred overnight. Dowex H+ was added to neutralise the mixture and after filtration the filtrate was concentrated to give 180 mg of compound 81. Compound 81 was sulfated according to the procedure as described for compound 35 (example 3), forming compound 82. After hydrogenolysis of compound 82 according to the procedure as described for the conversion of compound 16 into 17 (see example 1), compound 83 was obtained.

Compound 83 (42 mg) was dissolved in a mixture of 0.1M sodium dihydrogen phosphate buffer pH 7.5 (1.3 ml) and dimethylformamide (0.5 ml) and sulfosuccinimidyl 4-(p-maleimidophenyl)butyrate (7 mg) was added. The mixture was stirred for 15 min.

Reaction mixture B

The monoconjugate 71 (17.5 mg) was dissolved in 1.7 ml of a 50 mMol hydroxylamine solution in 0.1M sodium dihydrogen phosphate buffer pH 7.5 under an argon atmosphere. The mixture was stirred for 1 hour giving a solution of compound 84. To this solution 1 equivalent of solution A was added under an argon atmosphere. The mixture was stirred for another 2 hours. During this process also symmetric bisconjugate was formed, which was removed by dithiothreitol treatment. After 30 min of stirring the mixture was purified on a Sephadex G-50 column to give 4.7 mg of asymmetric bisconjugate XII. $[\alpha]^{20}_D$=+40.3+ (c=0.38; water)

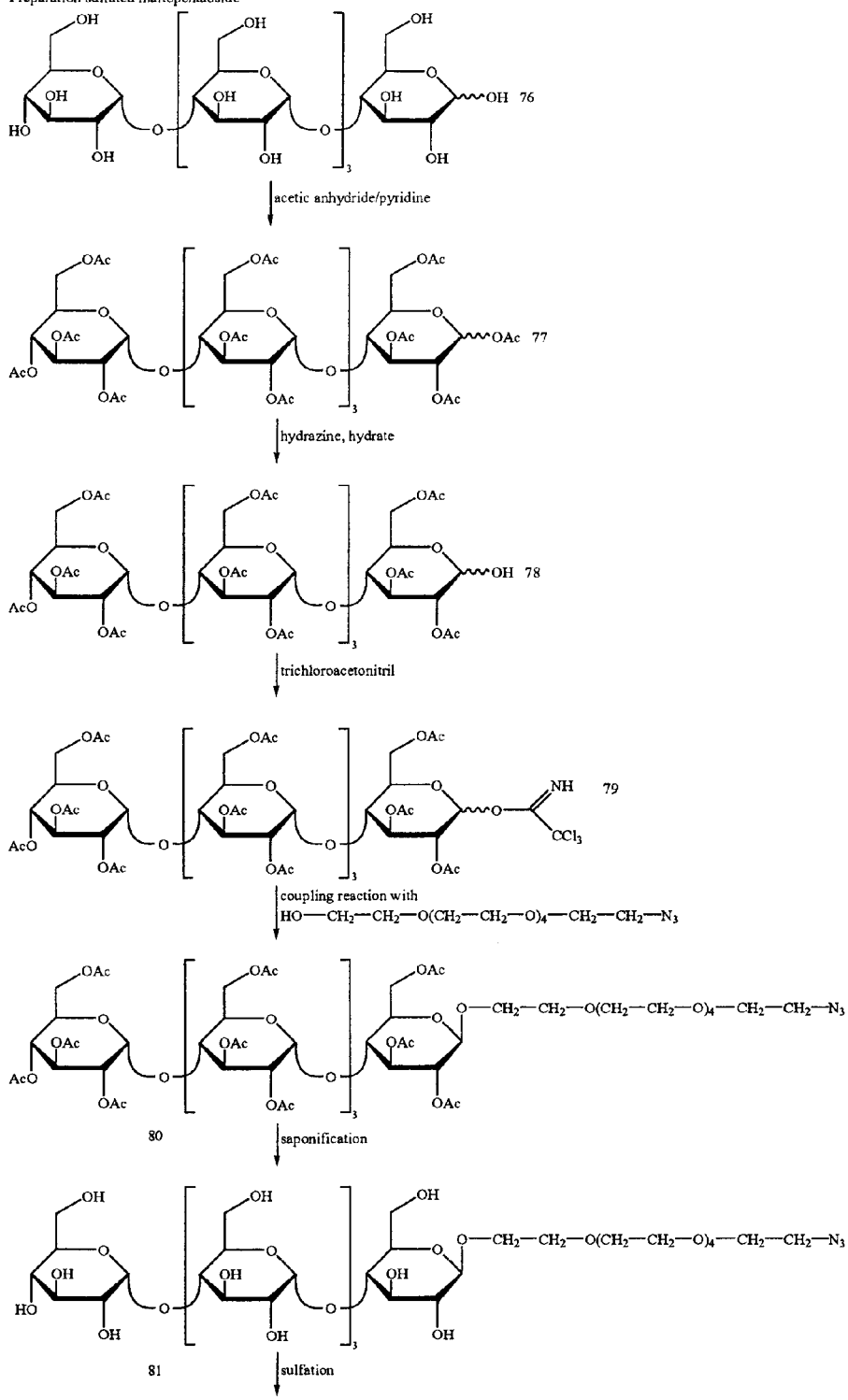

-continued
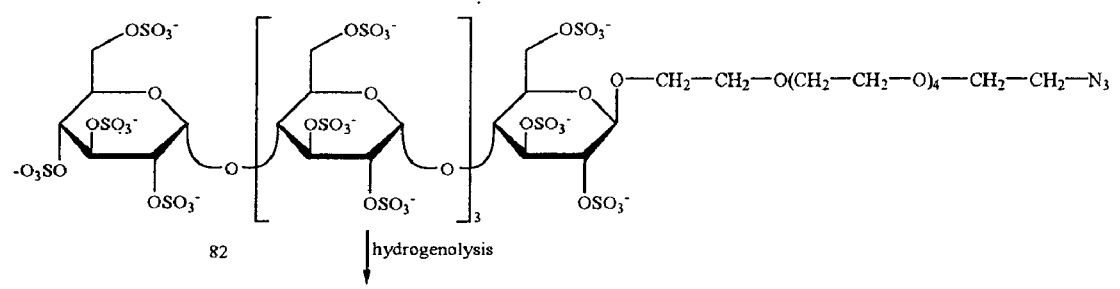
↓ hydrogenolysis
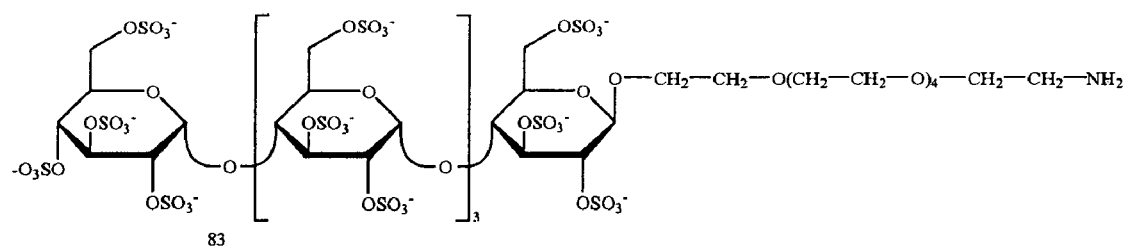
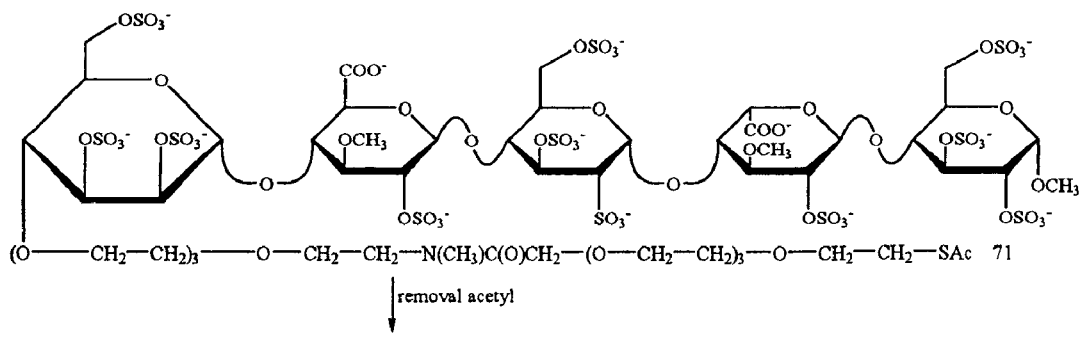
↓ removal acetyl
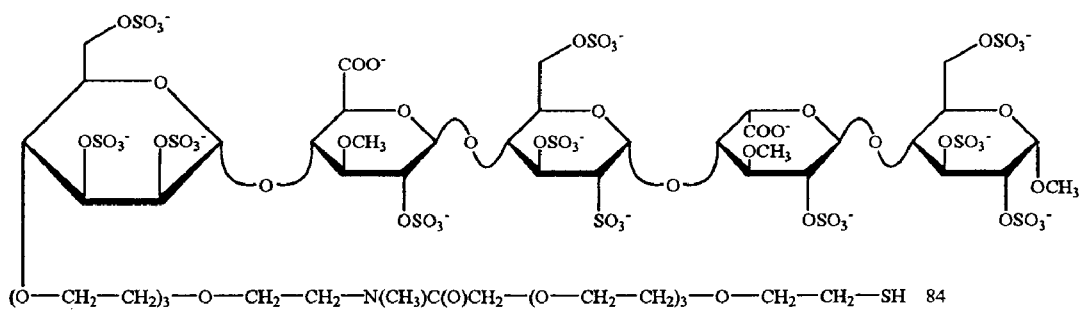
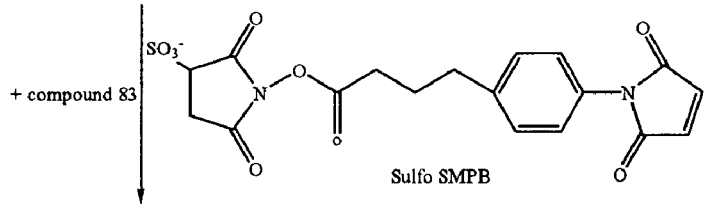
+ compound 83 ↓

-continued
Asymmetric bisconjugate XII
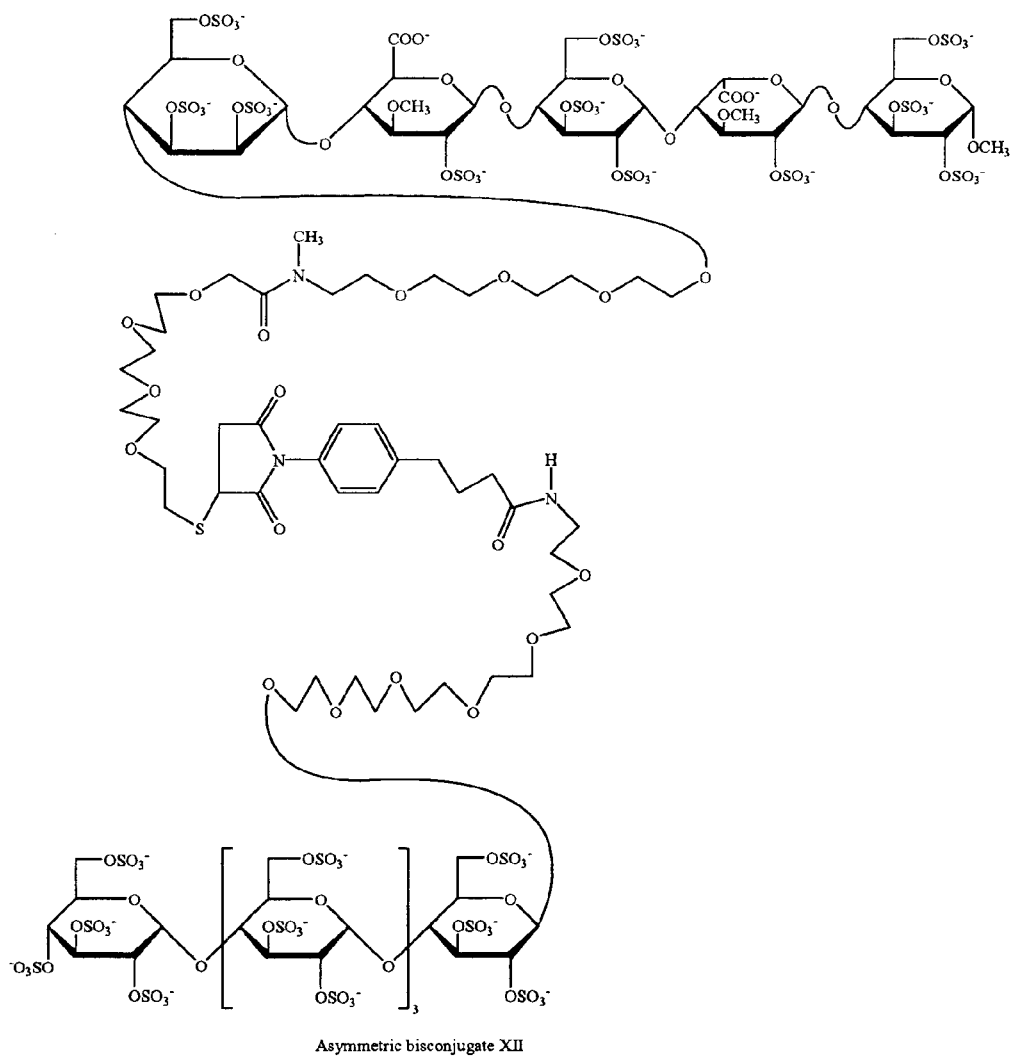
Asymmetric bisconjugate XII
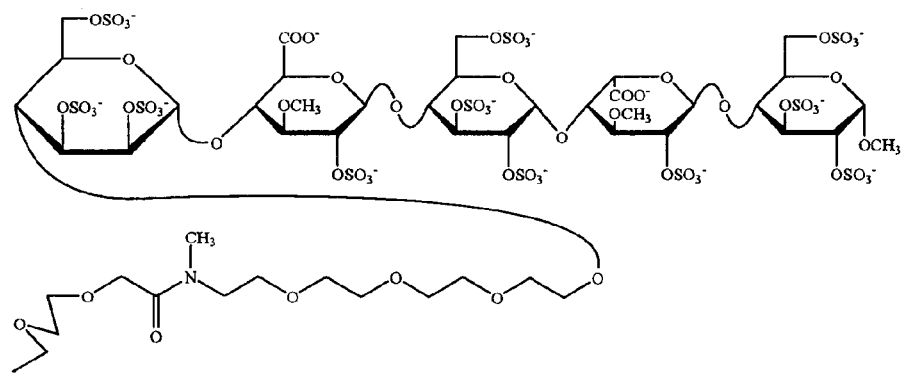

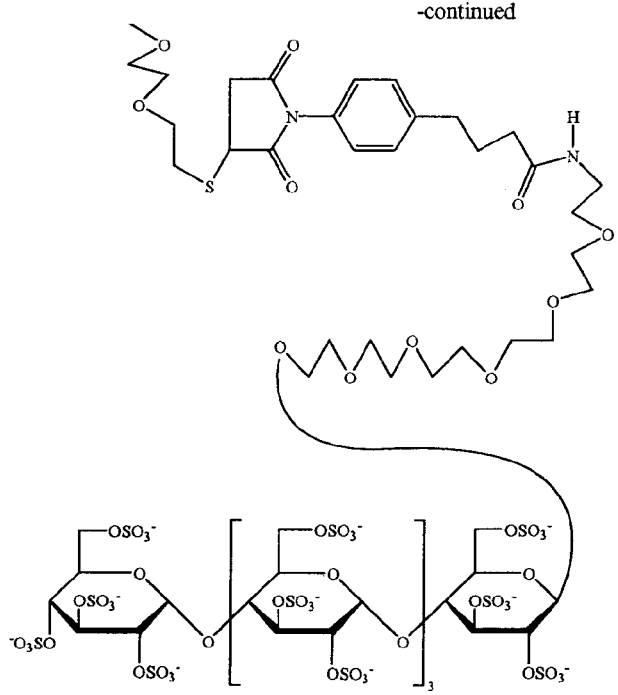

EXAMPLE 13

Asymmetric bisconjugate XIII was prepared according to the procedure as described for the preparation of bisconjugate XII. Instead of pentasaccharide 71 the analogous compound 85 was used. Compound 85 was obtained from the conversion of compound 89 by spacer elongation with active ester 52 and sulfation, as described for the conversion of 54 into 56 (see example 5). Compound 89 was mentioned in example 7. $[\alpha]^{20}_D = +65.4°$ (c=0.09; water)

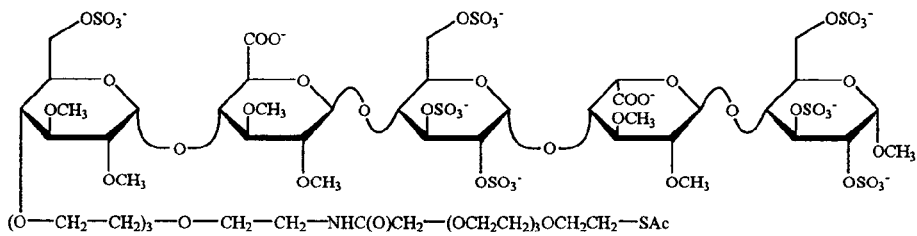

85

53 -continued 54
Asymmetric bisconjugate XIII
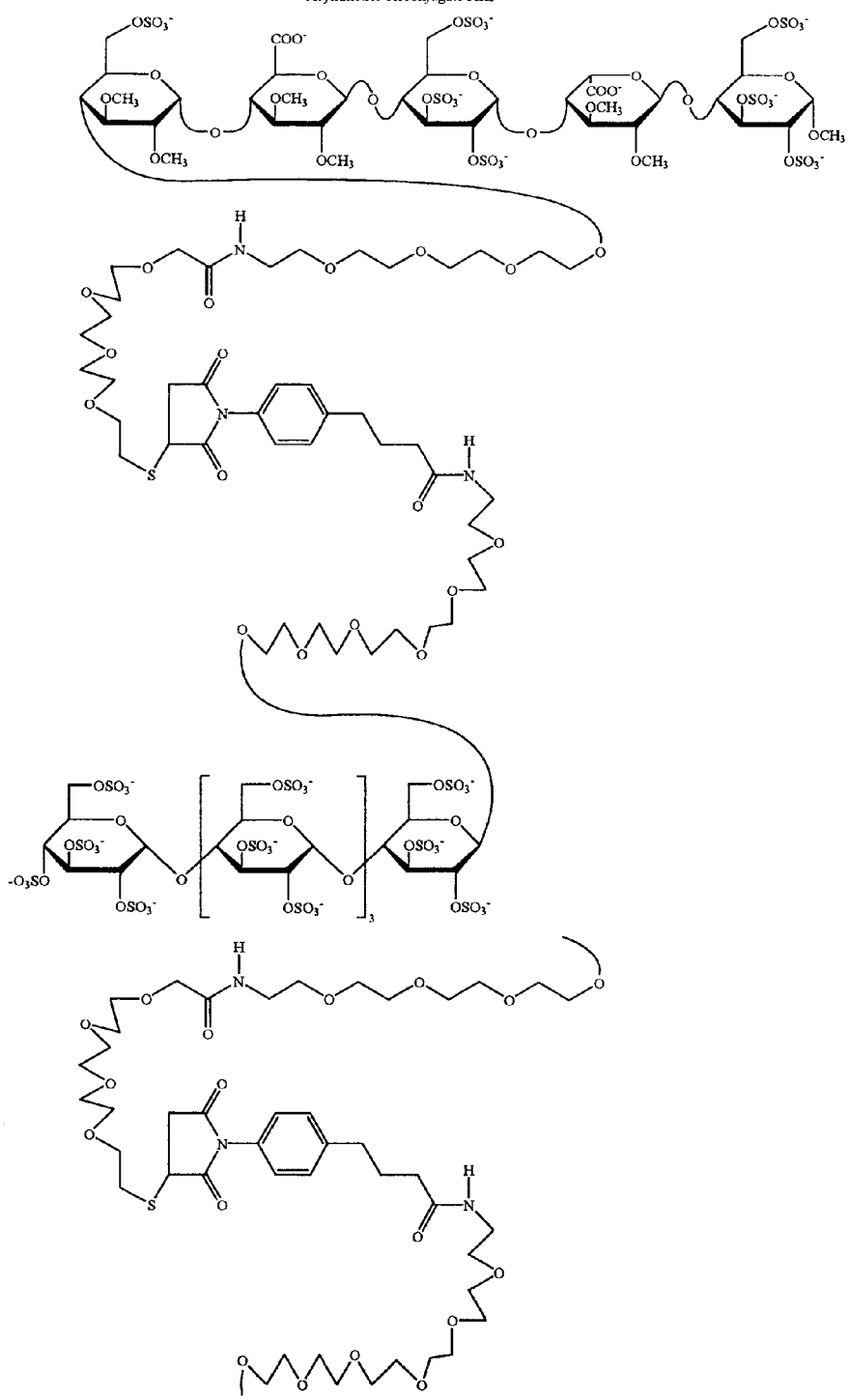

-continued

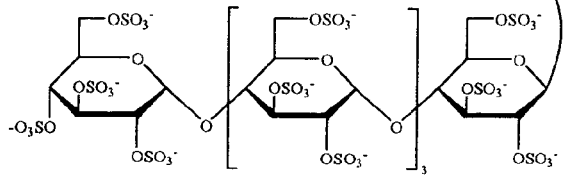

EXAMPLE 14

The sulfated maltotrioside 87 was prepared from compound 86 according to the procedure as described for the preparation of maltopentaoside 83 from compound 76 (see example 12).

Reaction A: Compound 87 (25 mg) was dissolved in 1.0 ml of 0.1M sodium dihydrogen phosphate buffer pH 7.5 and sulfosuccinimidyl-(4-iodoacetyl)aminobenzoate (21 mg) was added. The mixture was stirred for 30 min at 20° C. and purified on a Sephadex G-15 column giving 30 mg of product.

Reaction B: Compound 85 (15 mg) was dissolved in 1.7 ml of a 50 mMol. hydroxylamine solution in 0.1M sodium dihydrogen phosphate buffer pH 7.5 under an argon atmosphere. The mixture was stirred for 1 hour at 20° C. and purified on a Sephadex G-25 column giving 14 mg of compound 88.

The product obtained from reaction A and a compound 88 were dissolved in 1 ml 0.1M sodium hydrogenphosphate buffer and stirred for 60 hours under an argon atmosphere at 4° C. The symmetric bisconjugate was removed by dithiothreitol treatment. After 30 min of stirring the mixture was purified on a Sephadex G-50 column to give 13 mg of bisconjugate XIV. $[\alpha]^{20}_D = +55.7°$ (c=0.46; water)

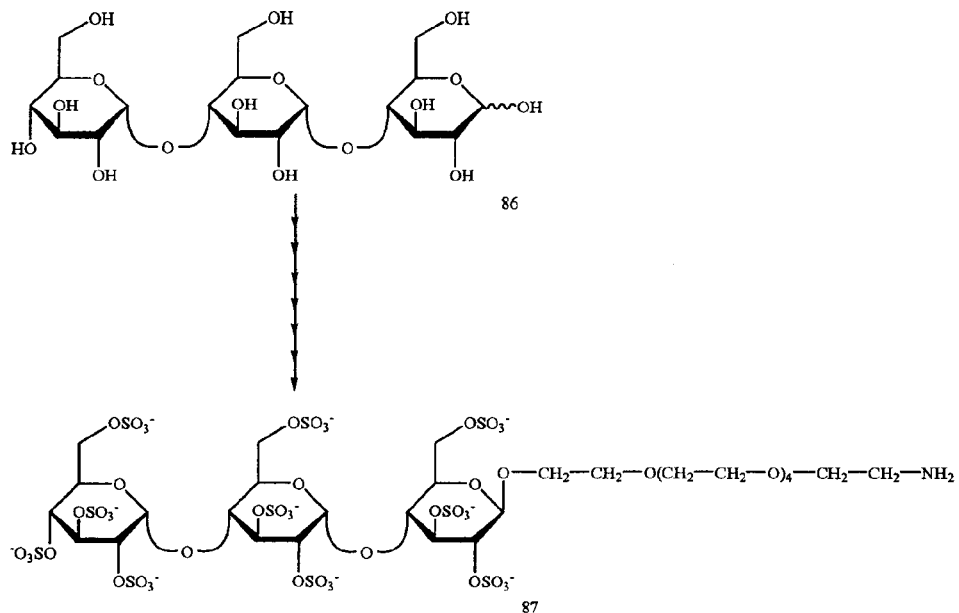

57  58
-continued
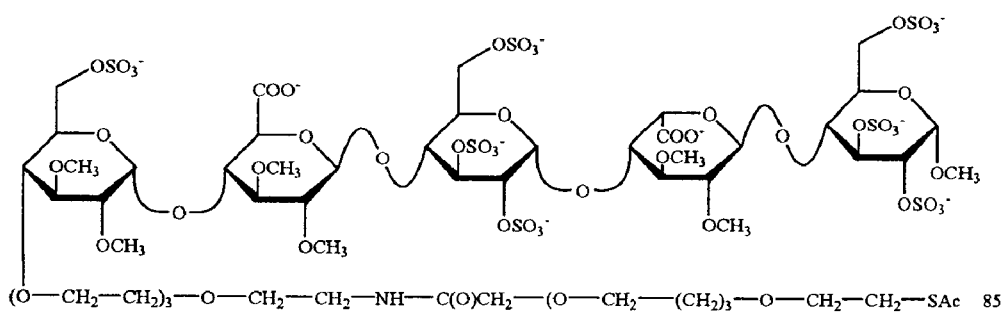
↓ hydroxylamine
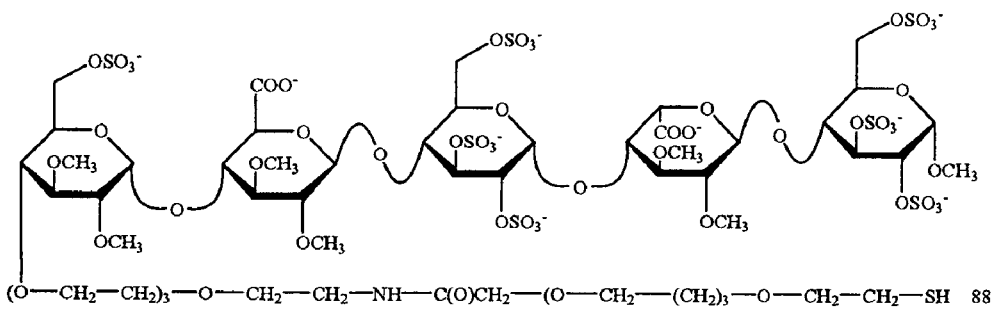
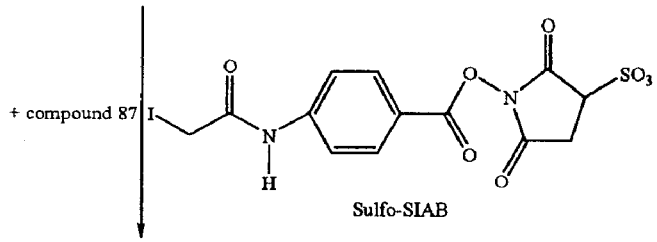
↓
bisconjugate XIV -continued Asymmetric bisconjugate XIV

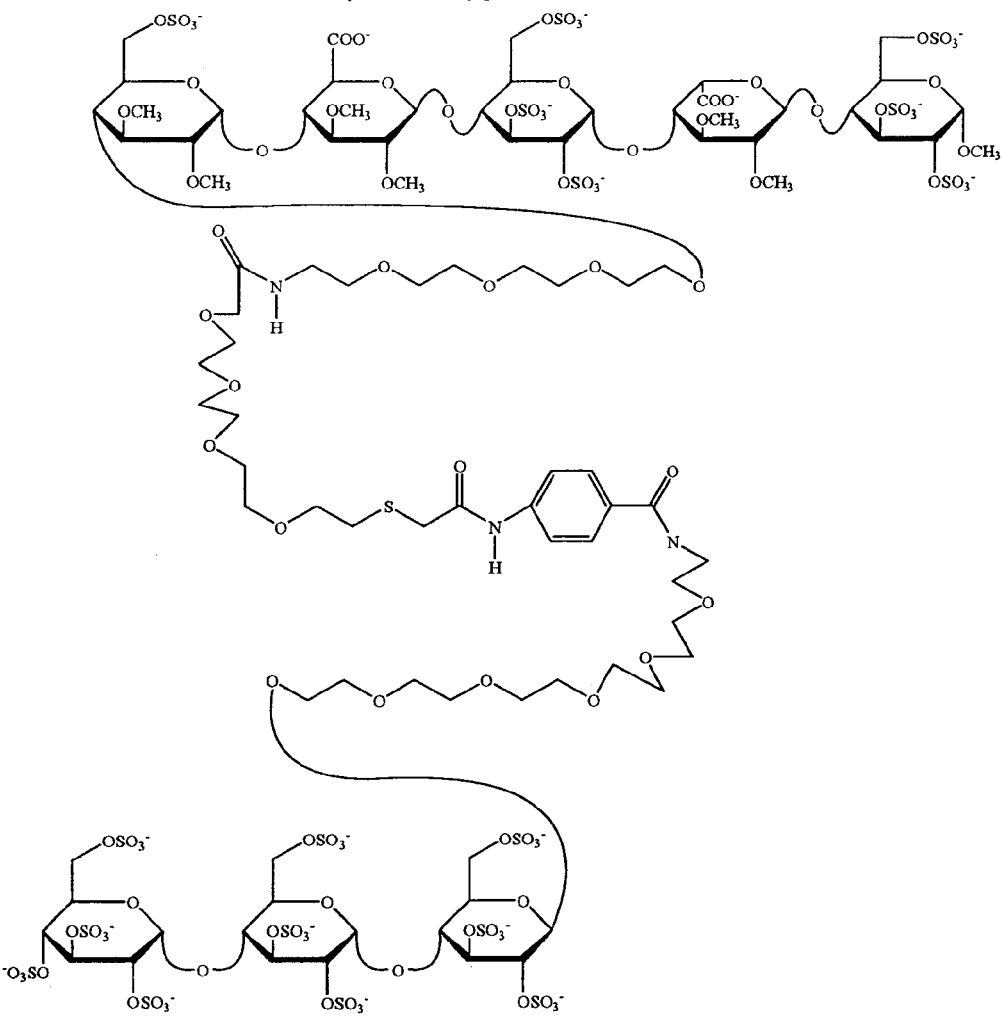

EXAMPLE 15

Asymmetric bisconjugate XV was prepared according to the procedure as described for the preparation of asymmetric bisconjugate XIV. Instead of maltotrioside 87 compound 91 was used. The sulfated cellobiose derivative 91 was prepared from cellobiose octaacetate 90 according to the procedure as described for the preparation of compound 83 from compound 77 (example 12). $[\alpha]^{20}_D = +51.2°$ (c=0.83; water)

61 62
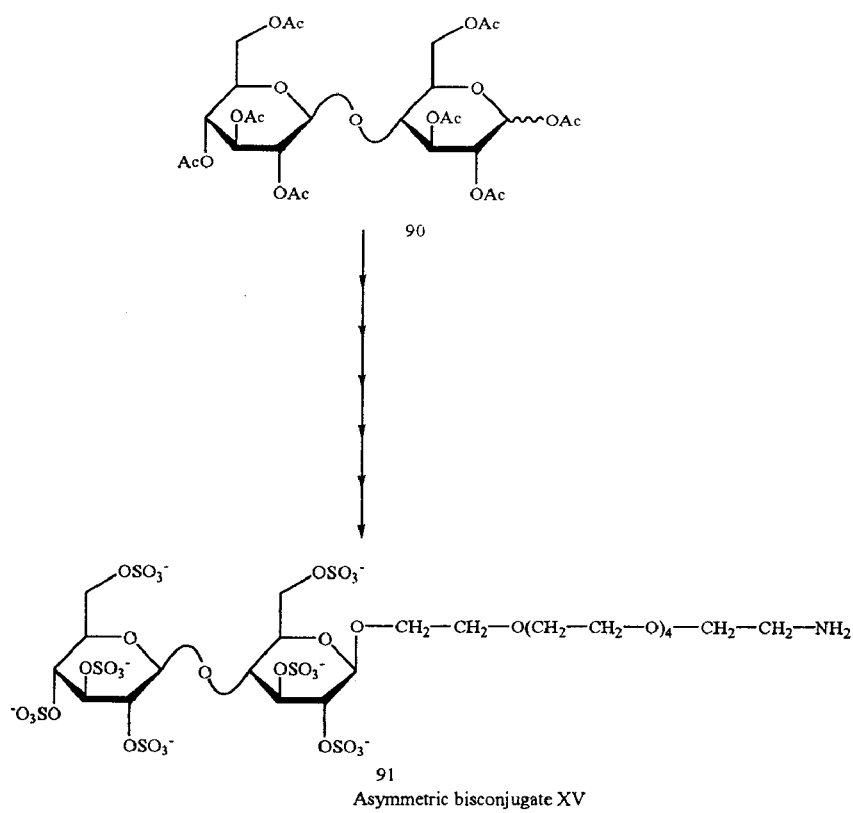
91
Asymmetric bisconjugate XV 63 64
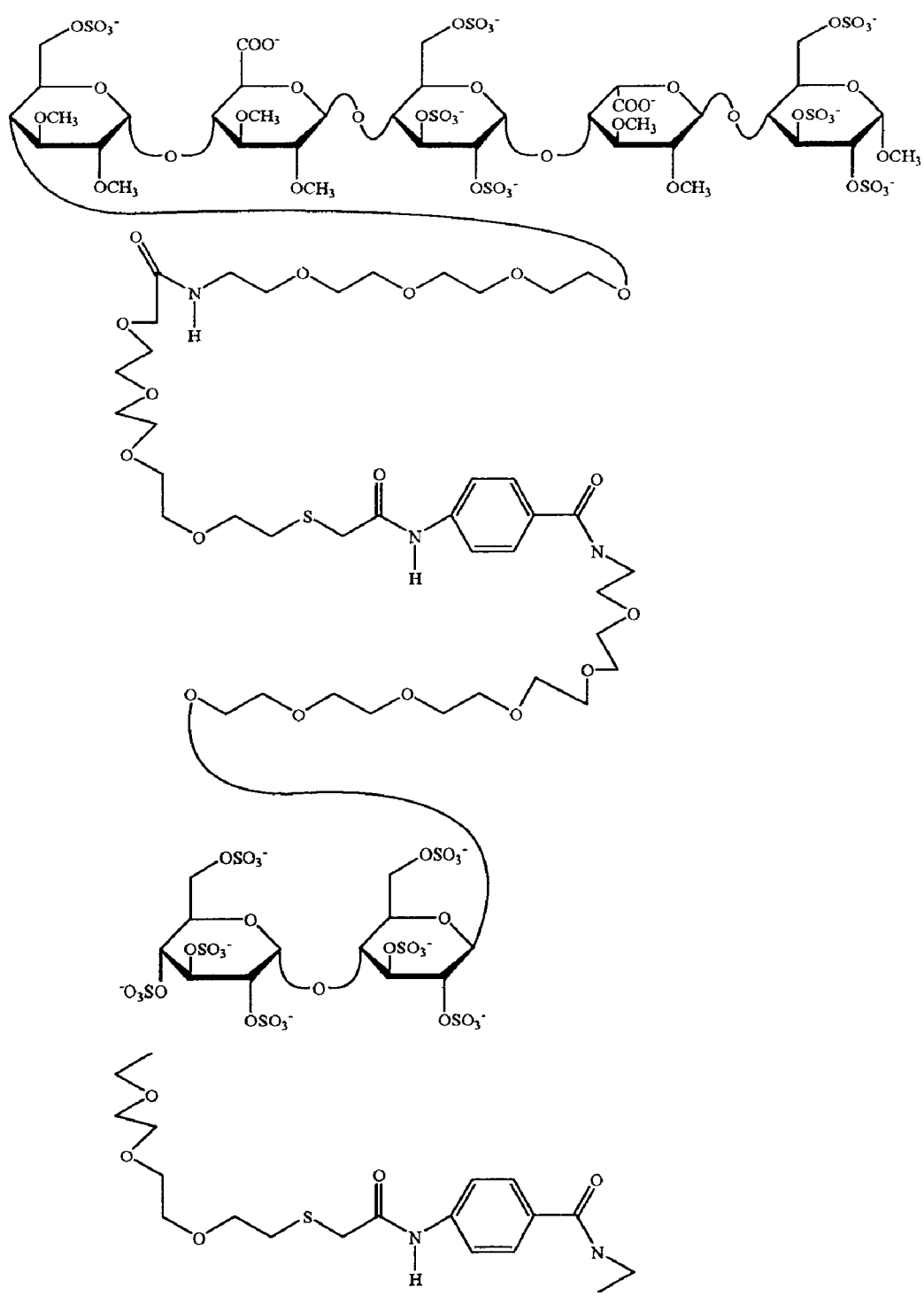

-continued

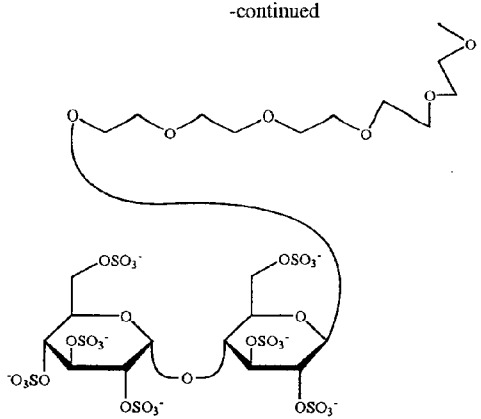

We claim:

1. A bis/mixed conjugate consisting of two saccharides and a spacer, each saccharide being the same or different and comprising two to six monosaccharide units, at least one unit being uronic acid, wherein at least one of the saccharides per se has anti-thrombotic activity, and the spacer connects at least one saccharide to the other through its non-reducing end, the chain length of the spacer consisting of at least twenty atoms.

2. The bis/mixed conjugate of claim 1, wherein at least one of the saccharides per se has affinity for at least one of AT-III and HC-II and/or has at least one activity selected from the group consisting of anti-factor IIa and anti-factor Xa activity.

3. The bis/mixed conjugate of claim 2, wherein both saccharides per se have affinity for at least one of AT-III and HC-II and/or have at least one activity selected from the group consisting of anti-factor IIa and anti-factor Xa activity.

4. The bis/mixed conjugate of claim 1, wherein at least one of the saccharides has the formula

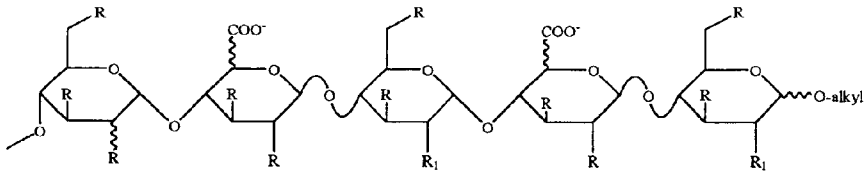

wherein each

R is independently selected from H, OH, $OSO_3^-$ and C1–C8 alkoxy;

$R_1$ is independently selected from $OSO_3^-$ and $NSHO_3^-$; and the negative charges are compensated by hydrogen or an alkali metal cation.

5. The bis/mixed conjugate of claim 1, wherein at least one of the saccharides has the formula:

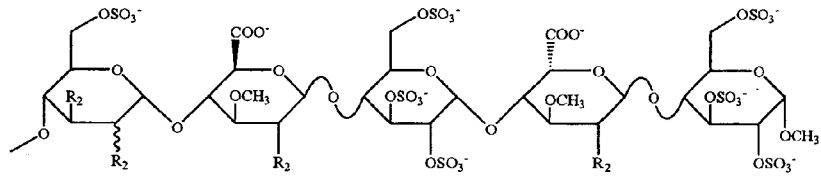

wherein $R_2$ is independently $OSO_3^-$ or $OCH_3$.

6. The bis/mixed conjugate of claim 1, wherein the spacer has the formula

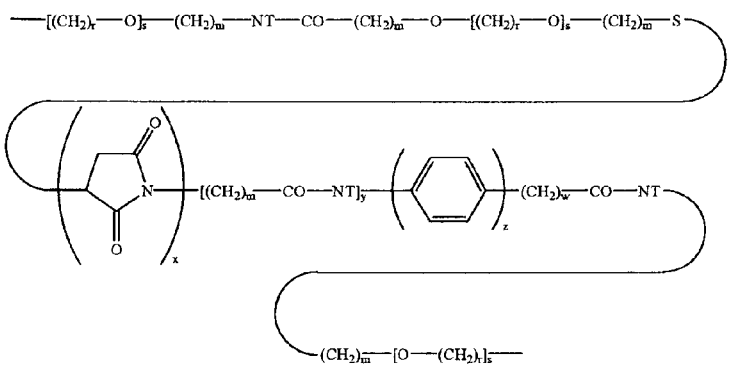

wherein
one of the two free valencies of the spacer is attached to the non-reducing end of one of the saccharides and the other free valency of the spacer is attached to the reducing or non-reducing end of the other saccharide, and T is independently H or C1–C8 alkyl; m is independently 1–8; r is independently 2–4; s is independently 1–12; w is 0–10; x is 0 or 1; y is 0 or 1; z is 0 or 1, and the total number of atoms in the spacer is 20–120.

7. A pharmaceutical composition comprising the bis/mixed conjugate of claim 1 and pharmaceutically acceptable auxiliaries.

8. A method for the treatment or prevention of thrombotic disorders or smooth muscle cell proliferation comprising administering an effective amount of a composition according to claim 7.

9. The bis/mixed conjugate of claim 1, wherein the length of the spacer is from 20 to 120.

10. The bis/mixed conjugate of claim 1, wherein the spacer has the formula:

-{Q-NT-CO—[(CH$_2$)$_n$-NT-CO—(CH$_2$)$_m$]$_p$—S—}$_2$ or
-{Q-O—[CH$_2$)$_n$—O]$_p$—(CH$_2$)$_m$—S—}$_2$ wherein
one of the two groups Q is attached to the non-reducing end of one of the saccharides and the other group Q is attached to the reducing or non-reducing end of the other saccharide, and each of the groups Q is a phenylene (C$_6$H$_4$) group or —[(CH$_2$O)$_q$—(CH$_2$)$_r$—O]$_s$—[(CH$_2$)$_t$-NT-CO]$_u$—(CH$_2$)$_v$, and T is independently hydrogen or C1–C8 alkyl; q is 0 or 1; r and t are independently 2–4; and s is 1–12; u and v are independently 1–6; n is 1–8; m is 1–8; p is 1–12; and the total number of atoms in the spacer is 20–120.

11. The bis/mixed conjugate of claim 1, wherein the spacer has the formula wherein
one of the two groups Φ is attached to the non-reducing end of one of the saccharides and the other group Φ is attached to the reducing or non-reducing end of the other saccharide, and Φ denotes a phenylene (C$_6$H$_4$) group; n, m and o are independently 1–8; and the total number of atoms in the spacer is 20–120.

12. The bis/mixed conjugate of claim 1, which has the formula

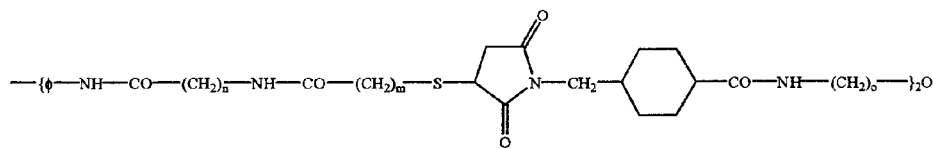

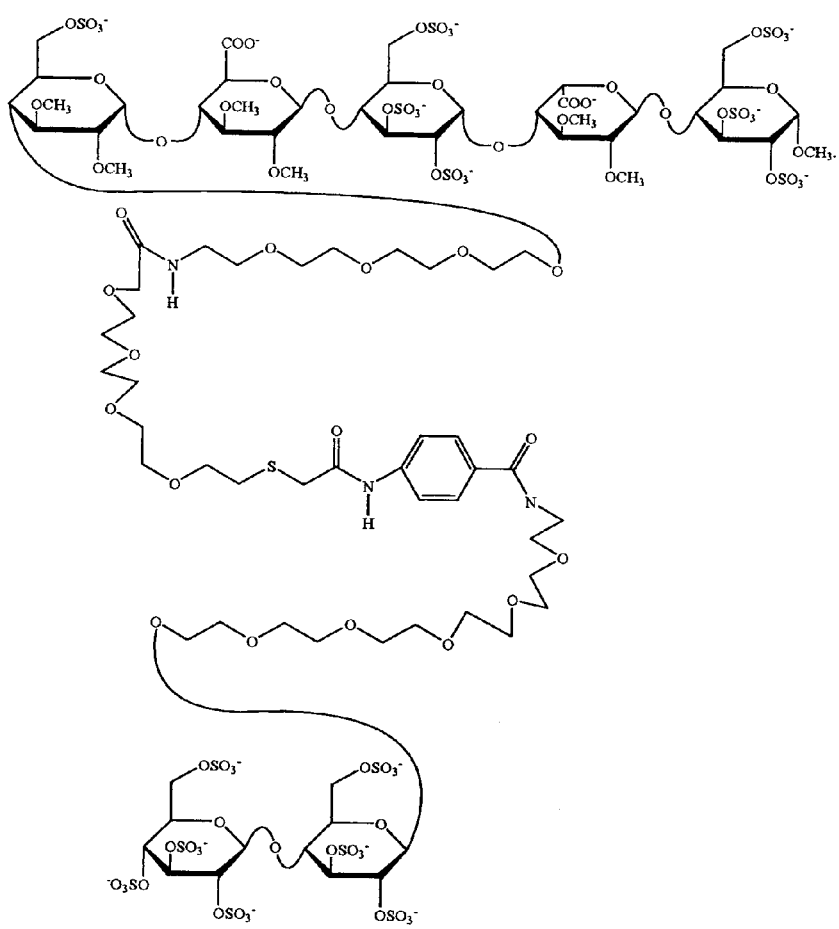
69  70
* * * * *